United States Patent [19]

Wilson et al.

[11] Patent Number: 4,801,364
[45] Date of Patent: Jan. 31, 1989

[54] SEPARATION AND CONVERSION PROCESSES USING METAL ALUMINOPHOSPHATES

[75] Inventors: Stephen T. Wilson, Shrub Oak; Edith M. Flanigen, White Plains, both of N.Y.

[73] Assignee: UOP, DesPlains, Ill.

[21] Appl. No.: 794,416

[22] Filed: Nov. 4, 1985

Related U.S. Application Data

[62] Division of Ser. No. 514,334, Jul. 15, 1983.

[51] Int. Cl.$^4$ .................. C10G 11/02; C10G 47/02
[52] U.S. Cl. .................. 208/108; 208/114; 208/143; 208/135; 208/46; 585/502
[58] Field of Search .................. 208/114, 46, 106, 107, 208/142, 143, 113, 135, 213, 108; 585/502, 446, 133, 134, 734, 480, 407

[56] References Cited

U.S. PATENT DOCUMENTS

| | | | |
|---|---|---|---|
| 3,433,792 | 3/1969 | Adams et al. | 260/290 |
| 3,941,871 | 3/1976 | Dwyer et al. | 423/326 |
| 4,105,541 | 8/1978 | Plank et al. | 208/111 |
| 4,107,083 | 8/1978 | Adams et al. | 208/139 |
| 4,283,306 | 8/1981 | Herkes | 502/251 |
| 4,310,440 | 1/1982 | Wilson et al. | 423/305 |
| 4,337,173 | 6/1982 | Otake | 423/306 |
| 4,385,994 | 5/1983 | Wilson et al. | 210/689 |
| 4,397,825 | 8/1983 | Whittam | 423/277 |
| 4,400,365 | 8/1983 | Haacke et al. | 423/306 |
| 4,420,467 | 12/1983 | Whittam | 423/328 |
| 4,440,871 | 4/1984 | Lok et al. | 502/214 |
| 4,456,582 | 6/1984 | Marosi et al. | 423/277 |
| 4,512,875 | 4/1985 | Long et al. | 208/114 |
| 4,567,029 | 1/1986 | Wilson et al. | 423/306 |

OTHER PUBLICATIONS

Kirk-Othmer, Encyclopedia of Chemical Technology, Third Edition, vol. 3, pp. 334–335, John Wiley & Sons, (1978).
"Dimensions of Phosphates", Proc. Int. Congr. Phosphorus Comp. pp. 145–163 (1980).
"Insoluble Compounds in Ammonium Polyphosphate Made from Wet-Process Phosphoric Acid", J. Agr. Food Chem., 16 691–697 (1968).
"A Zinc Phosphate Analogue of Analcime: Kehoeite", Mineral Mag., 33 pp. 799–803 (1964).
"Ternary Aluminum Phosphates with Bivalent Cations", Z. anorgan. u. allgem. Chem. 302, 121–135 (1959).
Chem. Abst. 65:3846h; Alkylpyridines Production (Shell Int. Research).
Aluminophosphates Broaden Shape Selective Catalyst Types, Haggin, J., C & EN, Jun. 20, 1983.

Primary Examiner—Robert L. Stoll
Assistant Examiner—R. Bruce Breneman
Attorney, Agent, or Firm—Richard G. Miller

[57] ABSTRACT

Novel class of crystalline microporous metal aluminophosphate compositions containing as lattice constituents in addition to $AlO_2$ and $PO_2$ structural units, one or a mixture of two or more of the metals Mg, Mn, Co and Zn in tetrahedral coordination with oxygen atoms. These compositions are prepared hydrothermally using organic templating agents and are suitably employed as catalysts or adsorbents.

11 Claims, 3 Drawing Sheets

SEPARATION AND CONVERSION PROCESSES USING METAL ALUMINOPHOSPHATES

This application is a division of prior U.S. application Ser. No. 514,334, filing date July 15, 1983.

BACKGROUND OF THE INVENTION

1. Field of the Invention

The present invention relates to the use of a novel class of crystalline microporous metal aluminophosphates as catalysts. More particularly the invention relates to novel magnesium aluminophosphates, zinc aluminophosphates, cobalt aluminophosphates and manganese aluminophosphates. These compositions are prepared hydrothermally from gels containing reactive compounds of phosphorus, aluminum, at least one of the group magnesium, manganese, cobalt and zinc, and organic templating agents which function in part to determine the course of the crystallization mechanism and hence the structure of the crystalline product.

2. Description of the Prior Art

Molecular sieves of the crystalline aluminosilicate zeolite type are well known in the art and now comprise over 150 species of both naturally occurring and synthetic compositions. In general the crystalline zeolites are formed from corner-sharing $AlO_2$ and $SiO_2$ tetrahedra and are characterized by having pore openings of uniform dimensions, having a significant ion-exchange capacity and being capable of reversibly desorbing an adsorbed phase which is dispersed throughout the internal voids of the crystal without displacing any atoms which make up the permanent crystal structure.

Other crystalline microporous compositions which are not zeolitic, i.e. do not contain $AlO_2$ tetrahedra as essential framework constituents, but which exhibit the ion-exchange and/or adsorption characteristics of the zeolites are also known. Metal organosilicates which are said to possess ion-exchange properties, have uniform pores and be capable of reversibly adsorbing molecules having molecular diameters of about 6 A or less are reported in U.S. Pat. No. 3,941,871 issued Mar. 2, 1976 to Dwyer et al. A pure silica polymorph, silicalite, having molecular sieving properties and a neutral framework containing neither cations nor cation sites is disclosed in U.S. Pat. No. 4,061,724 issued Dec. 6, 1977 to R. W. Grose et al.

A recently reported class of microporous compositions and the first framework oxide molecular sieves synthesized without silica, are the crystalline aluminophosphate compositions disclosed in U.S. Pat. No. 4,310,440 issued Jan. 12, 1982 to Wilson et al. These materials are formed from $AlO_2$ and $PO_2$ tetrahedra and have electrovalently neutral frameworks as in the case of silica polymorphs. Unlike the silica molecular sieve, silicalite, which is hydrophobic due to the absence of extra-structural cations, the aluminophosphate molecular sieves are moderately hydrophilic, apparently due to the difference in electronegativity between aluminum and phosphorus. Their intracrystalline pore volumes and pore diameters are comparable to those known for zeolites and silica molecular sieves.

In copending and commonly assigned application Ser. No. 400,438, filed July 26, 1982, there is described a novel class of silicon-substituted aluminophosphates which are both microporous and crystalline. The materials have a three-dimensional crystal framework of $PO_2^+$, $AlO_2^-$ and $SiO_2$ tetrahedral units and, exclusive of any alkali metal or calcium which may optionally be present, an as-synthesized empirical chemical composition on an anhydrous basis of:

wherein "R" represents at least one organic templating agent present in the intracrystalline pore system: "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular silicoaluminophosphate species involved; "x", "y", and "z" represent the mole fractions of silicon, aluminum and phosphorous, respectively, present as tetrahedral oxides. The minimum value for each of "x", "y", and "z" is 0.01 and preferably 0.02. The maximum value for "x" is 0.98; for "y" is 0.60; and for "z" is 0.52. These silicoaluminophosphates exhibit several physical and chemical properties which are characteristic of aluminosilicate zeolites and aluminophosphates.

Although a number of mineral species exist which contain either zinc, magnesium, manganese or cobalt in conjunction with aluminum and phosphorus, only the zinc-containing mineral kehoeite has a microporous crystalline structure and exhibits molecular sieving and ion-exchange properties. While it has been proposed that kehoeite has an analcime-type structure, [D. McConnell, Mineral Mag., Vol. 33, pg. 799 (1964)] the evidence is not conclusive due to poor agreement between X-ray powder diffraction pattern data, and the apparent necessity for a highly defective framework for kehoeite in order to match the unit cell content of analcime. In any event, zinc is not purported to be a framework constituent, but is present as a charge-balancing cation for the framework of linked $AlO_2^-$, $H_3O_2^-$ and $PO_2^+$ tetrahedral units.

Crystalline ternary aluminum phosphates and the method for their preparation are reported by Otto Schmitz-Dumont and Werner Hoffman in Z. Anorg. u. Allgem. Chem. 302, 121–135 (1959). Of the three structural types synthesized, only types (II) and (III) contain magnesium, cobalt or zinc, and these are found to lose water of hydration only at substantially elevated temperatures (350° C.) and to become amorphous prior to or upon complete dehydration. Thus these materials are unlike the materials of the present invention which can be completely and reversibly dehydrated without becoming amorphous.

SUMMARY OF THE INVENTION

Figure 1:
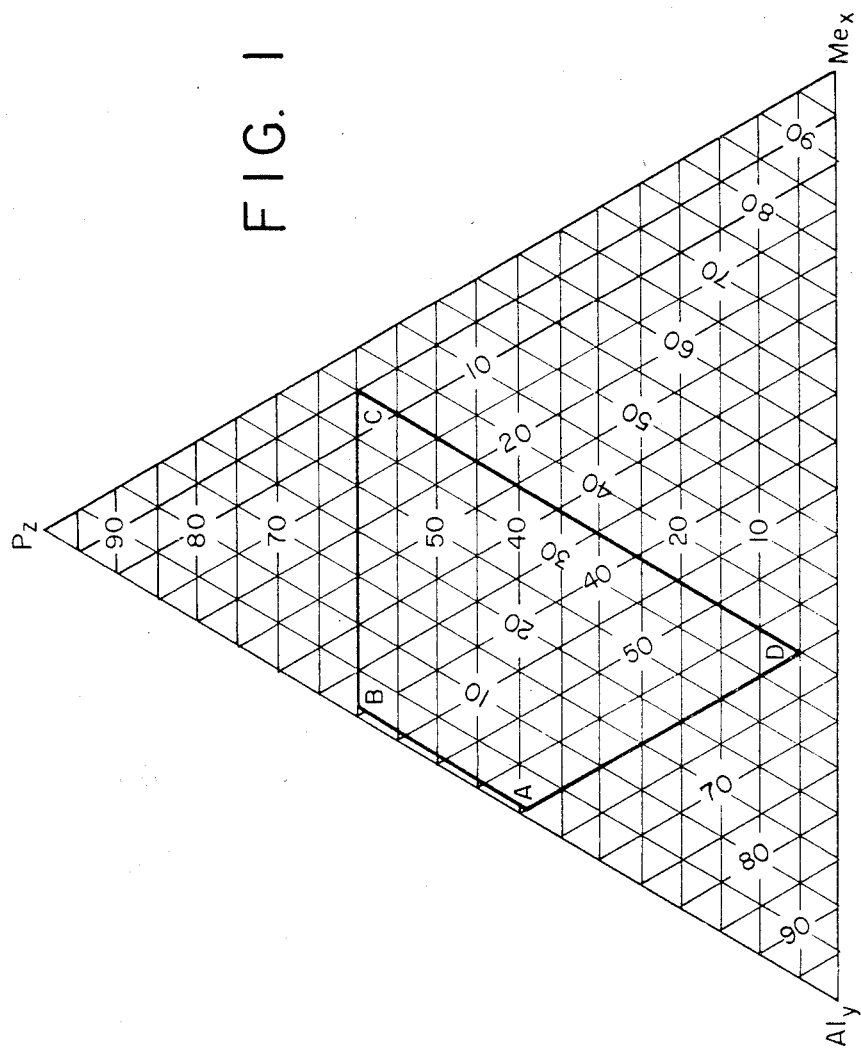
FIG. 1 is a ternary diagram wherein parameters relating to the instant compositions are set forth as mole fractions

There has now been discovered a novel class of framework-substituted crystalline microporous aluminophosphates in which the substituent metal is one of a mixture of two or more divalent metals of the group magnesium, manganese, zinc and cobalt, and which exhibit adsorption, ion-exchange and/or catalytic properties similar to the prior known aluminosilicate, aluminophosphate and silicoaluminophosphate molecular sieve compositions. Members of this novel class of compositions have a three-dimensional microporous crystal framework structure of $MO_2^{-2}$, $AlO_2^-$ and $PO_2^+$ tetrahedral units and have an essential empirical chemical composition, on an anhydrous basis, of:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides, said mole fractions being such that they are within the tetragonal compositional area defined by points A, B, C and D of the ternary diagram which is FIG. 1 of the drawings. The said points A, B, C and D representing the following values for "x", "y", and "z":

| Point | Mole Fraction | | |
|---|---|---|---|
| | x | y | z |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized in accordance with the novel process of the present invention, the minimum value of "m" in the formula above is 0.02. In a preferred sub-class of the metal aluminophosphates of this invention, the values of "x", "y" and "z" in the formula above are confined to those within the tetragonal compositional area defined by the points a, b, c and d of the ternary diagram which is FIG. 2 of the drawings, the said points a, b, c, and d representing the following values for "x", "y" and "z":

| Point | Mole Fraction | | |
|---|---|---|---|
| | x | y | z |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The metal aluminophosphates of this new class of compositions exhibit molecular sieving properties, and, in common with zeolitic aluminosilicates, are capable of reversibly adsorbing water and other molecular species. Many are capable of reversibly undergoing complete dehydration without loss or change in crystal structure. All of the as-synthesized compositions of this invention are capable of withstanding 350° C. calcination in air for extended periods, i.e. at least 2 hours, without becoming amorphous. While it is believed that the M, Al and P framework constituents are present in tetrahedral coordination with oxygen, it is theoretically possible that some minor fraction of these framework constituents are present in coordination with five or six oxygen atoms. It is not, moreover, necessarily the case that all of the M, Al and/or P content of any given synthesized product be a part of the framework in the aforesaid types of coordination with oxygen. Some of each constituent may be merely occluded or in some as yet undetermined form and may or may not be structurally significant.

Since the term "metal aluminophosphate" is somewhat cumbersome, particularly in view of the need for numerous repetitions thereof in describing the compositions of the present invention in this specification, the "short-hand" reference "MeAPO" is sometimes employed hereinafter. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The term "essential empirical chemical composition" is meant to include the crystal framework and can include any organic templating agent present in the pore system, but does not include alkali metal or other ions which can be present by virtue of being contained in the reaction mixture or as a result of post-synthesis ion-exchange. Such ionic species, when present, function primarily as charge-balancing ions for $AlO_2^-$ and/or $MO_2^{-2}$ tetrahedra not associated with $PO_2^+$ tetrahedra or an organic ion derived from the organic templating agent.

The aforesaid novel metal aluminophosphates are synthesized by hydrothermal crystallization from a reaction mixture containing reactive sources of the metal "M", alumina and phosphate, an organic templating, i.e., structure-directing, agent, preferably a compound of an element of Group VA of the Periodic Table, and optionally an alkali metal. The reaction mixture is placed in a sealed pressure vessel, preferably lined with an inert plastic material such as polytetrafluoroethylene and heated, preferably under autogenous pressure at a temperature between 100° C. and 225° C., and preferably between 100° C. and 200° C. until crystals of the metal aluminophosphate product are obtained, usually a period of from 4 hours to 2 weeks. The product is recovered by any convenient method such as centrifugation or filtration.

DETAILED DESCRIPTION OF THE INVENTION

Figure 3:
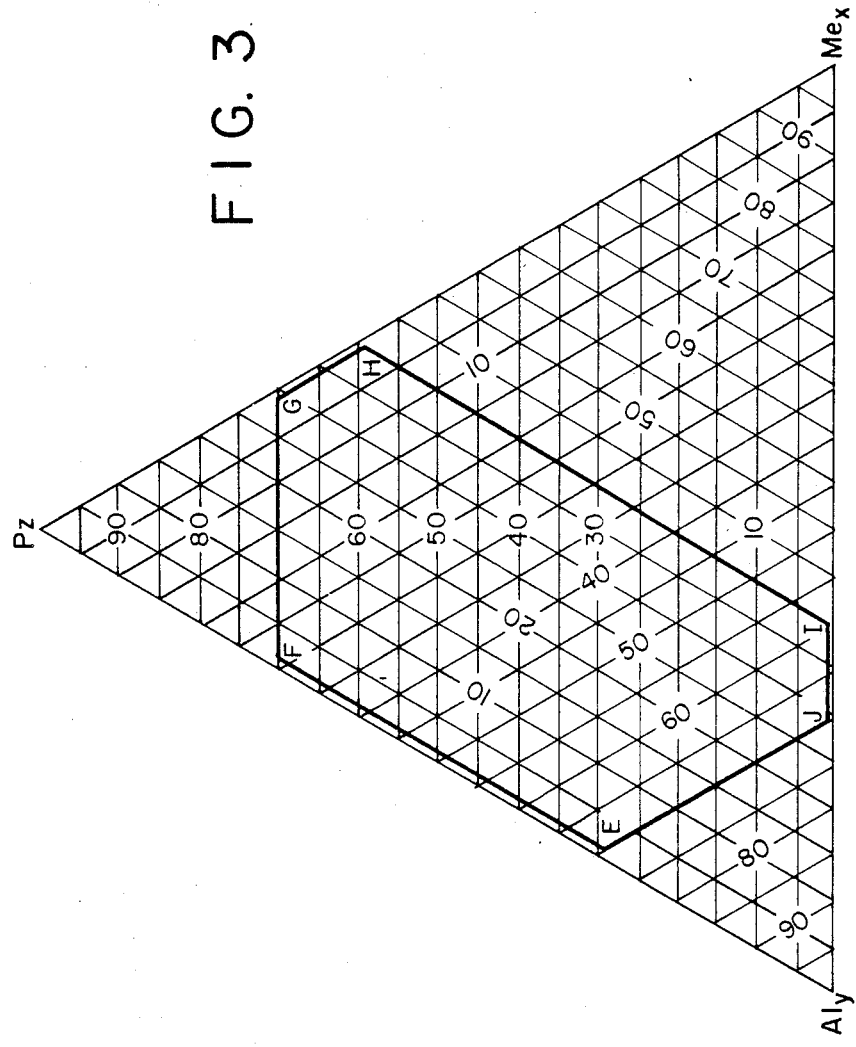
FIG. 3 is a ternary diagram wherein parametes relating to the reaction mixtures employed in the preparation of the compositions of this invention are set forth as mole fractions.

In synthesizing the MeAPO compositions of the present invention, it is preferred to employ a reaction mixture composition expressed in terms of molar ratios as follows:

$$aR:(M_xAl_yP_z)O_2:bH_2O$$

wherein "R" is is an organic templating agent; "a" has a value great enough to constitute an effective concentration of "R" and is within the range of >0 to 6; "b" has a value of from zero to 500, preferably 2 to 30; "M" represents a metal of the group zinc, magnesium, manganese and cobalt, "x", "y" and "z" represent the mole fractions, respectively, of "M", aluminum and phosphorus in the $(M_xAl_yP_z)O_2$ constituent, and each has a value of at least 0.01, and being within the hexagonal compositional areas defined by points E, F, G, H, I, and J which is shown in FIG. 3 of the drawings, the said points E, F, G, H, I, and J representing the following values for "x", "y" and "z":

| Point | Mole Fraction | | |
|---|---|---|---|
| | X | Y | Z |
| E | 0.01 | 0.70 | 0.29 |
| F | 0.01 | 0.29 | 0.70 |
| G | 0.29 | 0.01 | 0.70 |
| H | 0.40 | 0.01 | 0.59 |
| I | 0.40 | 0.59 | 0.01 |
| J | 0.29 | 0.70 | 0.01 |

In the foregoing expression of the reaction composition, the reactants are normalized with respect to a total of $(M+Al+P)=(x+y+z)=1.00$ mole, whereas in many of the working examples appearing hereinafter the reaction mixtures are expressed in terms of molar oxide ratios normalized to 1.00 mole of $P_2O_5$. This latter form is readily converted to the former form by routine calculations. Thus for example, in a reaction mixture expressed in terms of molar oxide ratios as $2TPAOH:0.4MgO:0.8Al_2O_3:P_2O_5:50H_2O$ the molar ratios of Mg, Al and P are 0.4Mg:1.6Al:2.0P, and $(Mg+Al+P)=4.0$. The mole fraction of x, y and z are computed by dividing each coefficient and the molar proportions of water and templating agent, by 4.0. This results in:

$2.0/4.0 TPAOH:(Mg_{0.4/4.0}Al_{1.6/4.0}P_{2.0/4.0})O_2 50/4.0-H_2O$ or $0.5TPAOH:(Mg_{0.1}Al_{0.4}P_{0.5})O_2:12.5H_2O$.

In forming the reaction mixture from which the present metal aluminophosphates are crystallized the organic templating agent can be any of those heretofore proposed for use in the synthesis of conventional zeolite aluminosilicates and microporous aluminophosphates. In general these compounds contain elements of Group VA of the Periodic Table of Elements, particularly nitrogen, phosphorus, arsenic and antimony, preferably N or P and most preferably N, which compounds also contain at least one alkyl or aryl group having from 1 to 8 carbon atoms. Particularly preferred nitrogen-containing compounds for use as templating agents are the amines and quaternary ammonium compounds, the latter being represented generally by the formula $R_4N^{30}$ wherein each R is an alkyl or aryl group containing from 1 to 8 carbon atoms. Polymeric quaternary ammonium salts such as $[(C_{14}H_{32}N_2)(OH)_2]_x$ wherein "x" has a value of at least 2 are also suitably employed. Both mono-, di- and tri-amines are advantageously utilized, either alone or in combination with a quaternary ammonium compound or other templating compound. Mixtures of two or more templating agents can either produce mixtures of the desired metal aluminophoshates or the more strongly directing templating species may control the course of the reaction with the other templating species serving primarily to establish the pH conditions of the reaction gel. Representative templating agents include tetramethylammonium, tetraethylammonium, tetrapropylammonium or tetrabutylammonium ions; di-n-propylamine; tripropylamine; triethylamine; triethanolamine; piperidine; cyclohexylamine; 2-methylpyridine; N,N-dimethylbenzylamine; N,N-dimethylethanolamine; choline; N,N'-dimethylpiperazine; 1,4-diazabicyclo(2,2,2,)octane; N-methyldiethanolamine, N-methylethanolamine; N-methylpiperidine; 3-methylpiperidine; N-methylcyclohexylamine; 3-methylpyridine; 4-methylpyridine; quinculidine; N,N'-dimethyl-1,4-diazabicyclo(2,2,2)octane ion; di-n-butylamine, neopentylamine; di-n-pentylamine; isopropylamine; t-butylamine; ethylenediamine; pyrolidine; and 2-imidazolidone. As will be readily apparent from the illustrative Examples set forth hereinafter, not every templating agent will direct the formation of every species of metal aluminophosphate (MeAPO), i.e., a single templating agent can, with proper manipulation of the reaction conditions, direct the formation of several MeAPO compositions, and a given MeAPO composition can be produced using several different templating agents.

The most suitable phosphorus source yet found for the present process is phosphoric acid, but organic phosphates such as triethyl phosphate have been found satisfactory, and so also have crystalline or amorphous aluminophosphates such as the $AlPO_4$ composition of U.S. Pat. No. 4,310,440. Organo-phosphorus compounds, such as tetrabutylphosphonium bromide do not, apparently serve as reactive sources of phosphorus, but these compounds do function as templating agents. Conventional phosphorus salts such as sodium metaphosphate, may be used, at least in part, as the phosphorus source, but are not preferred.

The preferred aluminum source is either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The metals zinc, cobalt, magnesium and manganese can be introduced into the reaction system in any form which permits the formation in situ of reactive divalent ions of the respective metals. Advantageously salts, oxides or hydroxides of the metals are employed such as cobalt chloride hexahydrate, alpha cobaltous iodide, cobaltous sulfate, cobalt acetate, cobaltous bromide, cobaltous chloride, zinc acetate, zinc bromide, zinc formate, zinc iodide, zinc sulfate heptahydrate, magnesium acetate, magnesium bromide, magnesium chloride, magnesium iodide, magnesium nitrate, magnesium sulfate, manganous acetate, manganous bromide, manganous sulfate, and the like.

While not essential to the synthesis of MeAPO compositions, it has been found that in general, stirring or other moderate agitation of the reaction mixture and/or seeding the reaction mixture with seed crystals of either the MeAPO species to be produced or a topologically similar aluminophosphate or aluminosilicate composition, facilitates the crystallization procedure.

After crystallization the MeAPO product is isolated and advantageously washed with water and dried in air. The as-synthesized MeAPO contains within its internal pore system at least one form of the templating agent employed in its formation. Most commonly the organic moiety is present, at least in part, as a charge-balancing cation as is generally the case with as-synthesized aluminosilicate zeolites prepared from organic-containing reaction systems. It is possible, however, that some or all of the organic moiety is an occluded molecular species in a particular MeAPO species. As a general rule the templating agent, and hence the occluded organic species, is too large to move freely through the pore system of the MeAPO product and must be removed by calcining the MeAPO at temperatures of 200° C. to 700° C. to thermally degrade the organic species. In a few instances the pores of the MeAPO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein and in the claims does not include the condition of the MeAPO phase wherein the organic moiety occupying the intracrystalline pore system as a result of the hydrothermal crystallization process has been reduced by post-synthesis treatment such that the value of "m" in the composition formula

has a value of less than 0.02. The other symbols of the formula are as defined hereinabove. In those preparations in which an aluminum alkoxide is employed as the source of aluminum, the corresponding alcohol is necessarily present in the reaction mixture since it is a hydrolysis product of the alkoxide. It has not been determined whether this alcohol participates in the syntheses process as a templating agent. For the purposes of this application, however, this alcohol is arbitrarily omitted from the class of templating agents, even if it is present in the as-synthesized MeAPO material.

Since the present MeAPO compositions are formed from $AlO_2$, $PO_2$ and $MO_2$ tetrahedral units which, respectively, have a net charge of $-1$, $+1$, and $-2$, the matter of cation exchangeability is considerably more complicated than in the case of zeolitic molecular sieves in which, ideally, there is a stoichiometric relationship between $AlO_2$ tetrahedra and charge-balancing cations. In the MeAPO compositions, an $AlO_2^-$ tetrahedron can be balanced electrically either by association with a $PO_2^+$ tetrahedron or a simple cation such as an alkali metal cation, a cation of the metal "M" present in the reaction mixture, or an organic cation derived from the templating agent. Similarly an $MO_2^{-2}$ tetrahedron can be balanced electrically by association with $PO_2+$ tetrahedra, a cation of the metal "M", organic cations derived from the templating agent, or other divalent or polyvalent metal cations introduced from an extraneous source.

It has also been postulated that non-adjacent $AlO_2^-$ and $PO_2+$ tetrahedral pairs can be balanced by $Na^+$ and $OH^-$ respectively [Flanigen and Grose, Molecular Sieve Zeolites-I, ACS, Washington, DC (1971)].

In any event, all of the MeAPO compositions of the present invention examined to date have exhibited cation-exchange capacity, in some cases to a significant degree, when analyzed using ion-exchange techniques heretofore employed with zeolitic aluminosilicates. All have uniform pore diameters which are inherent in the lattice structure of each species and which are at least about 3A in diameter. Ion exchange is ordinarily possible only after the organic moiety present as a result of synthesis has been removed from the pore system. Dehydration to remove water present in the as-synthesized MeAPO compositions can usually be accomplished, to some degree at least, in the usual manner without removal of the organic moiety, but the absence of the organic species greatly facilitates adsorption and desorption procedures. As illustrated hereinafter, the MeAPO materials have various degrees of hydrothermal and thermal stability, some being quite remarkable in this regard, and function well as molecular sieve adsorbents and hydrocarbon conversion catalysts or catalyst bases.

The invention is illustrated by the following Examples. Unless otherwise stated, in each example wherein a hydrated aluminum oxide is specified as a reagent, the reagent employed was a commercially available pseudo-boehmite phase containing either 75.1 wt. % $Al_2O_3$ and 24.9 wt. % water or 74.2 wt. % $Al_2O_3$ and 25.8 wt. % water, the former being designated hydrated aluminum oxide (I) and the latter, hydrated aluminum oxide (II). Also in each example the stainless steel reaction vessel utilized was lined with the inert plastic material, polytetrafluoroethylene, to avoid contamination of the reaction mixture. In general, the final reaction mixture from which each MeAPO composition is crystallized is prepared by forming mixtures of less than all of the reagents and thereafter incorporating into these mixtures addition reagents either singly or in the form of other intermediate mixtures of two or more reagents. In some instance the reagents admixed retain their identity in the intermediate mixture and in other cases some or all of the reagents are involved in chemical reactions to produce new reagents. The term "mixture" is applied in both cases. Further, unless otherwise specified, each intermediate mixtures as well as the final reaction mixture was stirred until substantially homogeneous.

Where reaction products were subjected to X-ray analysis, the X-ray patterns were obtained using standard X-ray powder diffraction techniques. The radiation source was a high-intensity, copper target, X-ray tube operated at 50 Kv and 40 ma. The diffraction pattern from the copper K radiation and graphite monochromator is suitably recorded by an X-ray spectrometer scintillation counter, pulse height analyzer and strip chart recorder. Flat compressed powder samples are scanned at 2° (2 theta) per minute, using a two second time constant. Interplanar spacings (d) in Angstrom units are obtained from the position of the diffraction peaks expressed as $2\theta$ where $\theta$ is the Bragg angle as observed on the strip chart. Intensities were determined from the heights of diffraction peaks after subtracting background, "$I_o$" being the intensity of the strongest line or peak, and "I" being the intensity of each of the other peaks.

As will be understood by those skilled in the art the determination of the parameter 2 theta is subject to both human and mechanical error, which in combination, can impose an uncertainty of about ±0.4° on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, ms, m, w and vw which represent very strong, strong, medium strong, medium, weak and very weak respectively.

In certain instances hereinafter in the illustrative examples, the purity of a synthesized product is assessed with reference to its X-ray powder diffraction pattern. Thus, for example, if a sample of MAPO-5 is stated to be "pure MAPO-5", it is intended only that the X-ray pattern of the sample is free of lines attributable to crystalline impurities, not that there are no amorphous materials present.

EXAMPLE 1

(Preparation of MAPO-5)

(a) An initial mixture was prepared by combining 46.2 grams of 85% orthophosporic acid ($H_3PO_4$) and 92.6 grams of water, to which was added 24.9 grams of a hydrated aluminum oxide (I). A solution prepared by dissolving 7.2 grams of magnesium acetate tetrahydrate ($Mg(CH_3CO_2)_2 \cdot 4 H_2O$) in 25.1 grams of $H_2O$ was added to this initial mixture and to the resulting mixture was added 23.4 grams of N,N-diethyl-ethanolamine ($C_6H_{15}NO$) to form the final reaction mixture having a composition in terms of molar oxide ratios of:

1.0$C_6H_{15}NO$:0.167$MgO$:0.917$Al_2O_3$:1.0$P_2O_5$:39.8-$H_2O$:0.33$CH_3COOH$.

The reaction mixture was placed in a sealed stainless steel pressure vessel and heated in an oven at 200° C. for 24 hours. The solids were recovered by filtration, washed with water, and dried in air at room temperature. A portion of the solids that passed through a 60 mesh screen was subjected to X-ray and chemical analysis. The chemical composition was found to be 33.2 wt. % $Al_2O_3$, 49.4 wt. % $P_2O_5$, 2.6 wt. % $MgO$, 5.4 wt. % C and 1.08 wt. % N. Expressed in terms of molar oxide ratios, the composition was:

0.22$C_6H_{15}NO$:0.19$MgO$:0.94$Al_2O_3$:1.00$P_2O_5$:0.78-$H_2O$, which corresponds to an empirical chemical composition (anhydrous basis) of:

0.05$C_6H_{15}NO$:($Mg_{0.05}Al_{0.46}P_{0.49}$)$O_2$

The X-ray powder diffraction pattern of the analyzed sample was characterized by the following data:

TABLE A

| 2θ | d (A) | 100 I/I$_o$ |
| --- | --- | --- |
| 7.3 | 12.1 | 83 |
| 12.8 | 6.92 | 10 |
| 14.8 | 5.99 | 21 |
| 19.6 | 4.53 | 56 |
| 21.0 | 4.23 | 60 |
| 22.3 | 3.99 | 100 |
| 24.7 | 3.60 | 6 |
| 25.7 | 3.47 | 34 |
| 28.9 | 3.09 | 19 |
| 29.8 | 3.00 | 20 |
| 33.4 | 2.683 | 5 |
| 34.3 | 2.614 | 16 |
| 36.8 | 2.442 | 3 |
| 37.7 | 2.386 | 12 |
| 42.1 | 2.146 | 3 |
| 47.4 | 1.918 | 5 |
| 55.3 | 1.661 | 3 |

(b) A portion of the solids from part (a) supra was calcined at 600° C. for 3¼ hours, and then subjected to X-ray analysis. The X-ray powder diffraction pattern obtained was essentially identical with the pattern of TABLE A.

(c) A portion of the calcined material of part (b) supra was utilized in adsorption capacity studies using a standard McBain-Bakr gravimetric adsorption apparatus. Measurements were made on a sample having a particle size of −200 mesh after activation at 350° C. The following data were obtained.

| Adsorbate | Kinetic Diameter, A | Pressure Torr | Temp., °C. | Wt. % Adsorbed |
| --- | --- | --- | --- | --- |
| $O_2$ | 3.46 | 102 | −183 | 15.4 |
| $O_2$ | 3.46 | 706 | −183 | 18.0 |
| Cyclohexane | 6.0 | 74 | 25 | 10.5 |
| n-butane | 4.3 | 705 | 24 | 7.4 |
| Neopentane | 6.2 | 701 | 24 | 7.2 |
| $H_2O$ | 2.65 | 4.6 | 24 | 17.3 |
| $H_2O$ | 2.65 | 22 | 24 | 26.3 |

EXAMPLE 2

(Preparation of MAPO-5)

A reaction mixture having a composition expressed in molar oxide ratios of:

1.0$CH_9H_{21}N$:0.4$MgO$:0.8$Al_2O_3$:1.0$P_2O_5$:40$H_2O$ was prepared as follows: A solution was prepared by combining 46.1 grams of 85% orthophosphoric acid ($H_3PO_4$) with 120.6 grams of water and 3.2 grams of magnesium oxide (MgO), and then admixed with 22.0 grams of a hydrated aluminum oxide (II) and to the resulting mixture was added 28.7 grams of tripropylamine ($C_9H_{21}N$). The reaction mixture was placed in a sealed stainless steel pressure vessel and crystallized at 150° C. for 24 hours. The solids were recovered by filtration, washed with water and dried at room temperature. By X-ray analysis, the solids were found to comprise MAPO-5 in combination with a minor impurity phase. The MAPO-5 constituent had a powder diffraction pattern essentially the same as set forth in TABLE A, above.

EXAMPLE 3

(Preparation of MAPO-5)

A mixture was prepared by combining 46.2 grams of 85% orthophosphoric acid ($H_3PO_4$) and 36.7 grams of water, to which was added 24.9 grams of a hydrated aluminum oxide (I). A solution prepared by dissolving 7.2 grams of magnesium acetate tetrahydrate ($Mg(CH_3CO_2)_2 \cdot 4H_2O$) in 20.1 grams of $H_2O$ was added to this mixture and the resulting mixture combined with 101.7 grams of aqueous 40% tetrapropylammonium hydroxide (TPAOH) to form the final reaction mixture having a composition in terms of molar oxide ratios of:

1.0  TPAOH:0.167$MgO$:0.917$Al_2O_3$:1.0$P_2O_5$:39.8-$H_2O$:0.33$CH_3COOH$

The reaction mixture was placed in a sealed stainless steel pressure vessel and heated in an oven at 150° C. at autogenous pressure for 72 hours. The solids were recovered by filtration, washed with water, and dried in air at room temperature. The portion of the solid that passed through a 60 mesh screen was impure by X-ray analysis, but the major phase had an X-ray powder diffraction pattern essentially identical to that in Example 1(a).

EXAMPLE 4

(Preparation of MAPO-5)

MAPO-5 was prepared using 2-methylpyridine ($C_6H_7N$) using the following procedure: 138.8 grams of an aqueous orthophosphoric and solution containing 39.3 grams $H_3PO_4$ was mixed with 24.9 grams of a hydrated aluminum oxide (I). A solution prepared by dissolving 7.2 grams of magnesium acetate tetrahydrate ($Mg(CH_3CO_2)_2 \cdot 4H_2O$) in 25.2 grams of $H_2O$ was added to this mixture and the resulting mixture combined with 18.6 grams of 2-methylpyridine. The composition of the final reaction mixture in terms of molar oxide ratios was:

1.0C$_6$H$_7$N:0.167MgO:0.917Al$_2$O$_3$:1.0P$_2$O$_5$:39.8-H$_2$O:0.33CH$_3$COOH

The reaction mixture was placed in a sealed stainless steel pressure vessel and heated in an oven at 150° C. for 24 hours. The solid product was recovered by filtration, washed with water and dried in air at room temperature. A portion of the solid was subjected to X-ray and chemical analysis. The X-ray powder diffraction pattern obtained was essentially identical to that in TABLE A of Example 1(a). Chemical analysis showed 32.3 wt. % Al$_2$O$_3$, 48.4 wt. % P$_2$O$_5$, 2.3 wt. % MgO, 7.7 wt. % C, 1.6 wt. % N, and 17.2 wt. % LOI (loss on ignition at 1000° C.) giving a product composition in molar oxide ratios of:

0.32C$_6$H$_7$N:0.17MgO:0.93Al$_2$O$_5$:1.00P$_2$O$_5$:1.2 H$_2$O

In terms of moles of organic constituents per average mole to TO$_2$ units, i.e. the essential empirical formula (anhydrous basis), the composition was 0.08C$_6$H$_7$N:(Mg$_{0.04}$Al$_{0.46}$P$_{0.50}$)O$_2$.

EXAMPLES 5–11

(Preparations of MAPO-5)

Using a procedure similar to that described in Example 3, above, seven reaction mixtures, each employing a different organic templating agent, "R", were formulated and crystallized. The composition of each reaction mixture in terms of molar oxide ratios was:

1.0R:aMgO:bAl$_2$O$_3$:P$_2$O$_5$:cH$_2$O:2aCH$_3$COOH.

The values of a, b and c, the specific templating agents, the reaction time and temperature in each case are given in tabular form below:

| Ex. # | R | a | b | c | Reaction Temp., °C. | Reaction Time, hr |
|---|---|---|---|---|---|---|
| 5 | Tetraethyl ammonium hydroxide | 0.4 | 0.8 | 39.6 | 200 | 72 |
| 6 | Diiso-propylamine | 0.167 | 0.917 | 39.8 | 200 | 24 |
| 7 | Cyclohexyl amine | 0.167 | 0.917 | 39.8 | 150 | 24 |
| 8 | Triethyl-amine | 0.167 | 0.917 | 39.8 | 150 | 168 |
| 9 | N—methyl-butylamine | 0.167 | 0.917 | 39.8 | 150 | 24 |
| 10 | N—ethyl-butylamine | 0.40 | 0.80 | 39.6 | 150 | 24 |
| 11 | Dibutyl-amine | 0.40 | 0.80 | 39.6 | 200 | 24 |

X-ray analysis of the solids products in each case indicated the presence of MAPO-5.

The species MAPO-5 as referred to herein is a magnesium aluminophosphate material having a three-dimensional microporous crystal framework structure of PO$_2^+$, AlO$_2^-$ and MgO$^{-2}$ tetrahedral units, and whose essential empirical chemical composition on an anhydrous basis is:

mR:(Mg$_x$Al$_y$P$_z$)O$_2$ wherein "R" represents at least one organic templating agent present in the intracrystalline pore system; "m" represents the moles of "R" present per mole of (Mg$_x$Al$_y$P$_z$)O$_2$ and has a value of from zero to 0.3, "x", "y" and "z" represent respectively, the mole fractions of magnesium, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said magnesium aluminophosphate having a characteristic X-ray powder diffraction pattern which contains at least the d-spacings set forth below in Table I. In the form as synthesized in accordance with the process of this invention, "m" has a value of from 0.02 to 0.3.

TABLE I

| 2θ | d (A) | Relative Intensity |
|---|---|---|
| 7.3–7.4 | 12.1–11.9 | m–vs |
| 14.7–14.9 | 6.03–5.95 | vw–w |
| 19.5–19.8 | 4.55–4.48 | w–s |
| 20.9–21.1 | 4.25–4.21 | m–s |
| 22.2–22.5 | 4.00–3.95 | w–vs |
| 25.7–26.0 | 3.47–3.43 | w–m |

All of the as-synthesized MAPO-5 compositions for which X-ray powder diffraction data have presently been obtained have patterns which are within the generalized pattern of Table II below:

TABLE II

| 2θ | d, (A) | 100 × I/Io |
|---|---|---|
| 7.3–7.4 | 12.1–11.9 | 49–100 |
| 12.7–12.9 | 6.97–6.86 | 7–20 |
| 14.7–14.9 | 6.03–5.95 | 10–24 |
| 19.5–19.8 | 4.55–4.48 | 27–74 |
| 20.9–21.1 | 4.25–4.21 | 34–57 |
| 22.2–22.5 | 4.00–3.95 | 28–100 |
| 24.5–24.8 | 3.63–3.59 | 2–11 |
| 25.7–26.0 | 3.47–3.43 | 13–33 |
| 28.8–29.1 | 3.10–3.07 | 9–22 |
| 29.8–30.1 | 3.00–2.97 | 14–20 |
| 33.4–33.7 | 2.683–2.660 | 5–7 |
| 34.3–34.6 | 2.614–2.592 | 10–18 |
| 36.7–37.0 | 2.449–2.430 | 1–4 |
| 37.6–37.8 | 2.392–2.380 | 2–13 |
| 47.3–47.8 | 1.922–1.903 | 2–6 |
| 55.2–55.8 | 1.664–1.647 | 2–3 |

EXAMPLE 12

(Preparation of MAPO-11)

A solution was prepared by combining 46.1 grams of 85% orthophosphoric acid (H$_3$PO$_4$), 120.6 grams of water, and 3.2 grams of magnesium oxide (MgO). To this solution was added 22.0 grams of a hydrated aluminum oxide (II), and to the resulting mixture was added 20.2 grams of diisopropylamine (C$_6$H$_{15}$N). The composition of the final reaction mixture in molar oxide ratios was:

1.0C$_6$H$_{15}$N:0.4MgO:0.8Al$_2$O$_3$:1.0P$_2$O$_5$:40H$_2$O.

The reaction mixture was placed in a sealed stainless steel pressure vessel and heated in an oven at 200° C. for 24 hours. The solid product was recovered by filtration, washed with water, and dried in air at room temperature. A portion of the solids was subjected to X-ray analysis. This solid was inpure but the major phase had an X-ray powder diffraction pattern characterized by the following data:

TABLE B

| 2θ | d, (A) | 100 × I/Io |
|---|---|---|
| 8.2 | 10.78 | 44 |
| 9.6 | 9.21 | 65 |
| 13.2 | 6.71 | 23 |

TABLE B-continued

| 2θ | d, (A) | 100 × I/Io |
|---|---|---|
| 15.8 | 5.61 | 44 |
| 19.1 | 4.65 | 7 |
| 20.4 | 4.35 | 71 |
| 21.2 | 4.19 | 69 |
| 22.2 | 4.00 | 71 |
| 22.5 | 3.95 | 57 |
| 22.8 | 3.90 | 67 |
| 23.3 | 3.82 | 100 |
| 24.5 | 3.63 | 8 |
| 24.8 | 3.59 | 13 |
| 26.5 | 3.36 | 41 |
| 28.2 | 3.16 | 12 |
| 28.7 | 3.11 | 25 |
| 29.5 | 3.03 | 11 |
| 31.6 | 2.83 | 14 |
| 32.8 | 2.73 | 29 |
| 34.2 | 2.62 | 11 |
| 36.3 | 2.47 | 8 |
| 37.6 | 2.39 | 17 |
| 44.7 | 2.03 | 8 |
| 50.7 | 1.80 | 6 |

EXAMPLE 13

(Preparation of MAPO-11)

(a) A reaction mixture was prepared by first combining 46.2 grams of 85% orthophosphoric acid and 91.5 grams of water, to which was added 25.2 grams of a hydrated aluminum oxide (II). A solution prepared by dissolving 7.2 grams of magnesium acetate tetrahydrate ($Mg(CH_3CO_2)_2 \cdot 4H_2O$) in 25.5 grams of $H_2$) was added to the first prepared mixture and thereafter 20.2 grams of diisopropylamine ($C_6H_{15}N$) was added to form the final reaction mixture which had a composition in terms of molar oxide ratios of:

$1.0C_6H_{15}N:0.167MgO:0.917Al_2O_3:1.0P_2O_5:39.8-H_2O:0.33CH_3COOH$.

The reaction mixture was placed in a sealed stainless steel pressure vessel and heated at 200° C. for 73 hours. The solid product was recovered by filtration, washed with water and dried in air at room temperature. A portion of the solid was subjected to X-ray and chemical analysis. This sample had an X-ray powder diffraction pattern essentially identical to that of the major phase in Example 12. Chemical analysis showed 33.9 wt.% $Al_2O_3$, 52.7 wt.% $P_2O_5$, 2.5 wt.% MgO, 5.3 wt.% C, 1.1 wt.% N, and 9.1 wt.% LOI, giving a product composition in molar oxide ratios of:

$0.20C_6H_{15}N:0.17MgO:0.90Al_2O_3:1.00P_2O_5:0.25H_2O$ or in terms of moles of diisopropylamine per average $TO_2$ unit,

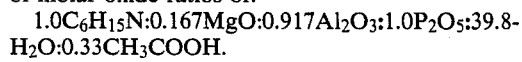
$0.05C_6H_{15}N:(Mg_{0.042}Al_{0.453}P_{0.505})O_2$.

(b) A portion of this product was calcined in air at 600° C. for 66 hours. The calcined product exhibited an X-ray powder diffraction pattern essentially identical to that set forth in Examaple 14(b) infra.

EXAMPLE 14

(Preparation of MAPO-11)

(a) A reaction mixture identical to that in Example 13, supra was placed in a sealed stainless steel pressure and heated at 200° C. for 24 hours. The solid product was recovered by filtration, washed with water and dried in air at room temperature. A portion of the solid that passed through a 60 mesh screen was subjected to X-ray analysis. This solid had an X-ray powder diffraction pattern essentially identical to that of the major phase in Example 12.

(b) A portion of the solids of part (a) was heated from 100° C. to 600° C. in 4 hours, held at 600° C. for 72 hours, and then cooled to room temperature. This calcined solid exhibited in X-ray powder diffraction pattern characterized by the following data:

TABLE C

| 2θ | d, (A) | 100 × I/Io |
|---|---|---|
| 8.1 | 10.9 | 100 |
| 9.6 | 9.21 | 83 |
| 13.2 | 6.71 | 26 |
| 16.0 | 5.54 | 58 |
| 20.4 | 4.35 | 32 |
| 21.4 | 4.15 | 79 |
| 22.4 | 3.97 | 58 |
| 23.0 | 3.87 | 42 |
| 23.4 | 3.80 | 53 |
| 24.5 | 3.63 | 4 |
| 25.1 | 3.55 | 4 |
| 25.5 | 3.49 | 23 |
| 28.2 | 3.16 | 2 |
| 29.0 | 3.08 | 11 |
| 29.6 | 3.02 | 8 |
| 31.9 | 2.805 | 8 |
| 32.9 | 2.722 | 13 |
| 34.2 | 2.622 | 4 |
| 34.8 | 2.578 | 6 |
| 36.4 | 2.468 | 8 |
| 38.0 | 2.368 | 9 |
| 38.4 | 2.344 | Shoulder |

(c) A second portion of the original solids from part (a) was placed directly into a furnace at 600° C., held at 600° C. for 72 hours, then cooled to room temperature in approximately 0.1 hour. This calcined material exhibited an X-ray powder diffraction pattern characterized by the following data:

TABLE D

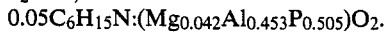

| 2θ | d, (A) | 100 × I/I_o |
|---|---|---|
| 8.0 | 11.0 | 38 |
| 9.8 | 9.02 | 94 |
| 11.7 | 7.55 | 7 |
| 12.8 | 6.91 | 50 |
| 13.7 | 6.46 | 8 |
| 14.7 | 6.04 | 6 |
| 16.1 | 5.51 | 100 |
| 19.5 | 4.56 | 16 |
| 19.9 | 4.46 | 50 |
| 20.7 | 4.28 | 9 |
| 21.8 | 4.07 | 88 |
| 22.2 | 4.01 | 53 |
| 22.5 | 3.96 | 65 |
| 23.5 | 3.78 | 69 |
| 24.0 | 3.71 | 13 |
| 24.3 | 3.66 | 15 |
| 25.8 | 3.45 | 35 |
| 26.7 | 3.33 | 13 |
| 27.2 | 3.27 | 14 |
| 27.7 | 3.22 | 26 |
| 28.5 | 3.13 | 9 |
| 29.6 | 3.02 | 22 |
| 29.8 | 3.00 | 31 |
| 30.4 | 2.94 | 17 |
| 31.8 | 2.817 | 8 |
| 32.7 | 2.742 | 33 |
| 34.0 | 2.635 | 8 |
| 34.5 | 2.602 | 5 |
| 35.5 | 2.528 | 12 |
| 35.8 | 2.510 | 14 |
| 37.2 | 2.415 | 9 |
| 38.7 | 2.327 | 11 |

The observed differences in the patterns of parts (a) and (c) are believed to be due to differences in the degree of hydration of the samples when analyzed, rather than the method of calcination.

EXAMPLE 15

(Preparation of MAPO-11)

A final reaction mixture having a composition in terms of molar oxide ratios of:

$1.0C_6H_{15}N:0.167MgO:0.917Al_2O_3:1.25P_2O_5:40H_2O$ was formed by combining a first mixture prepared by admixing 25.2 grams of a hydrated aluminum oxide (I) with 132.7 grams of an aqueous orthophosphonic acid solution containing 39.27 grams of $H_3PO_4$, with a solution prepared by dissolving 0.8 grams of magnesium metal chips in 11.6 grams of 85% orthophosphoric and, thereafter adding 20.2 grams of diisopropylamine. The final reaction mixture was placed in a sealed stainless steel reactor and heated at 150° C. for 168 hours. The solids were recovered by filtration, washed with water and dried in air at room temperature. A portion of the solids was subjected to X-ray analysis and found to have an X-ray powder diffraction pattern essentially identical to that of the major phase in Example 12.

EXAMPLE 16

(Preparation of MAPO-11)

A reaction mixture containing a relatively high concentration of magnesium was prepared by first combining 46.2 grams of 85% orthophosphoric acid and 52.0 grams of water, and adding 18.1 grams of a hydrated aluminum oxide (I). A solution prepared by dissolving 28.6 grams of magnesium acetate tetrahydrate in 60.2 grams of $H_2O$ was added to this first mixture, and to the resulting mixture was then added 20.2 grams of diisopropylamine ($C_6H_{15}N$). The composition of the final reaction mixture in molar oxide ratios was:

wt.% $Al_2O_3$, 52.5 wt.% $P_2O_5$, 2.4 wt.% MgO, 5.2 wt.% C, 1.0 wt.% N, and 9.9 wt.% LOI, giving a product composition in terms of molar oxide ratios of:

$0.20C_6H_{15}N:0.16MgO:0.91Al_2O_3:1.0P_2O_5:0.39H_2O$, or in terms of moles of diisopropylamine per average mole of $TO_2$ units:

$0.05C_6H_{15}N:(Mg_{0.04}Al_{0.46}P_{0.50})O_2:0.10H_2O$.

(b) A portion of the solid from part (a) was calcined at 600° C. for 64 hours. The calcined solid exhibited an X-ray powder diffracton pattern essentially identical to that of TABLE D in Example 14.

(c) Adsorption capacities were measured on a portion of the calcined solid of part (b) using a standard McBain-Bakr gravimetric adsorption apparatus. The following data was obtained on a sample activated at 350° C.

| Adsorbate | Kinetic Diameter, A | Pressure, Torr | Temp., °C. | Wt. % Absorbed |
|---|---|---|---|---|
| $O_2$ | 3.46 | 102 | −183 | 6.6 |
| $O_2$ | 3.46 | 706 | −183 | 7.2 |
| Xenon | 4.0 | 751 | 24 | 8.7 |
| n-butane | 4.3 | 705 | 24 | 2.9 |
| Cyclohexane | 6.0 | 74 | 25 | 1.5 |
| Neopentane | 6.2 | 701 | 24 | 0.3 |
| $H_2O$ | 2.65 | 4.6 | 24 | 12.6 |
| $H_2O$ | 2.65 | 22 | 24 | 14.3 |

(d) 4.93 grams of the calcined product of part (b) was stirred with 150.1 grams of water in a polypropylene beaker. The pH of this mixture was adjusted to 3.5 with dilute aqueous HCl and the mixture was stirred for 1 hour, during which time the pH increased to 3.7. The pH was adjusted to 3.5

$1.0C_6H_{15}N:0.667MgO:0.667Al_2O_3:1.0P_2O_5:39.3H_2O:1.33CH_3COOH$.

The reaction mixture was heated in a sealed stainless steel reactor at 150° C. for 72 hours. The solids were recovered by filtration, washed with water and dried in air at room temperature. X-ray analysis of a portion of the solids revealed that the product was impure, but the major phase had an X-ray powder diffraction pattern essentially identical to the major phase in Example 12.

EXAMPLE 17

(Preparation of MAPO-11)

(a) A mixture was prepared by combining 646.0 grams of water and 174.3 grams of a hydrated aluminum oxide (I) to which was added 323.2 grams of 85% orthophosphoric acid. A solution prepared by dissolving 50.1 grams of magnesium acetate tetrahydrate in 175.0 grams of $H_2O$ was added to this initial mixture, and to the resulting mixture 142.0 grams of diisopropylamine ($C_6H_{15}N$) was added to form the final reaction mixture which had a composition in terms of molar oxide ratios of:

$1.0C_6H_{15}N:0.167MgO:0.917Al_2O_3:1.00P_2O_5:39.8H_2O:0.33CH_3COOH$.

The reaction mixture was placed in a sealed stainless steel reactor and heated at 205° C. for 72 hours. The solids were recovered by filtration, washed with water, and dried in air at room temperature. A portion of the solids was subjected to X-ray and chemical analysis. The solid had an X-ray powder diffraction pattern essentially identical to that of the major phase in Example 12. Chemical analysis showed the sample to contain 34.4 and the mixture stood 10 minutes. A sample of the solution phase isolated by filtration and analyzed chemically was found to contain 1.1 ppm Al, 11.3 ppm Mg, and 14.3 ppm P. These concentrations indicated that, of the starting solid, 0.02 wt.% Al, 2.5 wt.% Mg, and 0.2 wt.% P had dissolved in the solution phase. The treated solid phase exhibited an X-ray diffraction powder pattern essentially identical to that of TABLE D in Example 14. Chemical analysis of the solid phase showed 33.6 wt.% $Al_2O_3$, 51.2 wt.% $P_2O_5$, 2.4 wt.% MgO, and 12.3 wt.% LOI at 1000° C.

EXAMPLES 18-22

(Preparation of MAPO-11)

MAPO-11 was found to be produced from reaction systems containing five additional amine templating agents. In each case a procedure similar to that of Example 13 was employed to prepare a reaction mixture having a composition in terms of molar oxide ratios of:

$1.0R:aMgO:bAl_2O_3:P_2O_5:cH_2O:2aCH_3COOH$.

Specifics of the individual experiments are set forth in tabular form below:

| Ex. | R | a | b | c | Reaction Temp., °C. | Reaction Time, hr |
|---|---|---|---|---|---|---|
| 18 | tripropylamine | 0.167 | 0.917 | 40 | 200 | 72 |
| 19 | N-methylbutylamine | 0.167 | 0.917 | 40 | 150 | 168 |
| 20 | dibutylamine | 0.4 | 0.8 | 40 | 150 | 24 |
| 21 | N-ethylbutylamine | 0.167 | 0.917 | 40 | 200 | 24 |
| 28 | di-n-propylamine | 0.167 | 0.917 | 40 | 200 | 24 |

X-ray analysis established the production of MAPO-11 in each case.

The species MAPO-11 as referred to herein is a magnesium aluminophosphate material having a three-dimensional microporous crystal framework structure of $PO_2^+$, $AlO_2^-$ and $MgO^{-2}$ tetrahedral units, and whose essential empirical chemical composition on an anhydrous basis is:

$$mR:(Mg_xAl_yP_z)O_2$$

wherein "R" represents at least one organic templating agent present in the intracrystalline pore system; "m" represents the moles of "R" present per mole of $(Mg_xAl_yP_z)O_2$ and has a value of from zero to 0.3, "x", "y" and "z" represent respectively, the mole fractions of magnesium, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said magnesium aluminophosphate having a characteristic X-ray powder diffraction pattern which contains at least the d-spacings set forth below in Table III. In the form as synthesized in accordance with the process of this invention, "m" has a value of from 0.02 to 0.3.

TABLE III

| $2\theta$ | d,(A) | Relative Intensity |
|---|---|---|
| 7.9–8.2 | 11.2–10.8 | w-m |
| 9.3–9.6 | 9.51–9.21 | m-s |
| 20.9–21.4 | 4.25–4.15 | s-vs |
| 21.9–22.2 | 4.06–4.00 | s |
| 22.2–22.5 | 4.00–3.95 | m-s |
| 23.0–23.4 | 3.87–3.80 | s-vs |

All of the as-synthesized MAPO-11 compositions for which X-ray powder diffraction data have presently been obtained have patterns which are within the generalized pattern of Table IV below:

TABLE IV

| $2\theta$ | d,(A) | $100 \times I/I_o$ |
|---|---|---|
| 7.9–8.2 | 11.2–10.8 | 22–44 |
| 9.3–9.6 | 9.51–9.21 | 34–65 |
| 13.0–13.2 | 6.81–6.71 | 15–23 |
| 15.5–16.0 | 5.72–5.54 | 29–44 |
| 18.8–19.2 | 4.72–4.62 | 5–13 |
| 20.1–20.4 | 4.42–4.35 | 37–71 |
| 20.9–21.4 | 4.25–4.15 | 69–100 |
| 21.9–22.2 | 4.06–4.00 | 56–71 |
| 22.2–22.5 | 4.00–3.95 | 46–57 |
| 22.5–22.8 | 3.95–3.90 | 56–69 |
| 23.0–23.3 | 3.87–3.82 | 72–100 |
| 24.2–24.5 | 3.68–3.63 | shoulder |
| 24.6–25.1 | 3.62–3.55 | 10–13 |
| 26.2–26.5 | 3.40–3.36 | 30–41 |
| 27.9–28.2 | 3.20–3.18 | shoulder |
| 28.4–29.0 | 3.14–3.08 | 16–25 |
| 29.2–29.5 | 3.06–3.03 | 9–12 |
| 31.3–31.9 | 2.858–2.805 | 10–14 |
| 32.5–32.9 | 2.755–2.722 | 16–29 |
| 34.0–34.8 | 2.637–2.578 | 7–11 |
| 36.1–36.4 | 2.488–2.468 | 6–8 |
| 37.5–37.6 | 2.398–2.392 | 12–17 |
| 44.4–44.9 | 2.040–2.019 | 7–9 |
| 50.4–50.7 | 1.811–1.801 | 4–6 |

EXAMPLE 23

(Preparation of MAPO-12)

Using the same reaction mixture and procedure as in Example 6, except that an equimolar amount of ethylenediamine ($C_2H_8N_2$) was substituted for diisopropylamine, the species MAPO-12 was produced instead of MAPO-5. In the MAPO-12 synthesis, the final reaction mixture had the composition expressed in terms of molar oxide ratios of:

1.0$C_2H_8N_2$:0.167MgO:0.917$Al_2O_3$:1.0$P_2O_5$:39.8-$H_2O$:0.33$CH_3COOH$.

The reaction mixture was placed in a sealed stainless steel pressure vessel and heated at 200° C. for 24 hours. The solid product was recovered by filtration, washed with water and dried in air at room temperature. A portion of the solid that passed through a 60 mesh screen (250 um) was subjected to X-ray analysis and chemical analysis. This solid had an X-ray powder diffraction pattern characterized by the following data.

TABLE E

| $2\theta$ | d,(A) | $100 \times I/I_o$ |
|---|---|---|
| 6.1 | 14.5 | 37 |
| 11.1 | 7.97 | 16 |
| 12.2 | 7.25 | 25 |
| 13.1 | 6.77 | 68 |
| 14.0 | 6.33 | 6 |
| 17.1 | 5.19 | 25 |
| 18.4 | 4.82 | 27 |
| 20.8 | 4.27 | 100 |
| 21.5 | 4.13 | 17 |
| 22.2 | 4.00 | 44 |
| 23.7 | 3.75 | 49 |
| 25.0 | 3.56 | 33 |
| 26.4 | 3.38 | 37 |
| 28.8 | 3.10 | 16 |
| 29.8 | 2.998 | 25 |
| 30.7 | 2.912 | 44 |
| 33.0 | 2.714 | 14 |
| 33.9 | 2.644 | 21 |
| 34.7 | 2.585 | 19 |

Chemical analysis established the chemical composition to be 29.9 wt. % $Al_2O_3$, 46.6 wt. % $P_2O_5$, 2.3 wt. % MgO, 8.1 wt. % C, 5.5 wt. % N, and 21.7 wt. % LOI, giving a product composition in molar oxide ratios of:

1.0$C_2H_8N_2$:0.17MgO:0.89$Al_2O_3$:1.0$P_2O_5$:0.24$H_2O$, or in terms of moles of ethylenediamine per average mole of $TO_2$ units, 0.25$C_2H_8N_2$:($Mg_{0.04}Al_{0.45}P_{0.51}$)$O_2$.

The species MAPO-12 as referred to herein is a magnesium aluminophosphate material having a three-dimensional microporous crystal framework structure of $PO_2^+$, $AlO_2^-$ and $MgO^{-2}$ tetrahedral units, units and whose essential empirical chemical composition on an anhydrous basis is:

$$mR:(Mg_xAl_yP_z)O_2$$

wherein "R" represents at least one organic templating agent present in the intracrystalline pore system; "m" represents the moles of "R" present per mole of $(Mg_xAl_yP_z)O_2$ and has a value of from zero to 0.3, "x", "y" and "z" represent respectively, the mole fractions of magnesium, aluminum and phosphorus present in the oxide moiety, said mole fractions being within the compositional area bounded by points A, B, C and D on the ternary diagram which is FIG. 1, or preferably within the area bounded by points a, b, c, and d on the ternary diagram which is FIG. 2, said magnesium aluminophosphate having a characteristic X-ray powder diffraction pattern which contains at least the d-spacings set forth below in Table V. In the form as synthesized in accordance with the process of this invention, "m" has a value of from 0.02 to 0.3.

TABLE V

| 2θ | d,(A) | Relative Intensity |
|---|---|---|
| 6.1 | 14.5 | m |
| 13.1 | 6.77 | s |
| 20.8 | 4.27 | vs |
| 22.2 | 4.00 | m |
| 23.7 | 3.75 | m |
| 26.4 | 3.38 | m |
| 30.7 | 2.912 | m |

EXAMPLE 24

(Preparation of MAPO-14)

Using the same reagents as in Example 23, above, but using proportionately more magnesium acetate tetrahydrate and less hydrated aluminum oxide (I), it was found that a different MAPO species, namely MAPO-14, was produced. The manipulative procedure used in forming the reaction mixture was essentially identical to that used in previous Examples 6 and 23. A first mixture was prepared by combining 46.2 grams of 85% orthophosphoric acid and 80.1 grams of water, to which was added 21.76 grams of hydrated aluminum oxide (I). A solution prepared by dissolving 17.2 grams of magnesium acetate tetrahydrate in 35.1 grams of H₂0 was added to this first mixture and to the resulting mixture 12.1 grams of ethylenediamine (C₂H₈N₂) was added to complete the reaction mixture formulation which had a composition in terms of oxide ratios of:

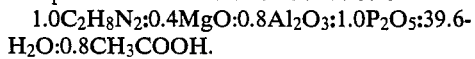

The reaction mixture was sealed in a stainless steel pressure vessel and heated for 24 hours. The solid product was recovered by filtration, washed with water and dried in air at room temperature. A portion of the solid that did not pass through a 60 mesh screen (250 um) was subjected to X-ray and chemical analysis. This solid was almost pure, and the major phase had an X-ray powder diffraction pattern characterized by the following data.

TABLE F

| 2θ | d,(A) | 100 × I/I$_o$ |
|---|---|---|
| 8.6 | 10.3 | 100 |
| 10.8 | 8.19 | 11 |
| 13.0 | 6.81 | 21 |
| 14.8 | 5.99 | 5 |
| 15.8 | 5.61 | 15 |
| 17.7 | 5.01 | 15 |
| 18.4 | 4.82 | 2 |
| 20.8 | 4.27 | 7 |
| 21.9 | 4.06 | 22 |
| 22.4 | 3.97 | 10 |
| 25.4 | 3.51 | 19 |
| 26.5 | 3.36 | 4 |
| 27.5 | 3.24 | 18 |
| 28.9 | 3.09 | 13 |
| 29.3 | 3.05 | 15 |
| 29.7 | 3.01 | 23 |
| 30.8 | 2.90 | 12 |
| 32.5 | 2.75 | 8 |
| 33.2 | 2.698 | 3 |
| 35.5 | 2.529 | 4 |
| 38.1 | 2.363 | 3 |

TABLE F-continued

| 2θ | d,(A) | 100 × I/I$_o$ |
|---|---|---|
| 39.8 | 2.265 | 4 |

By chemical analysis, the composition was found to be 25.7 wt. % Al₂O₃, 46.0 wt. % P₂O₅, 5.5 wt. % MgO, 4.0 wt. % C, 4.2 wt. % N, and 22.6 wt. % LOI, giving a product composition in molar oxide ratios of:

0.51(C₂H₈N₂):0.42MgO:0.78Al₂O₃:1.0P₂O₅:2.2H₂O, or an essential empirical chemical composition of 0.13C₂H₈N₂:(Mg$_{0.11}$Al$_{0.39}$P$_{0.50}$)O₂.

EXAMPLE 25

(Preparation of MAPO-14)

A reaction mixture was prepared using the same procedure and ingredients as in Example 24 above except that isopropylamine (C₃H₉N) was substituted for the ethylenediamine templating agent in that formulation. The composition of the reaction mixture in terms of molar oxide ratios was:

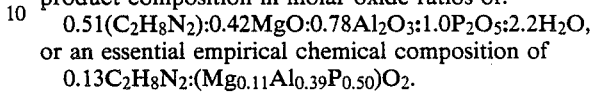

The reaction mixture was sealed in a stainless steel pressure vessel and heated at 150° C. for 168 hours. The solids were recovered by filtration, washed with water and air dried at room temperature. A portion of the solid product was subjected to X-ray analysis and a phase characterized by an X-ray powder diffraction pattern similar to that in Example 24 was observed in admixture.

The species MAPO-14 as referred to herein is a magnesium aluminophosphate material having a three-dimensional microporous crystal framework structure of PO₂⁺, AlO₂⁻ and MgO⁻² tetrahedral units, tetrahedral units and whose essential empirical chemical composition on an anhydrous basis is:

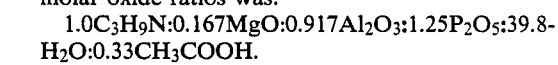

wherein "R" represents at least one organic templating agent present in the intracrystalline pore system; "m" represents the moles of "R" present per mole of (Mg$_x$Al$_y$P$_z$)O₂ and has a value of from zero to 0.3, "x", "y" and "z" represent respectively, the mole fractions of magnesium, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said magnesium aluminophosphate having a characteristic X-ray powder diffraction pattern which contains at least the d-spacings set forth below in Table VI. In the form as synthesized in accordance with the process of this invention, "m" has a value of from 0.02 to 0.3.

TABLE VI

| 2θ | d,(A) | Relative Intensity |
|---|---|---|
| 8.6 | 10.3 | vs |
| 13.0 | 6.81 | w |
| 21.9 | 4.06 | w |
| 25.4 | 3.51 | w |
| 27.5 | 3.24 | w |
| 29.7 | 3.01 | w |

EXAMPLE 26

(Preparation of MAPO-16)

A solution was prepared by combining 46.1 grams of 85% orthophosphoric acid, 60.2 grams of water, and 3.2 grams of magnesium oxide with stirring. To this solution was added 22.0 grams of a hydrated aluminum oxide (II) and to the resulting mixture was added a solution consisting of 22.2 grams of quinuclidine ($C_7H_{13}N$) and 60.3 grams of water to form the final reaction mixture whose composition in terms of molar oxide ratios was:

1.0$C_7H_{13}$N:0.4MgO:0.8$Al_2O_3$:1.0$P_2O_5$:40$H_2O$,

The reaction mixture was placed in a sealed stainless steel reactor and heated at 150° C. for 24 hours. The solid product was recovered by filtration, washed with water, and dried in air at room temperature. A portion of the solids was subjected to X-ray analysis. The solid was impure but the major phase, denominated MAPO-16 had an X-ray powder diffraction pattern characterized by the following data:

TABLE G

| 2θ | d,(A) | 100 × I/$I_o$ |
|---|---|---|
| 11.5 | 7.69 | 55 |
| 18.8 | 4.72 | 49 |
| 22.1 | 4.02 | 100 |
| 23.0 | 3.87 | 13 |
| 26.6 | 3.35 | 19 |
| 29.1 | 3.07 | 13 |
| 29.9 | 2.99 | 23 |
| 38.0 | 2.37 | 6 |
| 48.6 | 1.87 | 6 |

EXAMPLE 27

(Preparation of MAPO-16)

(a) The preparation of MAPO-16 as set forth in Example 26, above, was repeated except that the relative amount of magnesium in the reaction mixture (using magnesium acetate in this instance rather than magnesium oxide) was decreased by about two thirds, resulting in a final gel composition of 1.0$C_7H_{13}$N:0.167MgO:0.917$Al_2O_3$:$P_2O_5$:39.8-$H_2O$:0.33$CH_3COOH$.

The reaction mixture was sealed in a stainless steel pressure vessel and heated at 150° C. for 72 hours. The solid consisted of a fine powder and a few large sheet-like aggregates. A portion of the fine solid was subjected to X-ray and chemical analysis. This solid had an X-ray powder diffraction pattern essentially identical to that of the major phase in Example 26. Chemical analysis established that the sample consisted of 30.8 wt.% $Al_2O_3$, 45.1 wt.% $P_2O_5$, 2.7 wt.% MgO, 10.9 wt. % C, 1.6 wt.% N, and 20.5 wt.% LOI, giving a product composition in molar oxide ratios of:

0.41$C_7H_{13}$N:0.21MgO:0.95$Al_2O_3$:1.0$P_2O_5$:1.1$H_2O$, or alternatively 0.1$C_7H_{13}$N:($Mg_{0.05}Al_{0.46}P_{0.49}$)$O_2$:0.27$H_2O$, (b) A portion of a solid crystalline product exhibiting an X-ray powder diffraction pattern essentially identical to that in example 26 was calcined at 600° C. for 2½ hours. The calcined product had an X-ray powder diffraction pattern essentially identical to that of the major phase in example 26.

(c) Adsorption capacities were measured on a portion of the calcined solid of part (b) using a standard McBain-Bakr gravimetric adsorption apparatus. The following data were obtained on a sample activated at 350°±20° C.:

| Adsorbate | Kinetic Diameter, A | Pressure, Torr | Temp., °C. | Wt. % Absorbed |
|---|---|---|---|---|
| Oxygen | 3.46 | 701 | −183 | 4.6 |
| Oxygen | 3.46 | 101 | −183 | 2.8 |
| n-butane | 4.3 | 703 | 24 | 0.6 |
| $H_2O$ | 2.65 | 4.6 | 24 | 19.9 |
| $H_2O$ | 2.65 | 20 | 24 | 27.5 |

The species MAPO-16 as referred to herein is a magnesium aluminophosphate material having a three-dimensional microporous crystal framework structure of $PO_2^+$, $AlO_2^-$ and $MgO^{-2}$ tetrahedral units, units and whose essential empirical chemical composition on an anhydrous basis is: mR: ($Mg_xAl_yP_z$)$O_2$ wherein "R" represents at least one organic templating agent present in the intracystalline pore system; "m" represents the moles of "R" present per mole of ($Mg_xAl_yP_z$)$O_2$ and has a value of from zero to 0.3, "x", "y" and "z" represent respectively, the mole fractions of magnesium, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said magnesium aluminophosphate having a characteristic X-ray powder diffraction pattern which contains at least the d-spacings set forth below in Table VII. In the form as synthesized in accordance with the process of this invention, "m" has a value of from 0.02 to 0.3.

TABLE VII

| 2θ | d,(A) | Relative Intensity |
|---|---|---|
| 11.4–11.6 | 7.76–7.63 | s-vs |
| 18.7–18.9 | 4.75–4.70 | w-s |
| 22.0–22.1 | 4.04–4.02 | m-vs |
| 23.0 | 3.87 | vw-w |
| 26.6–26.7 | 3.35–3.34 | w |
| 29.8–29.9 | 3.00–2.99 | w |

All of the as-synthesized MAPO-16 compositions for which X-ray powder diffraction data have presently been obtained have patterns which are within the generalized pattern of Table VII (a) below:

TABLE VII (a)

| 2θ | d,(A) | 100 × I/$I_o$ |
|---|---|---|
| 11.4–11.6 | 7.76–7.63 | 55–100 |
| 18.7–18.9 | 4.75–4.70 | 17–51 |
| 22.0–22.1 | 4.04–4.03 | 45–100 |
| 23.0 | 3.87 | 9–14 |
| 26.6–26.7 | 3.35–3.34 | 11–22 |
| 29.0–29.1 | 3.08–3.07 | 9–16 |
| 29.8–29.9 | 3.00–2.99 | 14–25 |
| 37.8–38.0 | 2.380–2.368 | 5–8 |
| 48.3–48.6 | 1.884–1.873 | 3–8 |

EXAMPLE 28

(Preparation of MAPO-17)

(a) Quinuclidine was also found to template the formation of a structural species of this invention denominated MAPO-17. Experimentally a first mixture was prepared by combining 46.2 grams of 85% orthophosphoric acid and 69.9 grams of water, to which was added 25.0 grams of a hydrated aluminum oxide (I), and to the resulting mixture was added a solution prepared by dissolving 7.2 grams of magnesium acetate tetrahydrate in 22.7 grams of H₂O. To this mixture was added a solution of 22.3 grams of quinuclidine (C₇H₁₃N) and 25.0 grams of water to form the final reaction mixture which has a composition expressed in terms of molar oxide ratios of:

1.0C₇H₁₃N:0.167MgO:0.917Al₂O₃:1.0P₂O₅:39.8-H₂O:0.33CH₃COOH.

The reaction mixture was placed in a sealed stainless steel pressure vessel and heated at 200° C. for 168 hours. The solid product was washed three times by suspending it in water, centrifuging, and decanting the supernatant, then dried in air at room temperature. By X-ray analysis, the solid was impure, but the minor phase had an X-ray powder diffraction pattern characterized by the following data:

TABLE H

| 2θ | d (A) | 100 I/I₀ |
|---|---|---|
| 7.7 | 11.4 | 100 |
| 9.8 | 9.05 | 50 |
| 13.4 | 6.60 | 51 |
| 14.3 | 6.21 | 33 |
| 14.6 | 6.05 | 14 |
| 15.5 | 5.72 | 70 |
| 16.6 | 5.34 | 36 |
| 18.0 | 4.93 | 39 |
| 19.6 | 4.53 | 88 |
| 20.5 | 4.33 | 96 |
| 21.4 | 4.15 | 83 |
| 23.3 | 3.81 | 55 |
| 23.8 | 3.73 | 48 |
| 25.3 | 3.52 | 87 |
| 27.4 | 3.25 | 23 |
| 28.8 | 3.10 | 41 |
| 30.6 | 2.92 | 19 |
| 31.3 | 3.861 | 30 |
| 31.8 | 2.812 | 78 |
| 33.6 | 2.667 | 17 |
| 34.4 | 2.604 | 14 |
| 34.8 | 2.575 | 23 |

(b) EDAX (energy dispersive analysis by X-ray microprobe analysis in conjunction with SEM (scanning electron microscope) study on clean crystals having a morphology characteristic of MAPO-17 gave the following analysis based on relative peak heights:

| | Average of Spot Probes |
|---|---|
| Mg | 0.04 |
| Al | 0.43 |
| P | 0.54 |

EXAMPLE 29

(Preparation of MAPO-17)

Using essentially the same procedure and reagents as in Example 28, above except that cyclohexylamine (C₆H₁₃N) was substituted for the quinuclidine templating agent of that Example 28, MAPO-17 was prepared from a reaction mixture having a composition in terms of molar oxide ratios of:

1.0C₆H₁₃N:0.167MgO:0.917Al₂O₃:P₂O₅:39.8-H₂O:0.33CH₃COOH.

The reaction mixture was sealed in a stainless steel pressure vessel and heated at 200° C. for 168 hours. The solids were recovered by filtration, washed with water, and dried in air at room temperature. A portion of the solid product was examined by X-ray analysis, and a phase identified by its powder diffraction pattern as MAPO-17 was found to be present.

The species MAPO-17 as referred to herein is a magnesium aluminophosphate material having a three-dimensional microporous crystal framework structure of PO₂⁺, AlO₂⁻ and MgO⁻² tetrahedral units, and whose essential empirical chemical composition on an anhydrous basis is:

mR:(Mg$_x$Al$_y$P$_z$)O₂ wherein "R" represents at least one organic templating agent present in the intracrystalline pore system; "m" represents the moles of "R" present per mole of (Mg$_x$Al$_y$P$_z$)O₂ and has a value of from zero to 0.3, "x", "y" and "z" represent respectively, the mole fractions of magnesium, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said magnesium aluminophosphate having a characteristic X-ray powder diffraction pattern which contains at least the d-spacings set forth below in Table VIII. In the form as synthesized in accordance with the process of this invention, "m" has a value of from 0.02 to 0.03.

TABLE VIII

| 2θ | d, (A) | Relative Intensity |
|---|---|---|
| 7.7 | 11.4 | vs |
| 19.6 | 4.53 | s |
| 20.5 | 4.33 | vs |
| 21.4 | 4.15 | s |
| 25.3 | 3.52 | s |
| 31.8 | 2.812 | s |

EXAMPLE 30

(Preparation of MAPO-20)

The structural species of the present invention denominated as MAPO-20 was synthesized using tetramethylammonium hydroxide pentahydrate (TMAOH.5H₂O) as the templating agent. To prepare the reaction mixture a first mixture was formed by combining 46.1 grams of 85% orthophosphoric acid, 51.3 grams of water, and 3.2 grams of magnesium oxide (MgO) and adding to this solution 22.0 grams of a hydrated aluminum oxide (II). A solution consisting of 32.6 grams of tetramethylammonium hydroxide pentahydrate and 51.3 grams of H₂O was added to this mixture to form the final reaction mixture having a composition in molar oxide ratios of:

1.0TMAOH:0.4Mgo:0.8Al₂O₃:1.0P₂O₅:40H₂O.

The reaction mixture was sealed in an inert plastic screw-cap bottle (polytetrafluoroethylene) and heated at 100° C. for 41 hours. The solid product was recovered by filtration, washed with water, and dried in air at room temperature. A portion of the solids was subjected to X-ray analysis. The product was impure, but the major phase has the following powder diffraction pattern which is characteristic of MAPO-20.

TABLE J

| 2θ | d, (A) | 100 × I/I₀ |
|---|---|---|
| 13.9 | 6.37 | 47 |
| 19.6 | 4.53 | 42 |
| 22.0 | 4.04 | 8 |

TABLE J-continued

| 2θ | d, (A) | 100 × I/I₀ |
|---|---|---|
| 24.1 | 3.69 | 100 |
| 27.8 | 3.21 | 15 |
| 31.3 | 2.86 | 12 |
| 34.4 | 2.61 | 15 |
| 37.2 | 2.42 | 1 |
| 39.8 | 2.26 | 4 |
| 42.4 | 2.13 | 4 |
| 47.0 | 1.93 | 4 |
| 51.4 | 1.78 | 8 |

EXAMPLE 31

(Preparation of MAPO-20)

The procedure of Example 30, above, was repeated except that the crystallization period at 100° C. was extended from 41 to 72 hours. The product solids had an X-ray powder diffraction pattern essentially identical to that set forth in TABLE J. Chemical analysis established the composition to contain 28.0 wt. % $Al_2O_3$, 43.0 wt. % $P_2O_5$, 5.6 wt.% MgO, 8.1 wt.% C, 2.4 wt.% N, and 22.3 wt.% LOI, giving a product composition in molar oxide ratios of:

0.56$C_4H_{13}NO$:0.46MgO:0.91$Al_2O_3$:$P_2O_5$:1.1$H_2O$, or alternatively, 0.13TMAOH:($Mg_{0.11}Al_{0.42}P_{0.47}$)$O_2$.

EXAMPLE 32

(Preparation of MAPO-20)

(a) A reaction mixture having a composition in terms of molar oxide ratios of:

1.0TMAOH:0.167MgO:0.917$Al_2O_3$:$P_2O_5$:40$H_2O$:0.33$CH_3COOH$ was prepared by combining a solution of 46.2 grams of 85% orthophosphoric acid in 59.2 grams of water with 24.9 grams of a hydrated aluminum oxide (I). A second solution prepared by dissolving 7.2 grams of magnesium acetate tetrahydrate in 20.3 grams of water was then added to the first solution. The resulting mixture was added to a third solution composed of 36.3 grams of tetramethylammonium hydroxide pentahydrate (TMAOH.5$H_2O$) in 20.1 grams of water. The reaction mixture was sealed in a stainless steel pressure vessel and heated at 200° C. for 24 hours. The solid product was washed three times by suspending it in water, centrifuging, and decanting the supernatant, then dried in air at room temperature. A portion of the solids was subjected to X-ray analysis and chemical analysis. The solid had an X-ray powder diffraction pattern essentially identical to that of the major phase in Example 30. Chemical analysis showed 31.0 wt.% $Al_2O_3$, 46.7 wt.% $P_2O_5$, 2.3 wt.% MgO, 8.2 wt.% C, 2.0 wt.% N, and 19.8 wt.% LOI, giving a product composition in molar oxide ratios of:

0.52$C_4H_{13}NO$:0.18MgO:0.92$Al_2O_3$:$P_2O_5$:0.74$H_2O$ or 0.13TMAOH:($Mg_{0.04}Al_{0.46}P_{0.50}$)$O_2$:0.18$H_2O$, (b) A portion of the solid was calcined in air at 600° C. for 2½ hours. The calcined product had an X-ray powder diffraction pattern essentially identical to that in Example 30.

(c) Adsorption capacities were measured on a portion of this calcined solid using a standard McBain-Bakr gravimetric adsorption apparatus. The following data were obtained on a sample activated at 350±20° C.:

| Adsorbate | Kinetic Diameter, Å | Pressure, Torr | Temp., °C. | Wt. % Adsorbed |
|---|---|---|---|---|
| Oxygen | 3.46 | 701 | −183 | 2.1 |
| Oxygen | 3.46 | 101 | −183 | 0.5 |
| n-butane | 4.3 | 703 | 24 | 0.4 |
| $H_2O$ | 2.65 | 4.6 | 24 | 23.8 |
| $H_2O$ | 2.65 | 20.0 | 24 | 31.5 |

EXAMPLE 33

(Preparation of MAPO-20)

MAPO-20 was found to be produced from a reaction mixture containing tetraethylammonium hydroxide (TEAOH) as the templating agent and prepared using the procedures and other reagents described in Example 30, supra. The composition of the final reaction mixture in terms of molar oxide ratios was 1.0TEAOH:0.33MgO:0.83$Al_2O_3$:$P_2O_5$:40$H_2O$.

The reaction mixture was placed in a closed polytetrafluoroethylene screw-cap bottle and heated in an oven at 100° C. at autogenous pressure for 24 hours. The solids were recovered by filtration, washed with water, and dried in air at room temperature. X-ray analysis of a portion of the solid product established the MAPO-20 was present, but not as the major phase.

EXAMPLE 34

(Preparation of MAPO-20)

MAPO-20 was also produced in admixture with other phases from a reaction mixture containing quinuclidine ($C_7H_{13}N$) as the templating agent by a procedure similar to that used in Example 30, supra. The other ingredients of the reaction mixture were magnesium oxide, orthophosphoric acid, a hydrated aluminum oxide (II) and water, the total composition being in terms of molar oxide ratios:

1.0$C_7H_{13}N$:0.4MgO:0.8$Al_2O_3$:$P_2O_5$:40$H_2O$.

The reaction mixture was placed in a sealed stainless steel pressure vessel and heated at 200° C. for 168 hours. The solids were recovered by filtration, washed with water, and dried in air at room temperature.

EXAMPLE 35

(Preparation of MAPO-20)

Using tetramethylammonium hydroxide pentahydrate, orthophosphoric acid, water, magnesium acetate tetrahydrate and a hydrated aluminum oxide (I), a reaction mixture having the composition:

1.0TMAOH:0.667MgO:0.667$Al_2O_3$:$P_2O_5$:40$H_2O$:1.33$CH_3COOH$ was prepared using the procedure of Example 32, supra. The reaction mixture was crystallized under autogenous pressure at 200° C. for 72 hours in a sealed stainless steel reactor. X-ray analysis of the recovered solid product resulted in an X-ray powder diffraction pattern essentially identical to that of Example 30. Chemical analysis showed the composition to be 8.3 wt.% MgO, 22.0 wt.% $Al_2O_3$, 47.5 wt.% $P_2O_5$, 10.6 wt.% C, 3.1 wt.% N and 22.4 wt.% LOI, giving a product composition of 0.66TMAOH:0.62MgO:0.64$Al_2O_3$:$P_2O_5$:$H_2O$, or alternatively 0.17TMAOH:($Mg_{0.16}Al_{0.33}P_{0.51}$)$O_2$:0.26$H_2O$.

The species MAPO-20 as referred to herein is a magnesium aluminophosphate material having a three-dimensional microporous crystal framework structure of $PO_2^+$, $AlO_2^-$ and tetrahedral units, and whose essential empirical chemical composition on an anhydrous basis is:

$$mR:(Mg_xAl_yP_z)O_2$$

wherein "R" represents at least one organic templating agent present in the intracrystalline pore system; "m" represents the moles of "R" present per mole of $(Mg_xAl_yP_z)O_2$ and has a value of from zero to 0.3, "x", "y" and "z" represent respectively, the mole fractions of magnesium, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said magnesium aluminophosphate having a characteristic X-ray powder diffraction pattern which contains at least the d-spacings set forth below in Table IX. In the form as synthesized in accordance with the process of this invention, "m" has a value of from 0.02 to 0.3.

TABLE IX

| 2θ | d, (A) | Relative Intensity |
|---|---|---|
| 13.8–14.1 | 6.42–6.28 | m–vs |
| 19.6–20.0 | 4.53–4.44 | w–s |
| 24.1–24.5 | 3.69–3.63 | m–vs |
| 27.8–28.4 | 3.21–3.14 | vw–w |
| 31.2–31.9 | 2.867–2.805 | vw–w |
| 34.3–35.0 | 2.614–2.564 | vw–w |

All of the as-synthesized MAPO-20 compositions for which X-ray powder diffraction data have presently been obtained have patterns which are within the generalized pattern of Table IX(a), below:

TABLE IX(a)

| 2θ | d, (A) | 100 × I/I$_o$ |
|---|---|---|
| 13.8–14.1 | 6.42–6.28 | 46–100 |
| 19.6–20.0 | 4.53–4.44 | 15–51 |
| 21.9–22.4 | 4.06–3.97 | 4–10 |
| 24.1–24.5 | 3.69–3.63 | 46–100 |
| 27.8–28.4 | 3.21–3.14 | 9–18 |
| 31.2–31.9 | 2.867–2.805 | 8–16 |
| 34.3–35.0 | 2.614–2.564 | 8–18 |
| 37.0–37.9 | 2.430–2.374 | 1–3 |
| 39.7–40.8 | 2.270–2.212 | 2–4 |
| 42.3–42.8 | 2.137–2.113 | 1–6 |
| 47.0–48.2 | 1.933–1.888 | 1–5 |
| 51.4–52.6 | 1.778–1.740 | 3–10 |

EXAMPLE 36

(Preparation of MAPO-34)

(a) A solution was prepared by combining 23.1 grams of 85% orthophosphoric acid, 38.2 grams of water, and 1.6 grams of magnesium oxide (MgO). To this solution was added 11.0 grams of a hydrated aluminum oxide (II), and to the resulting mixture was added 36.8 grams of aqueous 40 wt.% tetraethylammonium hydroxide (TEAOH) to form the final reaction mixture which had a composition in terms of molar oxide ratios of:

$1.0TEAOH:0.4MgO:0.8Al_2O_3:P_2O_5:40H_2O$.

The reaction mixture was sealed in a stainless steel pressure vessel and heated at 200° C. for 72 hours. The solid product was recovered by filtration, washed with water, and dried in air at room temperature. The X-ray powder diffraction pattern of a portion of the recovered solid product was characterized by the following data:

TABLE K

| 2θ | d, (A) | 100 × I/I$_o$ |
|---|---|---|
| 9.5 | 9.31 | 100 |
| 12.8 | 6.92 | 14 |
| 14.1 | 6.28 | 17 |
| 16.0 | 5.54 | 39 |
| 18.1 | 4.90 | 23 |
| 20.6 | 4.31 | 91 |
| 22.2 | 4.00 | 5 |
| 23.1 | 3.85 | 6 |
| 25.3 | 3.52 | 25 |
| 25.8 | 3.45 | 17 |
| 27.6 | 3.23 | 4 |
| 28.4 | 3.14 | 4 |
| 29.5 | 3.03 | 5 |
| 30.5 | 2.93 | 31 |
| 31.3 | 2.86 | 23 |
| 34.3 | 2.61 | 7 |
| 36.3 | 2.47 | 3 |
| 39.5 | 2.28 | 3 |
| 43.2 | 2.09 | 4 |
| 47.4 | 1.92 | 3 |
| 48.8 | 1.87 | 5 |
| 50.9 | 1.79 | 4 |

Chemical analysis showed 14.9 wt.% Al, 20.7 wt.% P, 3.29 wt.% Mg, 9.6 wt.% C, and 1.3 wt.% N, giving a product composition in molar oxide ratios of $0.28TEAOH:0.41MgO:0.83Al_2O_3:P_2O_5:0.5H_2O$, or alternatively:

$0.07TEAOH:(Mg_{0.10}Al_{0.41}P_{0.49})O_2:0.12H_2O$.

(b) A portion of the solid was calcined in air for 1¼ hour at 200°, 1¾ hour at 400°, and 1¼ hour at 600° C. The calcined product had an X-ray powder diffraction pattern characterized by the following data:

TABLE L

| 2θ | d, (A) | 100 × I/I$_o$ |
|---|---|---|
| 9.6 | 9.21 | 100 |
| 13.0 | 6.81 | 32 |
| 14.2 | 6.24 | 4 |
| 16.2 | 5.47 | 18 |
| 18.0 | 4.93 | 18 |
| 19.2 | 4.62 | 4 |
| 20.8 | 4.27 | 51 |
| 22.2 | 4.00 | 4 |
| 22.5 | 3.95 | Shoulder |
| 23.2 | 3.83 | 5 |
| 25.2 | 3.53 | 17 |
| 26.1 | 3.41 | 13 |
| 27.8 | 3.21 | 3 |
| 28.4 | 3.14 | 4 |
| 29.7 | 3.01 | 2 |
| 30.8 | 2.90 | 27 |
| 31.3 | 2.86 | 15 |
| 31.8 | 2.81 | 2 |
| 33.8 | 2.65 | 2 |
| 34.6 | 2.59 | 5 |
| 36.3 | 2.47 | 3 |
| 38.8 | 2.32 | 2 |
| 43.1 | 2.10 | 2 |
| 43.6 | 2.08 | 2 |
| 47.8 | 1.90 | 3 |
| 49.1 | 1.86 | 5 |
| 51.0 | 1.79 | 3 |
| 53.4 | 1.72 | 3 |
| 54.7 | 1.68 | 2 |

(c) Adsorption capacities were measured on the calcined product of part (b) using a standard McBain-Bakr gravimetric adsorption apparatus. The following data were obtained on a sample activated at 350° C.:

| Adsorbate | Kinetic Diameter, A | Pressure, Torr | Temp., °C. | Wt. % Adsorbed |
|---|---|---|---|---|
| O₂ | 3.46 | 117 | −183 | 25.4 |
| O₂ | 3.46 | 708 | −183 | 30.9 |
| n-Butane | 4.3 | 712 | 23 | 13.1 |
| isobutane | 5.0 | 717 | 24 | 0.8 |
| H₂O | 2.65 | 4.6 | 23 | 29.0 |
| H₂O | 2.65 | 16 | 23 | 33.2 |

(d) Following the adsorption measurements, the sample exhibited an X-ray diffraction powder pattern similar to that before adsorption.

(e) using the same reagents as in part (a) above, a reaction mixture was prepared free of any organic templating agent but otherwise having the same relative proportions of the other ingredients. The mixture was heated at 200° C. for 72 hours under autogenous pressure to produce a solid product, which by X-ray analysis was found to contain none of the compositions of the present invention but rather comprised a complex mixture of structure types including AlPO₄-quartz, AlPO₄-tridymite and AlPO₄-cristobalite and one or more unidentified materials.

EXAMPLE 37

(Preparation of MAPO-34)

Using the same reaction mixture and method of preparation as set forth in Example 35, supra, except that tetraethylammonium hydroxide was substituted in equimolar proportion for the tetramethylammonium hydroxide employed therein, a MAPO-34 product was crystallized instead of the MAPO-20 composition of Example 35. Crystallization occurred over the period of 170 hours at 100° C. and under autogenous pressure. A portion of the water-washed and air-dried solids that passed through a 60 mesh screen (250 um) was subjected to X-ray and chemical analysis. The product was impure but the major phase had an X-ray powder diffraction pattern essentially identical to that of the composition Example 36(a).

Chemical analysis showed 26.4 wt.% Al₂O₃, 45.8 wt.% P₂O₅, 5.1 wt.% MgO, 10.0 wt.% C, 1.6 wt.% N, and 21.1 wt.% LOI, giving a product composition in molar oxide ratios of:

0.32TEAOH:0.38MgO:0.80Al₂O₃:P₂O₅:H₂O, or alternatively, 0.08TEAOH:(Mg₀.₁₀Al₀.₄₀P₀.₅₀)O₂:0.25H₂O.

EXAMPLE 38

(Preparation of MAPO-34)

A procedure similar to that of Example 37 was followed using isopropylamine (C₃H₉N) as the templating agent. The composition of the final reaction mixture in terms of molar oxide ratios was:

1.0C₃H₉N:0.40MgO:0.80Al₂O₃:P₂O₅:39.6-H₂O:0.80CH₃COOH.

The reaction mixture was sealed in a stainless steel pressure vessel and heated at 150° C. for 24 hours.

The solids were recovered by filtration, washed with water, and dried in air at room temperature. The solid product was impure but contained a phase characterized by an X-ray powder diffraction pattern similar to that of the product in Example 36(a).

The species MAPO-34 as referred to herein is a magnesium aluminophosphate material having a three-dimensional microporous crystal framework structure of $PO_2^+$, $AlO_2^-$ and $MgO^{-2}$ tetrahedral units, and whose essential empirical chemical composition on an anhydrous basis is:

$$mR:(Mg_xAl_yP_z)O_2$$

wherein "R" represents at least one organic templating agent present in the intracrystalline pore system; "m" represents the moles of "R" present per mole of $(Mg_xAl_yP_z)O_2$ has a value of from zero to 0.3, "x", "y" and "z" represent respectively, the mole fractions of magnesium, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said magnesium aluminophosphate having a characteristic X-ray powder diffraction pattern which contains at least the d-spacings set forth below in Table X. In the form as synthesized in accordance with the process of this invention, "m" has a value of from 0.02 to 0.3.

TABLE X

| 2θ | d, (A) | Relative Intensity |
|---|---|---|
| 9.4–9.6 | 9.41–9.21 | s–vs |
| 12.7–13.0 | 6.97–6.81 | w–m |
| 18.0–18.4 | 4.93–4.82 | w–m |
| 20.4–20.8 | 4.35–4.27 | s–vs |
| 25.1–25.3 | 3.55–3.52 | w |
| 30.3–30.8 | 2.95–2.90 | w–m |

All of the as-synthesized MAPO-34 compositions for which X-ray powder diffraction data have presently been obtained have patterns which are within the generalized pattern of Table X(a), below:

TABLE X(a)

| 2θ | d, (A) | 100 × I/I₀ |
|---|---|---|
| 9.4–9.6 | 9.41–9.21 | 74–100 |
| 12.7–13.0 | 6.97–6.81 | 14–32 |
| 14.0–14.2 | 6.33–6.24 | 4–19 |
| 15.9–16.2 | 5.57–5.47 | 18–51 |
| 18.0–18.4 | 4.93–4.82 | 18–34 |
| 20.4–20.8 | 4.35–4.27 | 51–100 |
| 22.2 | 4.00 | 4–7 |
| 23.0–23.2 | 3.87–3.83 | 5–6 |
| 25.1–25.3 | 3.55–3.52 | 17–30 |
| 25.7–26.1 | 3.47–3.41 | 13–20 |
| 27.4–27.8 | 3.25–3.21 | 3–5 |
| 28.3–28.4 | 3.15–3.14 | 3–4 |
| 29.4–29.7 | 3.04–3.01 | 2–5 |
| 30.3–30.8 | 2.95–2.90 | 27–32 |
| 31.2–31.3 | 2.867–2.849 | 15–26 |
| 33.7–33.9 | 2.660–2.644 | 2–4 |
| 34.2–34.6 | 2.622–2.592 | 5–8 |
| 39.4–39.5 | 2.287–2.281 | 2–4 |
| 43.1–43.2 | 2.099–2.094 | 2–5 |
| 47.3–47.8 | 1.922–1.903 | 3–5 |
| 48.8–49.1 | 1.866–1.855 | 4–5 |
| 50.9–51.0 | 1.794–1.791 | 3–4 |
| 54.4–54.7 | 1.687–1.678 | 2–3 |
| 55.6–55.7 | 1.653–1.647 | 2–3 |

EXAMPLE 39

(Preparation of MAPO-35)

(a) In the synthesis of the structural species MAPO-35 of the present invention, a solution was prepared by combining 46.1 grams of 85% orthophosphoric acid, 60.2 grams of water, and 3.2 grams of magnesium oxide (MgO). To this solution was added 22.0 grams of a hydrated aluminum oxide (II), and to the resulting mixture was added a solution consisting of 22.2 grams of quinuclidine ($C_7H_{13}N$) and 60.3 grams of water to form the final reaction mixture. The composition of the final reaction mixture in molar oxide ratios was: $1.0C_7H_{13}N{:}0.4MgO{:}0.8Al_2O_3{:}P_2O_5{:}H_2O$ The reaction mixture was placed in a closed inert plastic screwcap bottle (polytetrafluoroethylene) and heated in an oven at 100° C. at autogenous pressure for 146 hours. The solid product was recovered by filtration, washed with water, and dried in air at room temperature. A portion of the solids was subjected to X-ray and chemical analysis. The solid had an X-ray powder diffraction pattern characterized by the following data:

TABLE M

| $2\theta$ | d, (A) | $100 \times I/I_o$ |
|---|---|---|
| 8.7 | 10.2 | 21 |
| 11.1 | 7.98 | 43 |
| 13.4 | 6.61 | 28 |
| 16.0 | 5.54 | 9 |
| 17.4 | 5.10 | 100 |
| 17.9 | 4.96 | 17 |
| 19.6 | 4.53 | 11 |
| 21.2 | 4.19 | 62 |
| 22.0 | 4.04 | 100 |
| 22.8 | 3.90 | 9 |
| 23.3 | 3.82 | 21 |
| 23.7 | 3.75 | 9 |
| 25.1 | 3.55 | 4 |
| 26.9 | 3.31 | 26 |
| 28.6 | 3.12 | 34 |
| 28.7 | 3.11 | Shoulder |
| 29.1 | 3.07 | Shoulder |
| 32.2 | 2.78 | 17 |
| 34.6 | 2.59 | 11 |
| 35.8 | 2.51 | 4 |
| 42.2 | 2.14 | 4 |
| 43.1 | 2.10 | 4 |
| 48.5 | 1.88 | 6 |
| 49.4 | 1.84 | 4 |

Chemical analysis established the composition of the product to contain 26.1 wt.% $Al_2O_3$, 44.0 wt.% $P_2O_5$, 6.3 wt.% MgO, 11.4 wt.% C, 2.2 wt.% N, and 23.1 wt.% LOI, giving a product composition in molar oxide ratios of:

$0.44C_7H_{13}N{:}0.52MgO{:}0.83Al_2O_3{:}P_2O_5{:}1.4H_2O$, or alternatively:

$0.11C_7H_{13}N{:}(Mg_{0.12}Al_{0.40}P_{0.48})O_2{:}0.33H_2O$.

(b) A portion of this solid was heated in a vacuum oven at 150° C. for 16 hours to remove any adsorbed water. This activated sample was then stored in moist air at a constant relative humidity of 79% until there was essentially no further weight gain. This hydrated sample exhibited a weight gain of 5.2% based on the activated weight.

The species MAPO-35 as referred to herein is a magnesium aluminophosphate material having a three-dimensional microporous crystal framework structure of $PO_2^+$, $AlO_2^-$ and $MgO^{-2}$ tetrahedral units, and whose essential empirical chemical composition on an anhydrous basis is:

$mR{:}(Mg_xAl_yP_z)O_2$ wherein "R" represents at least one organic templating agent present in the intracrystalline pore system; "m" represents the moles of "R" present per mole of $(Mg_xAl_yP_z)O_2$ and has a value of from zero to 0.3, "x", "y" and "z" represent respectively, the mole fractions of magnesium, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said magnesium aluminophosphate having a characteristic X-ray powder diffraction pattern which contains at least the d-spacings set forth below in Table XI. In the form as synthesized in accordance with the process of this invention, "m" has a value of from 0.02 to 0.3.

TABLE XI

| $2\theta$ | d, (A) | $100 \times I/I_o$ |
|---|---|---|
| 11.0–11.1 | 8.04–7.97 | m |
| 13.4 | 6.61 | w |
| 17.3–17.4 | 5.13–5.10 | s–vs |
| 21.2 | 4.19 | s |
| 21.9–22.0 | 4.06–4.04 | vs |
| 28.5–28.6 | 3.03–3.02 | w–m |

All of the as-synthesized MAPO-35 compositions for which X-ray powder diffraction patterns have presently been obtained, have X-ray patterns within the generalized pattern of Table XI(a), below:

TABLE XI(a)

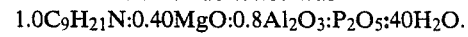

| $2\theta$ | d, (A) | $100 \times I/I_o$ |
|---|---|---|
| 8.6–8.7 | 10.3–10.2 | 18–21 |
| 11.0–11.1 | 8.04–7.97 | 40–43 |
| 13.4 | 6.61 | 25–28 |
| 15.9–16.0 | 5.57–5.54 | 9–11 |
| 17.3–17.4 | 5.13–5.10 | 78–100 |
| 17.8–17.9 | 4.98–4.96 | 14–18 |
| 19.4–19.6 | 4.58–4.53 | 8–11 |
| 21.2 | 4.19 | 55–62 |
| 21.9–22.0 | 4.06–4.04 | 99–100 |
| 22.7–22.8 | 3.92–3.90 | 6–9 |
| 23.3 | 3.82 | 20–22 |
| 23.7 | 3.75 | 6–9 |
| 25.1 | 3.55 | 4–6 |
| 26.8–26.9 | 3.33–3.31 | 18–26 |
| 28.5–28.6 | 3.03–3.02 | 15–34 |
| 28.7 | 3.11 | shoulder |
| 29.1 | 3.07 | shoulder |
| 32.1–32.2 | 2.788 | 44–47 |
| 34.6 | 2.592 | 8–11 |
| 35.7–35.8 | 2.515–2.508 | 4–5 |
| 42.1–42.2 | 2.146–2.131 | 4 |
| 43.1 | 2.099 | 3–4 |
| 48.4–48.5 | 1.881–1.877 | 6–8 |
| 49.4–49.5 | 1.845–1.841 | 5 |

EXAMPLE 40

(Preparation of MAPO-36)

(a) A solution was prepared by combining 46.1 grams of 85% orthophosphoric acid, 120.6 grams of water, and 3.2 grams of magnesium oxide (MgO). To this solution was added 22.0 grams of a hydrated aluminum oxide (II), and to the resulting mixture 28.7 grams of tripropylamine ($C_9H_{21}N$) was added to form the final reaction mixture. The composition of the final reaction mixture in molar oxide ratios was $1.0C_9H_{21}N{:}0.40MgO{:}0.8Al_2O_3{:}P_2O_5{:}40H_2O$.

The reaction mixture was placed in a sealed stainless steel pressure vessel and heated at 150° C. for 24 hours. The solid product was recovered by filtration, washed with water, and dried in air at room temperature. A portion of the solid was subjected to X-ray analysis. The solid was impure but the major phase was identified as MAPO-36.

EXAMPLE 41

(Preparation of MAPO-36)

Using the same reagents and mixing procedure as in Example 40, above, a reaction mixture having a composition in terms of molar oxide ratios was prepared:

$1.0C_9H_{21}N:0.167MgO:0.917Al_2O_3:P_2O_5:40H_2O$.

The reaction mixture was sealed in a stainless steel pressure vessel and heated at 150° C. for 72 hours. The solid product was recovered by filtration, washed with water, and dried in air at room temperature. A portion of the solid was subjected to X-ray analysis. This solid had an X-ray powder diffraction pattern characterized by the following data:

TABLE N

| 2θ | d, (A) | 100 × I/I$_o$ |
|---|---|---|
| 7.9 | 11.2 | 100 |
| 8.2 | 10.8 | Shoulder |
| 13.5 | 6.56 | 5 |
| 15.8 | 5.61 | 12 |
| 16.4 | 5.40 | 38 |
| 19.0 | 4.67 | 55 |
| 20.8 | 4.27 | 39 |
| 21.4 | 4.15 | Shoulder |
| 21.8 | 4.08 | Shoulder |
| 22.0 | 4.04 | 33 |
| 22.4 | 3.97 | 32 |
| 22.8 | 3.90 | 12 |
| 23.8 | 3.74 | 8 |
| 27.2 | 3.28 | 13 |
| 27.6 | 3.23 | Shoulder |
| 28.2 | 3.16 | 9 |
| 28.8 | 3.10 | 9 |
| 30.2 | 2.97 | 7 |
| 31.8 | 2.814 | 8 |
| 33.0 | 2.714 | 3 |
| 34.6 | 2.592 | 13 |

Chemical analysis showed 31.8 wt.% $Al_2O_3$, 46.5 wt.% $P_2O_5$, 2.4 wt.% MgO, 7.9 wt.% C, 1.0 wt.% N, and 18.4 wt.% LOI, giving a product composition in molar oxide ratios of:

$0.22C_9H_{21}N:0.18MgO:0.95Al_2O_3:P_2O_5:0.44H_2O$ (b) A portion of the solid was calcined in air at 600° C. for 2 hours. The calcined solid exhibited an X-ray powder diffraction pattern essentially identical to that in Table "O", infra.

(c) Adsorption capacities were measured on the calcined solid using a standard McBain-Bakr gravimetric adsorption apparatus. The data was obtained on a sample activated at 350° C.

| Adsorbate | Kinetic Diameter, A | Pressure, Torr | Temp., °C. | Wt. % Adsorbed |
|---|---|---|---|---|
| O$_2$ | 3.46 | 101 | −183 | 18.9 |
| O$_2$ | 3.46 | 713 | −183 | 23.5 |
| Neopentane | 6.2 | 745 | 23 | 6.4 |
| n-butane | 4.3 | 712.0 | 23 | 7.3 |
| Cyclohexane | 6.0 | 73.0 | 23 | 9.1 |
| n-hexane | 4.3 | 105.0 | 23 | 10.5 |
| H$_2$O | 2.65 | 4.6 | 23 | 22.2 |
| H$_2$O | 2.65 | 20 | 23 | 31.1 |
| CO$_2$ | 3.3 | 297 | −82 | 22.0 |

EXAMPLE 42

(Preparation of MAPO-36)

(a) The procedure and gel composition of Example 41, above, was repeated. A portion of the solid product exhibited an X-ray powder diffraction pattern essentially identical to that in Table N, supra. Elemental analysis showed 33.1 wt.% $Al_2O_3$, 49.0 wt.% $P_2O_5$, 2.5 wt.% MgO, 8.5 wt.% C, 1.0 wt.% N, and 14.4 wt.% LOI, giving a product composition in molar oxide ratios of:

$0.21C_9H_{21}N:0.18MgO:0.94Al_2O_3:P_2O_5:0.17H_2O$.

(b) A portion of the solid product of part (a) was calcined at 600° C. for 2 hours. The calcined solid had an X-ray powder diffraction pattern characterized by the following data

TABLE O

| 2θ | d, (A) | 100 × I/I$_o$ |
|---|---|---|
| 7.8 | 11.3 | 100 |
| 8.2 | 10.8 | 40 |
| 13.5 | 6.56 | 10 |
| 15.9 | 5.57 | 5 |
| 16.5 | 5.37 | 27 |
| 19.2 | 4.62 | 41 |
| 20.7 | 4.29 | 25 |
| 21.4 | 4.15 | Shoulder |
| 21.8 | 4.08 | 12 |
| 22.2 | 4.00 | 23 |
| 22.3 | 3.99 | Shoulder |
| 23.0 | 3.87 | 5 |
| 23.8 | 3.74 | 5 |
| 27.1 | 3.29 | 16 |
| 27.5 | 3.24 | Shoulder |
| 28.3 | 3.15 | 6 |
| 29.0 | 3.08 | 8 |
| 30.3 | 2.95 | 5 |
| 31.8 | 2.814 | 8 |
| 34.8 | 2.577 | 11 |
| 35.8 | 2.508 | 3 |

(c) Chemical analysis of the calcined product of part (b) showed 30.4 wt.% $Al_2O_3$, 44.9 wt.% $P_2O_5$, 2.5 wt.% MgO, 21.3 wt.% LOI, giving a product composition in molar oxide ratios of:

$0.20MgO:0.94Al_2O_3:1.00P_2O_5:3.7H_2O$, or alternatively $(Mg_{0.05}Al_{0.46}P_{0.49})O_2$.

(d) Approximately 0.8 gram of the calcined solid of part (b) was slurried in 3.4N NaCl solution and stirred for 10 minutes at room temperature. The solid was recovered by filtration, washed with water, and dried in air at 110° C. A portion of the treated solid exhibited an X-ray powder diffraction pattern essentially identical to that of the starting material (Table O) Chemical analysis of the solid showed 35.9 wt.% $Al_2O_3$, 52.9 wt.% $P_2O_5$, 2.4 wt.% MgO, and 0.30 wt.% $Na_2O$, giving a product composition (dry basis) in molar oxide ratios of:

$0.013Na_2O:0.16MgO:0.94Al_2O_3:P_2O_5$.

(e) 1.03 grams of the calcined solid of part (b) was added to a solution containing 1.31 grams of silver nitrate (AgNO$_3$) in 50.0 grams of water and stirred for 15 minutes at room temperature. The solid was recovered by filtration, washed with water, and dried in air at room temperature. The resulting solid was suspended in a solution composed of 1.01 grams AgNO$_3$ in 50.0 grams of H$_2$O and slurried for approximately 60 minutes at room temperature, then was recovered by filtration, washed with water, and dried in air at room temperature. The final solid product exhibited an X-ray powder diffraction pattern characterized by the following data:

TABLE P

| 2θ | d, (A) | 100 × I/I$_o$ |
|---|---|---|
| 7.8 | 11.3 | 100 |

TABLE P-continued

| 2θ | d, (A) | 100 × I/I₀ |
|---|---|---|
| 8.1 | 10.2 | Shoulder |
| 13.4 | 6.61 | 12 |
| 15.8 | 5.61 | Shoulder |
| 16.4 | 5.41 | 18 |
| 19.1 | 4.65 | 29 |
| 20.7 | 4.29 | 24 |
| 22.3 | 3.99 | 32 |
| 23.4 | 3.80 | Shoulder |
| 23.8 | 3.74 | 12 |
| 27.2 | 3.28 | 24 |
| 28.2 | 3.16 | 12 |
| 29.0 | 3.08 | 15 |
| 30.4 | 2.94 | 9 |
| 31.8 | 2.814 | 9 |
| 34.7 | 2.585 | 9 |

Chemical analysis of the AgNO₃ treated solid after drying in air at 70° C. showed 30.2 wt.% Al₂O₃, 44.9 wt.% P₂O₅, 2.2 wt.% MgO, and 0.95 wt.% Ag, giving a product composition (dry basis) in molar oxide ratios of:

$0.014Ag_2O:0.17MgO:0.94Al_2O_3:P_2O_5$.

EXAMPLE 43

(Preparation of MAPO-36)

A reaction mixture was prepared by combining 53.4 grams of 85% orthophosphoric acid and 66.3 grams of water, to which was added 16.3 grams of a hydrated aluminum oxide (I), and to the mixture thus formed was added a solution prepared by dissolving 21.4 grams of magnesium acetate tetrahydrate in 45.2 grams of H₂O. To the resulting mixture 28.7 grams of tripropylamine (C₉H₂₁N) was added and stirred until homogeneous. The composition of the final reaction mixture in molar oxide ratios was:

$1.0C_9H_{21}N:0.5MgO:0.6Al_2O_3:1.2P_2O_5°:39.5-H_2O:CH_3COOH$.

The reaction mixture was sealed in a stainless steel pressure vessel and heated at 200° C. for 24 hours. The solid product was recovered by filtration, washed with water and dried in air at room temperature. By X-ray analysis, the solid was found to be impure, but the major phase had an X-ray powder diffraction pattern essentially identical to that of Table N, supra.

EXAMPLE 44

(Preparation of MAPO-36)

A procedure similar to that of Example 41 was followed using tetrapropylammonium hydroxide (TPAOH) as the templating agent. The composition of the final reaction mixture in molar oxide ratios was $TPAOH:0.40MgO:0.80Al_2O_3:P_2O_5:40H_2O$.

The solid product was impure but contained a phase characterized by an X-ray powder diffraction pattern essentially identical to that of TABLE N.

EXAMPLE 45

(Preparation of MAPO-36)

Using the same reagents and procedure as in Example 43, supra except that cyclohexylamine (C₆H₁₃N) was used as the templating agent instead of tripropylamine, MAPO-36 was crystallized from a reaction mixture having a composition in terms of molar oxide ratios of:

$C_6H_{13}N:0.40MgO:0.80Al_2O_3:P_2O_5:39.6H_2O:0.80CH_3COOH$.

The reaction mixture was sealed in a stainless steel pressure vessel and heated at 200° C. for 24 hours. The solids were recovered by filtration, washed with water, and dried in air at room temperature. A portion of the solid that was passed through a 60 mesh screen was found to be impure by X-ray analysis, but contained a phase characterized by the X-ray powder diffraction pattern of TABLE N.

The species MAPO-36 as referred to herein is a magnesium aluminophosphate material having a three-dimensional microporous crystal framework structure of PO₂⁺, AlO₂⁻ and MgO⁻² tetrahedral units, units, and whose essential empirical chemical composition on an anhydrous basis is:

$mR:(Mg_xAl_yP_z)O_2$ where "R" represents at least one organic templating agent present in the intracrystalline pore system; "m" represents the moles of "R" present per mole of $(Mg_xAl_yP_z)O_2$ and has a value of from zero to 0.3, "x", "y" and "z" represent respectively, the mole fractions of magnesium, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said magnesium aluminophosphate having a characteristic X-ray powder diffraction pattern which contains at least the d-spacings set forth below in TABLE XII. In the form as synthesized in accordance with the process of this invention, "m" has a value of from 0.02 to 0.3.

TABLE XII

| 2θ | d, (A) | Relative Intensity |
|---|---|---|
| 7.7–7.9 | 11.5–11.2 | vs |
| 16.2–16.6 | 5.47–5.34 | w–m |
| 18.9–19.3 | 4.70–4.60 | m–s |
| 20.6–20.8 | 4.31–4.27 | w–s |
| 21.8–22.0 | 4.08–4.04 | m |
| 22.2–22.5 | 4.00–3.95 | w–m |

All of the as-synthesized MAPO-36 compositions for which X-ray powder diffraction data have presently been obtained have X-ray patterns within the generalized pattern of Table XII (a), below:

TABLE XII (a)

| 2θ | d, (A) | 100 × I/Io |
|---|---|---|
| 7.7–7.9 | 11.5–11.2 | 100 |
| 8.0–8.2 | 11.1–10.8 | shoulder |
| 13.4–13.7 | 6.61–6.46 | 5–13 |
| 15.7–15.8 | 5.64–5.61 | 12–14 |
| 16.2–16.6 | 5.47–5.34 | 20–41 |
| 18.9–19.3 | 4.70–4.60 | 41–55 |
| 20.6–20.8 | 4.31–4.27 | 18–55 |
| 21.2–21.4 | 4.19–4.15 | shoulder |
| 21.8–22.0 | 4.08–4.04 | 33–47 |
| 22.2–22.5 | 4.00–3.95 | 30–43 |
| 22.7–23.4 | 3.92–3.80 | 11–16 |
| 23.5–23.8 | 3.79–3.74 | 8–15 |
| 27.0–27.3 | 3.30–3.27 | 13–27 |
| 27.5–27.6 | 3.24–3.23 | shoulder |
| 28.1–28.4 | 3.18–3.14 | 9–18 |
| 28.7–29.1 | 3.11–3.07 | 8–15 |
| 29.9–30.2 | 2.99–2.96 | 7–10 |
| 31.7–32.0 | 2.823–2.797 | 8–14 |
| 32.9–33.2 | 2.722–2.698 | 3–4 |
| 34.5–34.8 | 2.600–2.578 | 11–20 |

EXAMPLE 46

(Preparation of MAPO-39)

A structural species of the present invention denominated MAPO-39 was synthesized by the following procedure:

A first mixture was prepared by combining 46.2 grams of 85% orthophosphoric acid and 92.6 grams of water, to which was added 24.9 grams of a hydrated aluminum oxide (I). A solution prepared by dissolving 7.2 grams of magnesium acetate tetrahydrate in 25.0 grams of H$_2$O was added to this first mixture and to the resulting mixture 20.2 grams of dipropylamine (C$_6$H$_{15}$N) was added and stirred until homogeneous. The composition of the final reaction mixture in molar oxide ratios was:

C$_6$H$_{15}$N:0.167MgO:0.917Al$_2$O$_3$:P$_2$O$_5$:39.8-H$_2$O:0.33CH$_3$COOH.

The reaction mixture was placed in a sealed stainless steel pressure vessel and heated at 150° C. for 24 hours. The solid product was recovered by filtration, washed with water, and dried in air at room temperature. A portion of the solids passing through a 60 mesh screen was found to be impure, but the major phase had an X-ray powder diffraction pattern essentially identical to that of TABLE Q, infra.

EXAMPLE 47

(Preparation of MAPO-39)

(a) Using the same reagents and mixing procedures as in Example 46, supra, a reaction mixture was prepared having the composition:

C$_6$H$_{15}$N:0.4MgO:0.8Al$_2$O$_3$:P$_2$O$_5$:39.6H$_2$O:0.80CH$_3$COOH.

The reaction mixture was sealed in a stainless steel pressure vessel and heated at 150° C. for 24 hours. The solid product was recovered by filtration, washed with water, and dried in air at room temperature. A portion of the solids passing through a 60 mesh screen was subjected to X-ray and chemical analysis. This solid had an X-ray powder diffraction pattern characterized by the following data:

TABLE Q

| 2θ | d, (A) | 100 × I/I$_o$ |
|---|---|---|
| 9.4 | 9.41 | 28 |
| 13.3 | 6.66 | 49 |
| 18.0 | 4.93 | 44 |
| 21.2 | 4.19 | 82 |
| 22.5 | 3.95 | 100 |
| 26.9 | 3.31 | 4 |
| 28.6 | 3.12 | 10 |
| 29.6 | 3.02 | 17 |
| 30.2 | 2.96 | 39 |
| 32.6 | 2.75 | 14 |
| 33.8 | 2.65 | 10 |
| 36.5 | 2.46 | 3 |
| 38.0 | 2.368 | 10 |
| 40.9 | 2.206 | 3 |
| 46.0 | 1.973 | 3 |
| 48.6 | 1.873 | 4 |
| 49.2 | 1.852 | 4 |
| 51.3 | 1.781 | 4 |

By chemical analysis the composition was found to contain 30.6 wt.% Al$_2$O$_3$, 47.9 wt.% P$_2$O$_5$, 4.8 wt.% MgO, 5.2 wt.%C, 0.99 wt.%N and 16.2 wt.% LOI, giving a product composition in molar oxide ratios of:

0.21C$_6$H$_{15}$N:0.35MgO:0.89Al$_2$O$_3$:P$_2$O$_5$: 1.47H$_2$O, or alternatively 0.05C$_6$H$_{15}$N:(Mg$_{0.08}$Al$_{0.43}$P$_{0.48}$)O$_2$:0.36H$_2$O.

(b) A portion of the solid was calcined in air at 500° C. for 48 hours. The calcined product exhibited an X-ray powder diffraction pattern characterized by the following data wherein "I" is the intensity and "d" the interplanar spacing:

TABLE R

| 2θ | d, (A) | 100 × I/I$_o$ |
|---|---|---|
| 9.7 | 9.12 | 32 |
| 13.7 | 6.46 | 100 |
| 18.6 | 4.77 | 50 |
| 21.6 | 4.11 | 60 |
| 23.1 | 3.85 | 87 |
| 27.4 | 3.25 | 10 |
| 29.1 | 3.07 | 14 |
| 30.2 | 2.96 | 22 |
| 30.7 | 2.91 | 33 |
| 33.2 | 2.698 | 16 |
| 34.7 | 2.585 | 9 |
| 37.4 | 2.404 | 3 |
| 38.6 | 2.332 | 8 |
| 41.5 | 2.176 | 2 |
| 46.4 | 1.957 | 3 |
| 49.3 | 1.848 | 3 |
| 52.0 | 1.759 | 4 |

(c) Adsorption capacities were measured on this calcined product using a standard McBain-Bakr gravimetric adsorption apparatus. The following data were obtained on a sample activated at 360° C.

| Adsorbate | Kinetic Diameter, A | Pressure, Torr | Temp., °C. | Wt. % Adsorbed |
|---|---|---|---|---|
| O$_2$ | 3.46 | 102 | −183 | 8.2 |
| O$_2$ | 3.46 | 706 | −183 | 10.0 |
| cyclohexane | 6.0 | 74 | 25 | 0.44 |
| n-butane | 4.3 | 705 | 24 | 0.43 |
| xenon | 4.0 | 750 | 24 | 9.3 |
| neopentane | 6.2 | 701 | 24 | 0 |
| H$_2$O | 2.65 | 4.6 | 24 | 17.6 |
| H$_2$O | 2.65 | 22 | 24 | 22.8 |

EXAMPLE 48

(Preparation of MAPO-39)

Using the same reagents and mixing procedures as in Example 47, supra, except that isopropylamine was substituted for the dipropylamine of the earlier experiment, a reaction mixture having the following composition was prepared:

1.0C$_3$H$_9$N:0.04MgO:0.80Al$_2$O$_3$:P$_2$O$_5$:39.6-H$_2$O:0.80CH$_3$COOH.

The reaction mixture was sealed in a stainless steel pressure vessel and heated at 200° C. for 24 hours. The solid product was recovered by filtration, washed with water and dried in air at room temperature. A portion of the solids passing through a 60 mesh screen was found, by X-ray analysis, to be impure, but the major phase had an X-ray power diffraction pattern essentially identical to that of TABLE Q, above.

The species MAPO-39 as referred to herein is a magnesium aluminophosphate material having a three-dimensional microporous crystal framework structure of PO$_2$+, AlO$_2$− and MgO$^{-2}$ tetrahedral units, and whose essential empirical chemical composition on an anhydrous basis is:

mR:(Mg$_x$Al$_y$P$_z$)O$_2$ wherein "R" represents at least one organic templating agent present in the intracrystalline pore system; "m" represents the moles of "R" present per mole of $(Mg_xAl_yP_z)O_2$ and has a value of from zero to 0.3, "x", "y" and "z" represent respectively, the mole fractions of magnesium, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said magnesium aluminophosphate having a characteristic X-ray powder diffraction pattern which contains at least the d-spacings set forth below in TABLE XIII. In the form as synthesized in accordance with the process of this invention, "m" has a value of from 0.02 to 0.3.

TABLE XIII

| 2θ | d, (A) | Relative Intensity |
|---|---|---|
| 9.4–9.6 | 9.41–9.21 | w–m |
| 13.3–13.6 | 6.66–6.51 | m–vs |
| 18.0–18.4 | 4.93–4.82 | m |
| 21.2–21.5 | 4.19–4.13 | m–s |
| 22.5–23.0 | 3.95–3.87 | s–vs |
| 30.2–30.5 | 2.96–2.93 | w–m |

All of the as-synthesized MAPO-39 compositions for which X-ray powder diffraction data have presently been obtained, have X-ray patterns within the generalized pattern of Table XIII (a) below:

TABLE XIII (a)

| 2θ | d, (A) | 100 × I/Io |
|---|---|---|
| 9.4–9.6 | 9.41–9.21 | 28–45 |
| 13.3–13.6 | 6.66–6.51 | 40–100 |
| 18.0–18.4 | 4.93–4.82 | 31–44 |
| 21.2–21.5 | 4.19–4.13 | 49–82 |
| 22.5–23.0 | 3.95–3.87 | 71–100 |
| 26.9–27.2 | 3.31–3.28 | 4–8 |
| 28.6–29.0 | 3.12–3.08 | 8–14 |
| 29.6–30.0 | 3.02–2.98 | 15–18 |
| 30.2–30.5 | 2.96–2.93 | 23–39 |
| 32.6–33.0 | 2.747–2.714 | 12–17 |
| 33.7–34.5 | 2.660–2.600 | 6–14 |
| 38.0–38.6 | 2.368–2.332 | 6–10 |
| 48.6–48.8 | 1.873–1.866 | 4 |
| 51.3–51.9 | 1.781–1.762 | 4–7 |

EXAMPLE 49

(Preparation of MAPO-44)

A magnesium aluminophosphate species of the present invention denominated as MAPO-44 was prepared by the following procedure: A first mixture was prepared by combining 46.3 grams of 85% orthophosphoric acid and 77 grams of water, to which was added 19.1 grams of a hydrated aluminum oxide (I). A solution was prepared by dissolving 25.7 grams of magnesium acetate tetrahydrate in 35.8 grams of water, and then combined with the first mixture. To the resulting mixture was added 19.9 grams of cyclohexylamine ($C_6H_{13}N$) to form the final reaction mixture which had a composition in terms of molar oxide ratios of:

$C_6H_{13}N:0.6MgO:0.7Al_2O_3:P_2O_5:1.2CH_3COOH:39H_2O$.

The reaction mixture was crystallized at 150° C. for 24 hours in a sealed stainless steel reactor. The solids were recovered by filtration, washed with $H_2O$, and dried in air at room temperature. A portion of the solid that passed through a 100 mesh screen and was retained on a 200 mesh screen was submitted for X-ray analysis and chemical analysis. The solid had an X-ray powder diffraction pattern characterized by the following data:

TABLE S

| 2θ | d, (A) | 100 × I/I$_o$ |
|---|---|---|
| 9.5 | 9.31 | 100 |
| 13.0 | 6.81 | 6 |
| 13.8 | 6.42 | 1 |
| 15.8 | 5.61 | Shoulder |
| 16.1 | 5.50 | 13 |
| 17.3 | 5.13 | 1 |
| 19.0 | 4.67 | 14 |
| 20.7 | 4.29 | 81 |
| 21.6 | 4.11 | 13 |
| 22.5 | 3.95 | 5 |
| 23.0 | 3.87 | 5 |
| 24.3 | 3.66 | 15 |
| 26.0 | 3.43 | 8 |
| 27.7 | 3.22 | 5 |
| 29.6 | 3.02 | 6 |
| 30.0 | 2.98 | 5 |
| 30.7 | 2.91 | 42 |
| 32.4 | 2.76 | 1 |
| 32.8 | 2.73 | 1 |
| 34.7 | 2.585 | 1 |
| 35.4 | 2.536 | 6 |
| 38.4 | 2.344 | 2 |
| 39.8 | 2.265 | 2 |
| 42.0 | 2.151 | 3 |
| 43.4 | 2.085 | 3 |
| 47.0 | 1.933 | 1 |
| 47.9 | 1.899 | 3 |
| 48.5 | 1.877 | 15 |
| 49.1 | 1.855 | 7 |
| 53.5 | 1.713 | 8 |

Chemical analysis showed 23.4 wt.% $Al_2O_3$, 45.5 wt.% $P_2O_5$, 7.2 wt.% MgO, 13.6 wt.% C, 2.5 wt.% N, and 22.0 wt.% LOI, giving a product composition in molar oxide ratios of:

$0.59C_6H_{13}N:0.55MgO:0.72Al_2O_3:P_2O_5:0.57H_2O$.

On an anhydrous basis this composition corresponds to $0.15C_6H_{13}N:(Mg_{0.14}Al_{0.36}P_{0.50})O_2$.

EXAMPLE 50

(Preparation of MAPO-44)

(a) A procedure identical to that of Example 49 was followed except that the reaction mixture was heated at 200° C. at autogenous pressure for 24 hours. The solids were recovered by filtration, washed with $H_2O$ and dried in air at room temperature. A portion of the solid that passed through a 60 mesh screen exhibited an X-ray powder diffraction pattern similar to that of TABLE S. This solid was further ground in a mortar and pestle until it passed through a 325 mesh screen. The solid had an X-ray powder diffraction pattern characterized by the following data:

TABLE T

| 2θ | d, (A) | 100 × I/I$_o$ |
|---|---|---|
| 9.4 | 9.41 | 86 |
| 13.0 | 6.81 | 17 |
| 13.8 | 6.42 | 3 |
| 16.1 | 5.50 | 32 |
| 17.4 | 5.10 | 5 |
| 19.0 | 4.67 | 9 |
| 20.7 | 4.29 | 100 |
| 21.7 | 4.10 | 35 |
| 22.6 | 3.93 | 8 |
| 23.0 | 3.87 | 14 |
| 24.3 | 3.66 | 56 |
| 26.1 | 3.41 | 17 |
| 27.8 | 3.21 | 10 |
| 29.6 | 3.02 | Shoulder |
| 30.0 | 2.98 | 17 |

TABLE T-continued

| 2θ | d, (A) | 100 × I/I₀ |
|---|---|---|
| 30.8 | 2.90 | 54 |
| 32.4 | 2.76 | 4 |
| 32.8 | 2.73 | 4 |
| 35.5 | 2.53 | 9 |
| 38.4 | 2.344 | 1 |
| 39.1 | 2.304 | 1 |
| 39.8 | 2.265 | 1 |
| 40.1 | 2.249 | 4 |
| 40.4 | 2.233 | 3 |
| 43.6 | 2.076 | 3 |
| 47.1 | 1.929 | 1 |
| 48.0 | 1.895 | 6 |
| 48.6 | 1.873 | 5 |
| 50.2 | 1.817 | 8 |
| 53.7 | 1.707 | 5 |

Comparison of the X-ray intensities of Examples 49 and 50 indicates that the line intensities in Example 49 probably reflect preferred orientation of the rhombohedral crystals before grinding.

(b) A portion of the product of part (a) above was heated under vacuum at 425° C. for 16 hours in a standard McBain-Bakr gravimetric apparatus, and thereafter the following adsorption data obtained:

| Adsorbate | Kinetic Diameter, A | Pressure. Torr | Temp., °C. | Wt. % Adsorbed |
|---|---|---|---|---|
| Oxygen | 3.46 | 12 | −183 | 14.0 |
|  |  | 704 | −183 | 16.2 |
| Butane | 4.3 | 692 | 21 | 1.4 |
| Xenon | 4.0 | 754 | 23 | 12.4 |
| Water | 2.65 | 20 | 23 | 19.2 |

The pore diameter of the heat-treated product was found to be about 4.0 A as indicated by the adsorption of xenon and nil adsorption of butane.

The species MAPO-44 as referred to herein is a magnesium aluminophosphate material having a three-dimensional microporous crystal framework structure of $PO_2^+$, $AlO_2^-$ and $MgO^{-2}$ tetrahedral units, and whose essential empirical chemical composition on an anhydrous basis is:

$$mR:(Mg_xAl_yP_z)O_2$$

wherein "R" represents at least one organic templating agent present in the intracrystalline pore system; "m" represents the moles of "R" present per mole of $(Mg_xAl_yP_z)O_2$ and has a value of from zero to 0.3, "x", "y" and "z" represent respectively, the mole fractions of magnesium, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said magnesium aluminophosphate having a characteristic X-ray power diffraction pattern which contains at least the d-spacings set forth below in TABLE XIV. In the form as synthesized in accordance with the process of this invention, "m" has a value of from 0.02 to 0.3.

TABLE XIV

| 2θ | d, (A) | Relative Intensity |
|---|---|---|
| 9.4 | 9.41 | vs |
| 16.1 | 5.50 | m |
| 20.7 | 4.29 | vs |

TABLE XIV-continued

| 2θ | d, (A) | Relative Intensity |
|---|---|---|
| 21.7 | 4.10 | m |
| 24.3 | 3.66 | s |
| 30.8 | 2.90 | s |

EXAMPLE 51

(Preparation of MAPO-47)

(a) The species MAPO-47 was prepared as follows: A solution, prepared by dissolving 7.2 grams magnesium acetate tetrahydrate in 88.2 grams of H₂O, was added to 74.9 grams of aluminum isopropoxide. This mixture was homogenized at high speed in a blender until it was too viscous to be further blended. To this mixture was added a solution prepared by combining 46.2 grams of 85 wt.% orthophosphoric acid, 46.9 grams of N,N-diethylethanolamine (C₆H₁₅NO), and 46.3 grams of water. The resulting mixture was blended at high speed until homogenous. The composition of the mixture in molar oxide ratios was:

2.0C₆H₁₅NO:0.167MgO:0.917Al₂O₃:P₂O₅:0.33CH₃COOH:5.5C₃H₇OH:40H₂O.

The reaction mixture was sealed in a stainless steel pressure vessel and heated in an oven at 150° C. for 144 hours. The product mixture was freed of unreacted gel by centrifugation and washing with water. The final product was dried in air at ambient temperature. A portion of the product solids was subjected for X-ray and chemical analysis. The solid had an X-ray powder diffraction pattern characterized by the following data:

TABLE U

| 2θ | d, (A) | 100 × I/I₀ |
|---|---|---|
| 9.4 | 9.41 | 100 |
| 12.9 | 6.86 | 8 |
| 13.9 | 6.37 | 3 |
| 16.0 | 5.54 | 18 |
| 17.6 | 5.04 | 4 |
| 19.0 | 4.67 | 4 |
| 20.6 | 4.31 | 55 |
| 21.8 | 4.08 | 5 |
| 23.0 | 3.87 | 7 |
| 24.7 | 3.60 | 13 |
| 25.9 | 3.44 | 11 |
| 27.6 | 3.23 | 4 |
| 29.4 | 3.04 | 4 |
| 30.5 | 2.93 | 24 |
| 30.8 | 2.90 | Shoulder |
| 34.4 | 2.61 | 3 |
| 35.7 | 2.515 | 2 |
| 48.6 | 1.873 | 5 |
| 50.4 | 1.811 | 3 |
| 53.1 | 1.725 | 3 |

The product was found to contain 5.3 wt.% MgO, 24.5 wt.% Al₂O₃, 43.9 wt.% P₂O₅, 25.2 wt.% LOI, 10.0 wt.% C, and 2.0 wt.% N, giving a product composition in terms of molar oxide ratios of:

0.45C₆H₁₅NO:0.43MgO:0.78Al₂O₃:P₂O₅:2.0H₂O, or in terms of TO₂ units, an essential empirical formula (anhydrous basis);

0.11C₆H₁₅NO:(Mg₀.₁₁Al₀.₃₉P₀.₅₀)O₂.

(b) A portion of the product of part (a), above, was heated in air from a temperature of 100° C. up to 500° C. at a rate of 100° C./hour, and then held at 500° C. for 4 hours. The resulting calcined product exhibited an X-ray powder diffraction pattern characterized by the following data:

TABLE W

| 2θ | d, (A) | 100 × I/I$_o$ |
|---|---|---|
| 9.6 | 9.21 | 100 |
| 13.0 | 6.81 | 15 |
| 14.1 | 6.28 | 2 |
| 16.2 | 5.47 | 10 |
| 18.1 | 4.90 | 7 |
| 19.3 | 4.60 | 2 |
| 20.8 | 4.27 | 30 |
| 22.4 | 3.97 | 2 |
| 23.3 | 3.82 | 2 |
| 25.3 | 3.52 | 7 |
| 26.1 | 3.41 | 7 |
| 28.5 | 3.13 | 1 |
| 30.9 | 2.89 | 12 |
| 31.4 | 2.849 | 9 |

(c) A portion of the product of part (b) was calcined in vacuum at 500° C. for 4 hours. The calcined product had an X-ray powder diffraction pattern characterized by the following data.

TABLE W(a)

| 2θ | d, (A) | 100 × I/I$_o$ |
|---|---|---|
| 9.6 | 9.21 | 100 |
| 13.0 | 6.81 | 21 |
| 14.1 | 6.28 | 6 |
| 16.2 | 5.47 | 21 |
| 18.1 | 4.90 | 13 |
| 19.2 | 4.62 | 3 |
| 20.7 | 4.29 | 54 |
| 22.3 | 3.99 | 3 |
| 23.2 | 3.83 | 4 |
| 25.2 | 3.53 | 12 |
| 26.0 | 3.43 | 12 |
| 27.8 | 3.21 | 3 |
| 28.5 | 3.13 | 3 |
| 29.7 | 3.01 | 3 |
| 30.7 | 2.91 | 22 |
| 31.2 | 2.87 | 13 |
| 34.6 | 2.592 | 4 |
| 49.1 | 1.855 | 3 |

(d) Adsorption capacities of the product of part (c) were measured using a standard McBain-Bakr gravimetric apparatus. The following data were obtained using a sample activated at 350° C.:

| Adsorbate | Kinetic Diameter, A | Pressure, Torr | Temp., °C. | Wt. % Adsorbed |
|---|---|---|---|---|
| Oxygen | 3.46 | 12 | −183 | 17.6 |
|  |  | 704 | −183 | 21.5 |
| Butane | 4.3 | 692 | 21 | 4.0 |
| Xenon | 4.0 | 754 | 23 | 17.1 |
| H$_2$O | 2.65 | 20 | 23 | 27.4 |

The pore diameter of the calcined MAPO-47 was thus found to be about 4.3 A as indicated by the slow adsorption of butane and the rapid adsorption of xenon.

The species MAPO-47 as referred to herein is a magnesium aluminophosphate material having a three-dimensional microporous crystal framework structure of PO$_2^+$, AlO$_2^-$ and MgO$^{-2}$ tetrahedral units, tetrahedral units, and whose essential empirical chemical compositions on an anhydrous basis is:

mR:(Mg$_x$Al$_y$P$_z$)O$_2$ wherein "R" represents at least one organic templating agent present in the intracrystalline pore system; "m" represents the moles of "R" present per mole of (Mg$_x$Al$_y$P$_z$)O$_2$ and has a value of from zero to 0.3, "x", "y" and "z" represent respectively, the mole fractions of magnesium, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said magnesium aluminophosphate having a characteristic X-ray powder diffraction pattern which contains at least the d-spacings set forth below in TABLE XV. In the form as synthesized in accordance with the process of this invention, "m" has a value of from 0.02 to 0.3

TABLE XV

| 2θ | d, (A) | Relative Intensity |
|---|---|---|
| 9.4 | 9.41 | vs |
| 16.0 | 5.54 | w |
| 20.6 | 4.31 | s |
| 24.7 | 3.60 | w |
| 25.9 | 3.44 | w |
| 30.5 | 2.93 | w |

EXAMPLE 52

(Preparation of ZAPO-5 and ZAPO-11)

Two zinc aluminophosphate species of the present invention, ZAPO-5 and ZAPO-11, were crystallized in admixture from a reaction mixture prepared as follows: A first mixture was formed by combining 46.2 grams of 85% orthophosphoric acid and 93.4 grams of water, to which was added 25.2 grams of a hydrated aluminum oxide (II). A solution prepared by dissolving 7.34 grams of zinc acetate dihydrate in 25.1 grams of H$_2$O was added to this first mixture, and to the resulting mixture was added 20.2 grams of diisopropylamine (C$_6$H$_{15}$N) to form the final reaction mixture which had a composition in terms of molar oxide ratios of:

1.0C$_6$H$_{15}$N:0.167ZnO:0.917Al$_2$O$_3$:P$_2$O$_5$:39.8-H$_2$O:0.33CH$_3$COOH.

The reaction mixture was sealed in a stainless steel pressure vessel and heated at 200° C. for 24 hours. The solid product was recovered by centrifugation, then washed with water and dried in air at room temperature. A portion of the product solids that passed through 60 mesh screen was subjected to X-ray analysis. This solid had an X-ray powder diffraction pattern indicative of a mixture of the two species, ZAPO-5 and ZAPO-11, characterized by the following data:

TABLE Y

| (ZAPO-5) | | |
|---|---|---|
| 2θ | d, (A) | 100 × I/I$_o$ |
| 7.3 | 12.1 | 55 |
| 12.8 | 6.92 | 11 |
| 14.8 | 5.99 | 11 |
| 19.6 | 4.53 | 31 |
| 21.0 | 4.23 | 100 |
| 22.3 | 3.99 | 82 |
| 24.7 | 3.60 | Shared peak |
| 25.8 | 3.45 | 24 |
| 28.9 | 3.09 | 16 |
| 29.8 | 2.998 | 14 |
| 33.5 | 2.675 | 5 |
| 34.3 | 2.614 | Shared peak |
| 36.8 | 2.442 | 4 |
| 37.7 | 2.386 | Shared peak |
| 42.0 | 2.151 | 4 |
| 42.9 | 2.108 | 5 |

TABLE Y-continued

| 2θ | (ZAPO-5) d, (A) | 100 × I/I_o |
|---|---|---|
| 47.4 | 1.918 | 4 |

TABLE Z

| 2θ | (ZAPO-11) d, (A) | 100 × I/I_o |
|---|---|---|
| 8.1 | 10.9 | 36 |
| 9.4 | 9.41 | 72 |
| 13.1 | 6.76 | 18 |
| 15.7 | 5.64 | 38 |
| 19.0 | 4.67 | 13 |
| 20.2 | 4.40 | 49 |
| 22.7 | 3.92 | Shoulder |
| 23.1 | 3.85 | 100 |
| 24.7 | 3.60 | Shared peak |
| 26.4 | 3.38 | 46 |
| 28.1 | 3.18 | 10 |
| 28.7 | 3.11 | Shoulder |
| 29.6 | 3.02 | Shoulder |
| 31.5 | 2.84 | 18 |
| 32.7 | 2.739 | 21 |
| 34.3 | 2.614 | Shared peak |
| 37.7 | 2.386 | Shared peak |
| 44.6 | 2.032 | 8 |

Chemical analysis of the mixture showed 32.3 wt.% $Al_2O_3$, 49.2 wt.% $P_2O_5$, 5.1 wt.% ZnO, 5.7 wt.% C, 1.2 wt.% N, and 13.0 wt.% LOI, giving a product composition in molar oxide ratios of:

$0.23C_6H_{15}N:0.18ZnO:0.91Al_2O_3:P_2O_5:0.80H_2O$, or alternatively $0.06C_6H_{15}N:(Zn_{0.05}Al_{0.45}P_{0.50})O_2:0.20H_2O$.

EXAMPLE 53

(Preparation of ZAPO-5)

A solution of 7.3 grams of zinc (II) acetate dihydrate [$Zn(CH_3CO_2)_2 \cdot 2H_2O$] in 89.5 grams of water was added to 74.9 grams of aluminum isopropoxide and blended with vigorous agitation until a thick gel formed. To this gel was added a solution composed of 46.2 grams of 85% orthophosphoric acid, 46.2 grams of water and 46.9 grams of diethylethanolamine ($C_6H_{15}NO$) to produce the final reaction mixture which had a composition expressed in terms of molar oxide ratios of $2.0C_6H_{15}NO:0.167ZnO:0.917Al_2O_3:0.33CH_3COOH:5.5C_3H_7OH:40H_2O$.

The reaction mixture was heated in a sealed reactor at 200° C. for 24 hours. The solid product was isolated by filtration, washed with water and dried in air at room temperature. The product was found to be impure, but the major phase had an X-ray powder diffraction pattern characterized by the following data:

TABLE AA

| 2θ | d, (A) | 100 × I/I_o |
|---|---|---|
| 7.4 | 11.95 | 100 |
| 12.9 | 6.86 | shared peak |
| 15.0 | 5.91 | 19 |
| 19.8 | 4.48 | 46 |
| 20.8 | 4.27 | 43 |
| 22.4 | 3.97 | 75 |
| 24.4 | 3.65 | shared peak |
| 26.1 | 3.41 | shared peak |
| 29.0 | 3.08 | 12 |
| 30.2 | 2.959 | 21 |
| 33.7 | 2.660 | 4 |
| 34.8 | 2.578 | 14 |
| 37.1 | 2.423 | 4 |
| 37.6 | 2.392 | 9 |

EXAMPLE 54

(Preparation of ZAPO-5)

A first mixture was prepared by adding 27.1 grams of a hydrated aluminum oxide (I) to a solution of 46.1 grams of 85% orthophosphoric acid in 92.4 grams of water. A solution of 17.6 grams of zinc (II) acetate dihydrate in 63.0 grams of water was then added to the first mixture, and to the resulting mixture was added 19.8 grams of cyclohexylamine ($C_6H_{13}N$) to form the final reaction mixture which had a composition in terms of molar oxide ratios of:

$1.0C_6H_{13}N:0.4ZnO:0.8Al_2O_3:P_2O_5:0.8CH_3COOH:50H_2O$.

The reaction mixture was heated at 150° C. for 24 hours in a sealed reactor and the solid product isolated by filtration, washed with water and dried in air at room temperature. A portion of the wet solids that passed through a 200 mesh screen was found to be impure ZAPO-5, but the ZAPO-5 had an X-ray powder diffraction pattern essentially identical to that of Example 53, above.

The species ZAPO-5 as referred to herein is a zinc aluminophosphate material having a three-dimensional microporous crystal framework structure of $PO_2^+$, $AlO_2^-$ and $MgO^{-2}$ tetrahedral units, and whose essential empirical chemical composition on an anhydrous basis is:

$$mR:(Zn_xAl_yP_z)O_2$$ 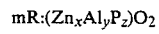

wherein "R" represents at least one organic templating agent present in the intracrystalline pore system; "m" represents the moles of "R" present per mole of $(Zn_xAl_yP_z)O_2$ and has a value of from zero to 0.3, "x", "y" and "z" represent respectively, the mole fractions of zinc, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said zinc aluminophosphate having a characteristic X-ray powder diffraction pattern which contains at least the d-spacings set forth below in TABLE XVI. In the form as synthesized in accordance with the process of this invention, "m" has a value of from 0.02 to 0.3.

TABLE XVI

| 2θ | d, (A) | Relative Intensity |
|---|---|---|
| 7.3–7.5 | 12.1–11.8 | s–vs |
| 14.8–15.0 | 5.99–5.91 | w |
| 19.6–19.9 | 4.53–4.46 | m–s |
| 20.8–21.0 | 4.27–4.23 | m–vs |
| 22.3–22.5 | 3.99–3.95 | s |

All of the as-synthesized ZAPO-5 compositions for which X-ray powder diffraction data have presently been obtained have patterns which are within the generalized pattern of TABLE XVII below:

TABLE XVII

| 2θ | d, (A) | Relative Intensity |
|---|---|---|
| 7.3–7.5 | 12.1–11.8 | s–vs |
| 12.8–13.0 | 6.92–6.81 | w |
| 14.8–15.0 | 5.99–5.91 | w |
| 19.6–19.9 | 4.53–4.46 | m–s |
| 20.8–21.0 | 4.27–4.23 | m–vs |
| 22.3–22.5 | 3.99–3.95 | s |
| 24.4–24.7 | 3.65–3.60 | shared |
| 25.8–26.1 | 3.45–3.41 | w |
| 28.9–29.0 | 3.09–3.08 | w |
| 29.8–30.2 | 3.00–2.96 | w |
| 33.5–33.7 | 2.675–2.660 | vw |
| 34.3–34.8 | 2.614–2.578 | w |
| 36.8–37.1 | 2.392–2.386 | vw |
| 37.6–37.7 | 2.442–2.423 | vw |
| 42.0–42.4 | 2.151–2.132 | vw |
| 47.4–48.0 | 1.918–1.895 | vw |

EXAMPLE 55

(Preparation of ZAPO-11)

A reaction mixture was prepared by combining 46.2 grams of 85% orthophosphoric acid and 92.6 grams of water, to which was added 21.7 grams of a hydrated aluminum oxide (I). A solution prepared by dissolving 17.6 grams of zinc (II) acetate dihydrate in 63.0 grams of $H_2O$ was added to the reaction mixture. To the resulting mixture 20.2 grams of dipropylamine ($C_6H_{15}N$) was added. The composition of the final reaction mixture in terms of molar oxide ratios was:

1.0$C_6H_{15}N$:0.4ZnO:0.8$Al_2O_3$:$P_2O_5$:0.8$CH_3COOH$:50$H_2O$.

The reaction mixture was heated at 200° C. for 24 hours in a sealed reactor. The solids were recovered by filtration, washed with water, and dried in air at room temperature. The overall product was found to be a mixture of phases, but the major phase had an X-ray powder diffraction pattern characterized by the following data:

TABLE BB

| 2θ | d, (A) | 100 × I/I₀ |
|---|---|---|
| 8.1 | 10.92 | 37 |
| 9.4 | 9.41 | 67 |
| 13.0 | 6.81 | 16 |
| 15.5 | 5.72 | 46 |
| 16.1 | 5.51 | 5 |
| 18.9 | 4.70 | 9 |
| 20.2 | 4.40 | 52 |
| 21.0 | 4.23 | 73 |
| 22.0 | 4.04 | 69 |
| 22.3 | 3.99 | 57 |
| 22.6 | 3.93 | 69 |
| 23.0 | 3.87 | 100 |
| 24.3 | 3.66 | 12 |
| 24.6 | 3.62 | 15 |
| 26.3 | 3.39 | 37 |
| 28.1 | 3.18 | 12 |
| 28.6 | 3.12 | 28 |
| 29.4 | 3.038 | 11 |
| 31.4 | 2.849 | 13 |
| 32.6 | 2.747 | 32 |
| 34.1 | 2.629 | 14 |
| 36.2 | 2.481 | 9 |
| 37.6 | 2.392 | 14 |
| 39.2 | 2.298 | 7 |
| 44.5 | 2.036 | 8 |
| 50.5 | 1.807 | 7 |

EXAMPLE 56

(Preparation of ZAPO-11)

Using the procedure of Example 53, above, and the same reagents and proportions thereof except 20.2 grams of diisopropylamine ($C_6H_{15}N$) were substituted for the 46.9 grams of diethylethanolamine used in the earlier example, a final reaction mixture was prepared having the composition in terms of molar oxide ratios of:

1.0$C_6H_{15}N$:0.167ZnO:0.917$Al_2O_3$:$P_2O_5$:0.33$CH_3COOH$:5.5i-$C_3H_7OH$:40$H_2O$.

The reaction mixture was heated at 200° C. for 168 hours in a sealed reactor. The solids were recovered by centrifugation, washed with water, and dried in air at room temperature. A portion of the solids was subjected to X-ray analysis. The overall solid product was found to be a mixture of ZAPO-11 and ZAPO-34, the former having an X-ray powder diffraction pattern essentially the same as in Example 55, supra.

The species ZAPO-11 as referred to herein is a zinc aluminophosphate material having a three-dimensional microporous crystal framework structure of $PO_2^+$, $AlO_2^-$ and $ZnO_2^{-2}$ tetrahedral units, and whose essential empirical chemical composition on an anhydrous basis is:

$$mR:(Zn_xAl_yP_z)O_2$$

wherein "R" represents at least one organic templating agent present in the intracrystalline pore system; "m" represents the moles of "R" present per mole of $(Zn_xAl_yP_z)O_2$ and has a value of from zero to 0.3, "x", "y" and "z" represent respectively, the mole fractions of zinc, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said zinc aluminophosphate having a characteristic X-ray powder diffraction pattern which contains at least the d-spacings set forth below in TABLE XVIII. In the form as synthesized in accordance with the process of this invention, "m" has a value of from 0.02 to 0.3.

TABLE XVIII

| 2θ | d, (A) | Relative Intensity |
|---|---|---|
| 9.4 | 9.41 | s |
| 15.5–15.7 | 5.72–5.64 | m–s |
| 20.2–20.3 | 4.40–4.37 | s |
| 21.0 | 4.23 | m–s |
| 22.0–22.1 | 4.04–4.02 | m–s |
| 23.0–23.1 | 3.87–3.85 | vs |

All of the as-synthesized ZAPO-11 compositions for which X-ray powder diffraction patterns have been obtained at present, have X-ray patterns within the generalized pattern of Table XVIII (a), below:

TABLE XVIII (a)

| 2θ | d, (A) | Relative Intensity |
|---|---|---|
| 8.1 | 10.92 | m |
| 9.4 | 9.41 | s |
| 13.0–13.1 | 6.81–6.76 | w |
| 15.5–15.7 | 5.72–5.64 | m–s |

TABLE XVIII-continued

| 2θ | d, (A) | Relative Intensity |
|---|---|---|
| 18.9–19.0 | 4.70–4.67 | m–w |
| 20.2–20.3 | 4.40–4.37 | s |
| 21.0 | 4.23 | m–s |
| 22.0–22.1 | 4.04–4.02 | m–s |
| 22.3–22.4 | 3.99–3.97 | m–s |
| 22.6–22.7 | 3.93–3.92 | m–s |
| 23.0–23.1 | 3.87–3.85 | vs |
| 24.3 | 3.66 | w |
| 24.6–24.7 | 3.62–3.60 | w |
| 26.3–26.4 | 3.39–3.38 | w–m |
| 28.1 | 3.18 | vw–m |
| 28.6–28.7 | 3.12–3.11 | w |
| 29.4–29.6 | 3.04–3.02 | w |
| 31.4–31.5 | 2.849–2.840 | w |
| 32.6–32.7 | 2.747–2.739 | w–m |
| 34.1–34.3 | 2.629–2.607 | w |
| 36.2–36.3 | 2.481–2.475 | vw |
| 37.6–37.8 | 2.392–2.380 | vw–w |
| 39.2 | 2.298 | vw |
| 44.5–44.6 | 2.036–2.032 | vw |
| 50.5–50.6 | 1.807–1.804 | vw |

(a)

EXAMPLE 57

(Preparation of ZAPO-14)

The MeAPO species denominated ZAPO-14 was prepared by combining a solution of 46.2 grams of 85% orthophosphoric acid in 92.2 grams of water with 24.9 grams of a hydrated aluminum oxide (I). A solution of 7.3 grams of zinc (II) acetate dihydrate in 65.6 grams of water was then added, followed by 11.8 grams of isopropylamine ($C_3H_9N$) to form the final reaction mixture which had a composition in terms of molar oxide ratios of $1.0C_3H_9N:0.167ZnO:0.917Al_2O_3:P_2O_5:0.33CH_3COOH:50H_2O$.

The reaction mixture was heated in a sealed reactor at 150° C. for 168 hours. The solids were recovered by filtration, washed with water, and dried in air at room temperature. A portion of the solids was subjected to X-ray analysis. The solid was impure but the major phase exhibited an X-ray powder diffraction pattern characterized by the following data:

TABLE CC

| 2θ | d, (A) | 100 × I/I$_o$ |
|---|---|---|
| 8.9 | 9.94 | 100 |
| 11.1 | 7.97 | 22 |
| 13.0 | 6.81 | 27 |
| 15.8 | 5.61 | 22 |
| 17.9 | 4.96 | 12 |
| 20.8 | 4.27 | 10 |
| 21.8 | 4.08 | 17 |
| 22.2 | 4.00 | 22 |
| 22.6 | 3.93 | 32 |
| 26.1 | 3.41 | 11 |
| 27.0 | 3.30 | 4 |
| 29.5 | 3.03 | 16 |
| 30.3 | 2.950 | 14 |
| 33.6 | 2.667 | 6 |

The species ZAPO-14 as referred to herein is a zinc aluminophosphate material having a three-dimensional microporous crystal framework structure of $PO_2^+$, $AlO_2^-$ and $ZnO_2^{-2}$ tetrahedral units, and whose essential empirical chemical composition on an anhydrous basis is:

$mR:(Zn_xAl_yP_z)O_2$ wherein "R" represents at least one organic templating agent present in the intracrystalline pore system; "m" represents the moles of "R" present per mole of $(Zn_xAl_yP_z)O_2$ and has a value of from zero to 0.3, "x", "y" and "z" represent respectively, the mole fractions of zinc, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said zinc aluminophosphate having a characteristic X-ray powder diffraction pattern which contains at least the d-spacings set forth below in TABLE XIX. In the form as synthesized in accordance with the process of this invention, "m" has a value of from 0.02 to 0.3.

TABLE XIX

| 2θ | d, (A) | Relative Intensity |
|---|---|---|
| 8.9 | 9.94 | vs |
| 11.1 | 7.97 | w |
| 13.0 | 6.81 | w |
| 15.8 | 5.61 | w |
| 22.2 | 4.00 | w |
| 22.6 | 3.93 | m |

EXAMPLE 58

(Preparation of ZAPO-34)

The zinc aluminophosphate species of the present invention denominated ZAPO-34 was prepared by first combining a solution of 23.1 grams of 85% orthophosphoric acid in 38.2 grams of water with 3.26 grams of ZnO. The resulting composition was then admixed with 11.0 grams of a hydrated aluminum oxide (II), and to this mixture was added 36.82 grams of aqueous 40% tetraethylammonium hydroxide (TEAOH). The composition of the reaction mixture in terms of molar oxide ratios was:

$1.0TEAOH:0.4ZnO:0.8Al_2O_3:P_2O_5:40H_2O$.

The reaction mixture was placed in an inert plastic screwcap bottle (polytetrafluorethylene) and heated in an oven at 100° C. at autogenous pressure for 68 hours. The solid product was washed three times by suspending in water, centrifuging, and decanting of the supernatant and then dried in air at room temperature. A portion of the solid product was subjected to X-ray analysis. It had an X-ray powder diffraction pattern characterized by the following data:

TABLE DD

| 2θ | d, (A) | 100 × I/I$_o$ |
|---|---|---|
| 9.5 | 9.31 | 99 |
| 12.9 | 6.86 | 21 |
| 14.0 | 6.33 | 15 |
| 16.0 | 5.54 | 45 |
| 17.8 | 4.98 | 24 |
| 20.5 | 4.33 | 100 |
| 22.2 | 4.00 | 7 |
| 22.9 | 3.88 | 7 |
| 25.0 | 3.56 | 36 |
| 25.7 | 3.47 | 26 |
| 27.5 | 3.24 | 12 |
| 28.2 | 3.16 | 13 |
| 29.5 | 3.03 | 12 |
| 30.5 | 2.93 | 55 |
| 31.1 | 2.876 | 36 |
| 34.3 | 2.614 | 14 |
| 36.1 | 2.488 | 10 |
| 39.5 | 2.281 | 5 |

TABLE DD-continued

| 2θ | d, (A) | 100 × I/I$_o$ |
|---|---|---|
| 42.8 | 2.113 | 5 |
| 47.4 | 1.918 | 6 |
| 48.8 | 1.866 | 8 |
| 50.6 | 1.804 | 6 |
| 53.0 | 1.728 | 5 |

EXAMPLE 59

(Preparation of ZAPO-34)

(a) ZAPO-34 was prepared by the procedure wherein a first mixture was prepared by combining 46.2 grams of 85% orthophosphoric acid, 38.3 grams of water and 22.0 grams of a hydrated aluminum oxide (II). A second mixture was formed by adding to the first mixture a solution of 17.6 grams of zinc acetate dihydrate in 71.2 grams of water. The final reaction mixture was formed by adding to the second mixture 73.6 grams of aqueous 40% tetraethylammonium hydroxide. The reaction mixture composition, in terms of molar oxide ratios, was:

1.0TEAOH:0.40ZnO:1.0Al$_2$O$_3$:1.0P$_2$O$_5$:49.6-H$_2$O:0.80CH$_3$COOH.

The reaction mixture was placed in an inert plastic screwcap bottle (polytetrafluoroethylene) and heated in an oven at 100° C. at autogenous pressure for 336 hours. The solid product was recovered by centrifugation, then filtered, washed with water and dried in air at room temperature. A portion of the solids that passed through a 120 mesh screen was subjected to X-ray analysis and chemical analysis. This solid had an X-ray powder diffraction pattern essentially identical to that of TABLE DD. supra. Chemical analysis showed 24.3 wt.% Al$_2$O$_3$, 40.5 wt.% P$_2$O$_5$, 11.8 wt.% ZnO, 9.0 wt% C, 1.5 wt.% N, and 21.5 wt.% LOI, giving a product composition in molar oxide ratios of:

0.33C$_8$H$_{21}$NO:0.50ZnO:0.84Al$_2$O$_3$:P$_2$O$_5$:1.3H$_2$O, or alternatively (0.08TEAOH:(Zn$_{0.12}$Al$_{0.40}$P$_{0.48}$)O$_2$:0.31H$_2$O.

(b) A portion of the solid of part (a) was heated in a vacuum oven at 150° C. for 19 hours to remove any adsorbed water. This activated sample was then stored in moist air at a constant relative humidity of 79% until there was essentially no further weight gain. This hydrated sample exhibited a weight gain of 7.6% based on the activated weight. X-ray analysis of the hydrated sample showed essentially no change in the X-ray powder pattern following this procedure.

EXAMPLE 60

(Preparation of ZAPO-34)

(a) A solution of 17.6 grams of zinc (II) acetate dihydrate in 143.4 grams of water was added to 65.4 grams of aluminum isopropoxide using high shear blending to produce a thick gel. To this gel was added incrementally 46.2 grams of 85% orthophosphoric acid, and the resulting mixture again blended with vigorous agitation. The final reaction mixture was formed by adding stepwise 73.6 grams of aqueous 40% tetraethylammonium hydroxide (TEAOH) followed by high shear blending. The composition of the final reaction mixture was:

1.0TEAOH:0.4ZnO:0.8Al$_2$O$_3$:P$_2$O$_5$:0.8CH$_3$COOH:55H$_2$O:4.8C$_3$H$_7$OH.

After crystallization at 100° C. for 96 hours in a sealed reactor, the solids were recovered by filtration, washed with water and dried in air at room temperature. A portion of the solids was subjected to X-ray analysis, the solid was pure, and had an X-ray powder diffraction pattern characterized by the following data:

TABLE EE

| 2θ | d, (A) | 100 × I/I$_o$ |
|---|---|---|
| 9.4 | 9.41 | 100 |
| 12.7 | 6.97 | 19 |
| 14.0 | 6.33 | 14 |
| 15.9 | 5.57 | 47 |
| 17.9 | 4.96 | 23 |
| 20.5 | 4.33 | 97 |
| 22.2 | 4.00 | 5 |
| 23.0 | 3.87 | 3 |
| 25.1 | 3.55 | 26 |
| 25.7 | 3.47 | 20 |
| 27.4 | 3.26 | 5 |
| 28.3 | 3.15 | 5 |
| 29.5 | 3.028 | 6 |
| 30.5 | 2.931 | 39 |
| 31.1 | 2.876 | 24 |
| 34.3 | 2.614 | 9 |
| 36.2 | 2.481 | 5 |
| 39.5 | 2.281 | 3 |
| 43.1 | 2.099 | 3 |
| 47.4 | 1.918 | 5 |
| 48.9 | 1.863 | 6 |
| 50.8 | 1.797 | 5 |

The product was established by chemical analysis to contain 24.4 wt. % Al$_2$O$_3$, 43.7 wt % P$_2$O$_5$, 9.4 wt. % ZnO, 9.6 wt. % C, 1.56 wt. % N and 21.7 wt. % LOI, giving an overall product composition in terms of molar oxide ratios of:

0.32TEAOH:0.38ZnO:0.78Al$_2$O$_3$:P$_2$O$_5$:1.57H$_2$O, or alternatively, in terms of moles of TEAOH per average mole of TO$_2$ units (anhydrous basis)

0.08TEAOH:(Zn$_{0.10}$Al$_{0.40}$P$_{0.50}$)O$_2$.

(b) A portion of the product of part (a) was calcined in vacuum at 500° C. for 5 hours. The calcined product had an X-ray powder diffraction pattern characterized by the following data:

| 2θ | d (A) | 100 I/I$_o$ |
|---|---|---|
| 9.6 | 9.21 | 100 |
| 13.0 | 6.81 | 28 |
| 14.2 | 6.24 | 4 |
| 16.2 | 5.47 | 22 |
| 18.1 | 4.90 | 15 |
| 20.8 | 4.27 | 43 |
| 25.3 | 3.52 | 17 |
| 26.1 | 3.41 | 15 |
| 28.5 | 3.13 | 4 |
| 30.8 | 2.90 | 26 |
| 31.4 | 2.85 | 15 |
| 34.7 | 2.585 | 4 |

(c) Adsorption capacities of the calcined composition of part (b) above were measured using a standard McBain-Bakr gravimetric apparatus. The following data was obtained on a sample activated at 375° C.

| Adsorbate | Kinetic Diameter, A | Pressure, Torr | Temp., °C. | Wt. % Adsorbed |
|---|---|---|---|---|
| Oxygen | 3.46 | 12 | −183 | 18.0 |
|  |  | 704 | −183 | 22.2 |
| Butane | 4.3 | 692 | 21 | 8.3 |
| Xenon | 4.0 | 754 | 23 | 17.5 |
| Water | 2.65 | 20 | 23 | 27.8 |

The pore diameter of the calcined product was about 4.3 A was indicated by the slow adsorption of butane and the rapid adsorption of xenon.

(d) EDAX (energy dispersion analysis by X-ray) microprobe analysis in conjunction with SEM (scanning electron microscope) study on clean crystals having a crystal morphology characteristic of ZAPO-34 gives the following analysis based on relative peak heights:

| | Average of Spot Probes |
|---|---|
| Zn | 0.03 |
| Al | 0.38 |
| P | 0.59 |

EXAMPLE 61

(Preparation of ZAPO-34)

Using the same reagents, proportions and procedures as in Example 57, supra, except that the crystallization period was limited to 24 rather than 168 hours, ZAPO-34 was produced in admixture with ZAPO-14.

The species ZAPO-34 as referred to herein is a zinc aluminophosphate material having a three-dimensional microporous crystal framework structure of $PO_2^+$, $AlO_2^-$ and $ZnO_2^{-2}$ tetrahedral units, and whose essential empirical chemical composition on an anhydrous basis is:

$$mR:(Zn_xAl_yP_z)O_2$$

wherein "R" represents at least one organic templating agent present in the intracrystalline pore system; "m" represents the moles of "R" present per mole of $(Zn_xAlP_z)O_2$ and has a value of from zero to 0.3, "x", "y" and "z" represent respectively, the mole fractions of zinc, aluminum and phosphorus present in the oxide moiety, said mole fractions being within the compositional area bounded by points A, B, C and D on the ternary diagram which is FIG. 1, or preferably within the area bounded by points a, b, c, and d on the ternary diagram which is FIG. 2, said zinc aluminophosphate having a characteristic X-ray powder diffraction pattern which contains at least the d-spacings set forth below in TABLE XX. In the form as synthesized in accordance with the process of this invention, "m" has a value of from 0.02 to 0.3.

TABLE XX

| 2θ | d, (A) | Relative Intensity |
|---|---|---|
| 9.4–9.5 | 9.41–9.31 | vs |
| 12.6–12.9 | 7.03–6.86 | vw–m |
| 15.9–16.0 | 5.57–5.34 | w–m |
| 20.3–20.5 | 4.37–4.33 | m–vs |
| 30.3–30.5 | 2.950–2.931 | w–m |

All of the as-synthesized ZAPO-34 compositions for which X-ray powder diffraction data have been obtained at present have X-ray patterns within the generalized pattern of Table XX (a), below:

TABLE XX

| (a) | | |
|---|---|---|
| 2θ | d, (A) | Relative Intensity |
| 9.4–9.5 | 9.41–9.31 | vs |
| 12.6–12.9 | 7.03–6.86 | vw–m |
| 14.0–14.2 | 6.33–6.24 | vw–w |
| 15.9–16.0 | 5.57–5.34 | w–m |

TABLE XX-continued

| (a) | | |
|---|---|---|
| 2θ | d, (A) | Relative Intensity |
| 17.8–18.2 | 4.98–4.87 | vw–m |
| 20.3–20.5 | 4.37–4.33 | m–vs |
| 22.2 | 4.00 | vw |
| 22.9–23.0 | 3.88–3.87 | vw |
| 25.0–25.4 | 3.56–3.51 | w–m |
| 25.7–25.8 | 3.47–3.45 | vw–w |
| 27.4–27.5 | 3.25–3.24 | vw |
| 28.2–28.6 | 3.16–3.12 | vw |
| 29.4–29.5 | 3.038–3.028 | vw |
| 30.3–30.5 | 2.950–2.931 | w–s |
| 31.1–31.4 | 2.876–2.849 | w–m |
| 34.1–34.3 | 2.629–2.614 | vw–w |
| 36.1–36.2 | 2.488–2.481 | vw |
| 39.5 | 2.281 | vw |
| 42.8–43.1 | 2.113–2.099 | vw |
| 47.4 | 1.918 | vw |
| 48.8–48.9 | 1.866–1.863 | vw |
| 50.6–50.8 | 1.804–1.797 | vw |

EXAMPLE 62

(Preparation of ZAPO-35)

The MeAPO species denominated ZAPO-35 was prepared by the following procedure: A solution of 22 grams of zinc (II) acetate dihydrate in 139.2 grams of water was added to 53.1 grams of aluminum isopropoxide in a high shear blender and blended until a thick gel formed. To this gel was added a solution of 46.2 grams of 85% orthophosphoric acid, 46.2 grams of water and 22.2 grams of quinuclidine ($C_7H_{13}N$). This mixture was then blended at high speed until homogeneous. The composition of the final reaction mixture in molar oxide ratios were:

$1.0C_7H_{13}N:0.5ZnO:0.65Al_2O_3:P_2O_5:1.0CH_3COOH:3.9C_3H_7OH:55H_2O$.

The reaction mixture was heated at 150° C. for 72 hours in a sealed reactor. The solids were recovered by centrifugation, washed with water and dried in air at room temperature. The product had an X-ray powder diffraction pattern characterized by the following data:

TABLE FF

| 2θ | d, (A) | 100 × I/I$_o$ | |
|---|---|---|---|
| 8.5 | 10.40 | 14 | |
| 10.8 | 8.19 | 42 | |
| 13.3 | 6.66 | 35 | |
| 15.9 | 5.57 | 8 | |
| 17.2 | 5.16 | 68 | |
| 17.7 | 5.01 | 10 | (shoulder) |
| 21.2 | 4.19 | 49 | |
| 21.8 | 4.08 | 100 | |
| 25.0 | 3.56 | 6 | |
| 26.6 | 3.35 | 23 | |
| 28.6 | 3.12 | 34 | |
| 31.8 | 2.814 | 48 | |
| 34.6 | 2.592 | 12 | |
| 35.5 | 2.529 | 7 | |
| 42.0 | 2.151 | 7 | |
| 48.5 | 1.877 | 9 | |
| 49.2 | 1.852 | 7 | |
| 51.3 | 1.781 | 7 | |
| 55.1 | 1.667 | 7 | |

A portion of the product solids was subjected to chemical analysis. The product was found to contain 13.1 wt. % ZnO, 22.1 wt. % $Al_2O_3$, 44.7 wt. % $P_2O_5$, 20.2 wt. % LOI, 11.2 wt. % C, and 1.7 wt. % N, giving a product composition in terms of molar oxide ratios of:

$0.42C_7H_{13}N:0.51ZnO:0.69Al_2O_3:P_2O_5:1.0H_2O$ or in terms of $TO_2$ units, an essential empirical formula (anhydrous basis) of:

$0.11C_7H_{13}N:(Zn_{0.13}Al_{0.35}P_{0.51})O_2$.

The species ZAPO-35 as referred to herein is a zinc aluminophosphate material having a three-dimensional microporous crystal framework structure of $PO_2^+$, $AlO_2^-$ and $ZnO_2^{-2}$ tetrahedral units, and whose essential empirical chemical composition on an anhydrous basis is:

$mR:(Zn_xAl_yP_z)O_2$ wherein "R" represents at least one organic templating agent present in the intracrystalline pore system: "m" represents the moles of "R" present per mole of $(Zn_xAl_yP_z)O_2$ and has a value of from zero to 0.3, "x", "y" and "z" represent respectively, the mole fraction of zinc, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said zinc aluminophosphate having a characteristic X-ray powder diffraction pattern which contains at least the d-spacings set forth below in Table XXI. In the form as synthesized in accordance with the process of this invention, "m" has a value of from 0.02 to 0.3.

TABLE XXI

| 2θ | d, (A) | Relative Intensity |
|---|---|---|
| 10.8 | 8.19 | m |
| 13.3 | 6.66 | m |
| 17.2 | 5.16 | s |
| 21.2 | 4.19 | m |
| 21.8 | 4.08 | vs |
| 31.8 | 2.814 | m |

EXAMPLE 63

(Preparation of ZAPO-36)

(a) The zinc aluminophosphate structural species of the present invention denominated ZAPO-36 was synthesized by the following procedure:

A first mixture was prepared by combining 46.2 grams of 85% orthophosphoric acid and 93.5 grams of water, to which was added 25.2 grams of a hydrated aluminum oxide (I). A solution prepared by dissolving 7.35 grams of zinc acetate dihydrate $(Zn(CH_3CO_2)_2.2H_2O)$ in 25.1 grams of $H_2O$ was added to this first mixture and to the resulting mixture 28.7 grams of tripropylamine $(C_9H_{21}N)$ was added to form the final reaction mixture which has a composition in terms of molar oxide ratios of:

$1.0C_9H_{21}N:0.167ZnO:0.917Al_2O_3:P_2O_5:39.8H_2O:0.33CH_3COO$.

The reaction mixture was sealed in a stainless steel pressure vessel and heated at 150° C. for 24 hours. The solid product was recovered by filtration, washed with water, and dried in air at room temperature. A portion of the solid that passed through a 120 mesh screen was subjected to X-ray and chemical analysis. This solid has an X-ray diffraction pattern characterized by the following data:

TABLE GG

| 2θ | d, (A) | 100 × I/I$_o$ |
|---|---|---|
| 7.8 | 11.3 | 100 |
| 8.1 | 10.9 | Shoulder |
| 13.5 | 6.56 | 4 |
| 15.8 | 5.61 | Shoulder |
| 16.4 | 5.40 | 32 |
| 19.0 | 4.67 | 49 |
| 20.7 | 4.29 | 36 |
| 21.6 | 4.11 | Shoulder |
| 21.9 | 4.06 | 44 |
| 22.3 | 3.99 | 40 |
| 22.8 | 3.90 | Shoulder |
| 23.7 | 3.75 | 11 |
| 27.1 | 3.29 | 16 |
| 28.2 | 3.16 | 13 |
| 28.9 | 3.09 | 11 |
| 30.2 | 2.96 | 7 |
| 31.8 | 2.814 | 10 |
| 34.7 | 2.585 | 20 |
| 35.5 | 2.529 | 4 |

Chemical analysis showed 31.1 wt. % $Al_2O_3$, 45.2 wt.% $P_2O_5$, 5.2 wt.% ZnO, 7.9 wt.% C, 0.9 wt.% N, and 17.5 wt.% LOI, giving a product composition in molar oxide ratios of:

$0.23C_9H_{21}N:0.20ZnO:0.96Al_2O_3:P_2O_5:1.2H_2O$, or alternatively $0.06C_9H_{21}N:(Zn_{0.05}Al_{0.47}P_{0.49})O_2:0.29H_2O$.

(b) A portion of the solid product that did not pass through a 120 mesh screen in part (a) exhibited an X-ray diffraction powder pattern identical to that shown above.

(c) A portion of the solid of part (b) was heated in a vacuum oven at 150° C. for 19 hours to remove any adsorbed water. This activated sample was then stored in moist air at a constant relative humidity of 79% until there was essentially no further weight gain. This hydrated sample exhibited a weight gain of 7.5% based on the activated weight. X-ray analysis of the hydrated sample showed essentially no change in the X-ray powder pattern after being subjected to this procedure.

The species ZAPO-36 as referred to herein is a zinc aluminophosphate material having a three dimensional microporous crystal framework structure of $PO_2^+$, $AlO_2^-$ and $ZnO_2^{-2}$ tetrahedral units, and whose essential empirical chemical composition on an anhydrous basis is:

$mR:(Zn_xAl_yP_z)O_2$ wherein "R" represents at least one organic templating agent present in the intracrystalline pore system; "m" represents the moles of "R" present per mole of $(Zn_xAl_yP_z)O_2$ and has a value of from zero to 0.3, "x", "y" and "z" represent respectively, the mole fraction of zinc, aluminum and phosphorus present in the oxide moiety, said mole fraction being within the compositional area bounded by points A, B, C and D on the ternary diagram which is FIG. 1, or preferably within the area bounded by points a, b, c and d on the ternary diagram which is FIG. 2, said zinc aluminophosphate having a characteristic X-ray powder diffraction pattern which contains at least the d-spacings set forth below in Table XXII. In the form as synthesized in accordance with the process of this invention, "m" has a value of from 0.02 to 0.3.

TABLE XXII

| 2θ | d, (A) | Relative Intensity |
|---|---|---|
| 7.9 | 11.3 | vs |

TABLE XXII-continued

| 2θ | d, (A) | Relative Intensity |
|---|---|---|
| 16.4 | 5.40 | m |
| 19.0 | 4.67 | m |
| 20.7 | 4.29 | m |
| 21.9 | 4.06 | m |
| 22.3 | 3.99 | m |

EXAMPLE 64

(Preparation of ZAPO-44)

(a) The MeAPO species denominated ZAPO-44 was prepared by combining a solution of 46.1 grams of 85% orthophosphoric acid in 92.4 grams of water with 21.7 grams of a hydrated aluminum oxide (I). A solution of 17.6 grams of zinc (II) acetate dihydrate in 63.0 grams of water was then added, followed by 19.8 grams of cyclohexylamine ($C_6H_{13}N$) to form the final reaction mixture which had a composition in terms of molar oxide ratios of:

1.0$C_6H_{13}N$:0.4ZnO:0.8$Al_2O_3$:$P_2O_5$:0.8$CH_3COOH$:50$H_2O$.

The reaction mixture was heated in a sealed reactor at 200° C. for 24 hours. The solids were recovered by passing an aqueous slurry of the product through a 200 mesh screen. Those solids not passing through the screen after repeated water washing were recovered by filtration and dried in air at room temperature. This solid was found to be pure ZAPO-44, and exhibited an X-ray powder diffraction pattern characterization by the following data:

TABLE HH

| 2θ | d, (A) | 100 × I/I$_o$ |
|---|---|---|
| 9.4 | 9.41 | 97 |
| 13.0 | 6.81 | 28 |
| 13.7 | 6.46 | 5 |
| 16.1 | 5.51 | 46 |
| 17.3 | 5.13 | 3 |
| 18.9 | 4.70 | 6 |
| 20.6 | 4.31 | 90 |
| 21.7 | 4.10 | 48 |
| 22.6 | 3.93 | 13 |
| 23.0 | 3.87 | 15 |
| 24.3 | 3.66 | 100 |
| 26.1 | 3.41 | 33 |
| 27.8 | 3.21 | 14 |
| 29.6 | 3.018 | 10 |
| 30.0 | 2.979 | 27 |
| 30.9 | 2.894 | 60 |
| 32.5 | 2.755 | 8 |
| 32.9 | 2.722 | 10 |
| 34.8 | 2.578 | 6 |
| 35.5 | 2.529 | 23 |
| 38.4 | 2.344 | 8 |
| 42.4 | 2.132 | 8 |
| 48.0 | 1.895 | 10 |
| 48.6 | 1.873 | 6 |
| 50.2 | 1.817 | 13 |
| 51.8 | 1.765 | 5 |
| 53.7 | 1.707 | 10 |

By chemical analysis, the product was found to contain 18.6 wt% $Al_2O_3$, 40.8 wt % $P_2O_5$, 12.2 wt. % C, 2.6 wt. % N, 17.4 wt. % ZnO and 23.7 wt. % LOI giving an overall product composition in molar oxide rations of:

0.59$C_6H_{13}N$:0.74ZnO:0.63$Al_2O_3$:$P_2O_5$:1.33$H_2O$ and a formula (anhydrous basis) of:

0.17$C_6H_{13}N$:($Zn_{0.19}Al_{0.32}P_{0.50}$)$O_2$.

(b) EDAX microprobe analysis in conjunction with SEM study on clean crystals of the product of part (a) having a crystal morphology characteristic of ZAPO-44 gives the following analysis based on relative peak heights:

| | Average of Spot Probes |
|---|---|
| Zn | 0.08 |
| Al | 0.31 |
| P | 0.61 |

The species ZAPO-44 as referred to herein is a zinc aluminophosphate material having a three-dimensional microporous crystal framework structure of $PO_2^+$, $AlO_2^-$ and $ZnO_2^{-2}$ tetrahedral units, and whose essential empirical chemical composition on an anhydrous basis is:

$$mR:(Zn_xAl_yP_z)O_2$$

wherein "R" represents at least one organic templating agent present in the intracrystalline pore system; "m" represents the moles of "m" present per mole of $(Zn_xAl_yP_z)O_2$ and has a value of from zero to 0.3, "x", "y" and "z" represent respectivly, the mole fractions of zinc, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said zinc aluminophosphate having a characteristic X-ray powder diffraction pattern which contains at least the d-spacings set forth below in TABLE XXIII. In the form as synthesized in accordance with the process of this invention, "m" has a value of from 0.02 to 0.3.

TABLE XXIII

| 2θ | d, (A) | Relative Intensity |
|---|---|---|
| 9.4 | 9.41 | vs |
| 16.1 | 5.51 | m |
| 20.6 | 4.31 | s |
| 24.3 | 3.66 | vs |
| 26.1 | 3.41 | m |
| 30.9 | 2.894 | s |

EXAMPLE 65

(Preparation of ZAPO-47)

(a) the MeAPO species denominated ZAPO-47 was prepared by the following procedure: A solution of 7.3 grams of zinc (II) acetate dihydrate in 89.5 grams of water was added to 74.9 grams of aluminum isopropxide in a high shear blender and blended until a thick gel formed. To this gel was added a solution of 46.2 grams of 85% orthophoshoric acid, 46.2 grams of water and 46.9 grams of diethylethanolamine ($C_6H_{15}NO$). This mixture was then blended at high speed until homogenous. The composition of the final reaction mixture in molar oxide ratios was:

2.0$C_6H_{15}NO$:0.167ZnO:0.917$Al_2O_3$:0.33$CH_3COOH$:5.5i-$C_3H_7OH$:40$H_2O$.

The reaction mixture was heated at 150° C. for 144 hours in a sealed reactor. A solid product was separated from unreacted gel by repeatedly slurrying the solids in fresh water and allowing the denser crystalline fraction to settle out. This fraction was then dried in air at room temperature. By X-ray analysis, the solid product was found to be pure ZAPO-47 and had an X-ray powder diffraction pattern characterized by the following data:

TABLE JJ

| 2θ | d, (A) | 100 × I/I$_o$ |
|---|---|---|
| 9.4 | 9.41 | 100 |
| 12.9 | 6.86 | 15 |
| 13.8 | 6.42 | 6 |
| 15.9 | 5.57 | 34 |
| 17.4 | 5.10 | 8 |
| 18.9 | 4.70 | 4 |
| 20.5 | 4.33 | 85 |
| 21.7 | 4.10 | 8 |
| 22.9 | 3.88 | 10 |
| 24.5 | 3.63 | 22 |
| 25.8 | 3.45 | 21 |
| 27.5 | 3.24 | 12 |
| 29.4 | 3.038 | 7 |
| 30.2 | 2.959 | 14 |
| 30.5 | 2.931 | 49 |
| 41.4 | 2.849 | 5 |
| 33.2 | 2.698 | 2 |
| 34.5 | 2.600 | 9 |
| 35.4 | 2.536 | 5 |
| 38.2 | 2.356 | 4 |
| 39.5 | 2.281 | 4 |
| 42.3 | 2.137 | 2 |
| 47.6 | 1.910 | 4 |
| 48.5 | 1.877 | 6 |
| 50.0 | 1.824 | 6 |
| 53.1 | 1.725 | 6 |
| 53.8 | 1.704 | 2 |

Chemical analysis showed that the solid contained 22.6 wt % $Al_2O_3$, 40.2 wt % $P_2O_5$, 10.2 wt % C, 2.1 wt % N, 12.8 wt % ZnO and 24.8 wt % LOI giving an overall product composition in molar oxide ratios of:

0.50$C_6H_{15}NO$:0.56ZnO:0.78$Al_2O_3$:$P_2O_5$:2.08$H_2O$ and a formula (anhydrous basis) of:

0.12$C_6H_{15}NO$:($Zn_{0.13}Al_{0.38}P_{0.49}$)$O_2$.

(b) EDAX microprobe analysis performed in conjunction with scanning electron microscope study on clean crystals having a crystal morphology characteristic of ZAPO-47 gives the following analysis based on relative peak heights:

| | Average of Spot Probes |
|---|---|
| Zn | 0.03 |
| Al | 0.38 |
| P | 0.59 |

The species ZAPO-47 as referred to herein is a zinc aluminophosphate material having a three-dimensional microporous crystal framework structure of $PO_2^+$, $AlO_2^-$ and $ZnO_2^{-2}$ tetrahedral units, and whose essential empirical chemical composition on an anhydrous basis is:

mR:($Zn_xAl_yP_z$)$O_2$ wherein "R" represents at least one organic templating agent present in the intracrystalline pore system; "m" represents the moles of "R" present per mole of ($Zn_xAl_yP_z$)$O_2$ and has a value of from zero to 0.3, "x", "y" and "z" represent respectively, the mole fractions of zinc, aluminum and phosphorus present in the oxide moiety, said mole fractions being within the compositional area bounded by points A, B, C and D on the ternary from zero to 0.3, "x", "y" and "z" represent respectivly, the mole fractions of zinc, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said zinc aluminophosphate having a characteristic X-ray powder diffraction pattern which contains at least the d-spacings set forth below in TABLE XXIV. In the form as synthesized in accordance with the process of this invention, "m" has a value of from 0.02 to 0.3.

TABLE XXIV

| 2θ | d, (A) | Relative Intensity |
|---|---|---|
| 9.4 | 9.41 | vs |
| 15.9 | 5.57 | m |
| 20.5 | 4.33 | s |
| 24.5 | 3.63 | w |
| 25.8 | 3.45 | w |
| 30.5 | 2.931 | m |

EXAMPLE 66

(Preparation of MnAPO-5)

In the preparation of the manganese aluminophosphate species denominated MnAPO-5, a solution of 8.2 grams of manganese (II) acetate tetrahydrate [Mn(CH$_3$CO$_2$)$_2$.4H$_2$O] in 107.4 grams of water was added to 46.9 grams of aluminum isopropoxide in a high-shear blender and processed until a thick gel formed. To this gel was added a solution composed of 46.2 grams of 85% orthophosphoric acid, 46.3 grams of water and 46.9 grams of diethylethanolamine (C$_6$H$_{15}$NO) to form the final homogeneous reaction mixture which has a composition in terms of molar oxide ratios of 2.0C$_6$H$_{15}$NO:0.167MnO:0.917Al$_2$O$_3$:P$_2$O$_5$:0.33CH$_3$COOH:5.5C$_3$H$_7$OH:45H$_2$O.

The reaction mixture was heated for 24 hours in a sealed reactor at 200° C. The solids were recovered by filtration, washed with water, and dried in air at room temperature. A portion of the solids was subjected to X-ray analysis. The solid was pure MnAPO-5 and had an X-ray diffraction powder pattern characterized by the following data:

TABLE KK

| 2θ | d, (A) | 100 × I/I$_o$ |
|---|---|---|
| 7.3 | 12.11 | 100 |
| 12.9 | 6.86 | 11 |
| 14.8 | 5.99 | 33 |
| 19.6 | 4.53 | 47 |
| 20.9 | 4.25 | 32 |
| 22.3 | 3.99 | 57 |
| 24.6 | 3.62 | 5 |
| 25.8 | 3.45 | 27 |
| 28.9 | 3.09 | 11 |
| 29.9 | 2.99 | 19 |
| 33.4 | 2.683 | 4 |
| 34.3 | 2.614 | 15 |
| 36.8 | 2.442 | 3 |
| 37.5 | 2.398 | 7 |
| 42.0 | 2.151 | 3 |
| 47.4 | 1.918 | 4 |

EXAMPLES 67

(Preparation of MnAPO-5)

In another preparation of MnAPO-5, 46.2 grams of an 85% aqueous orthophosphoric acid solution, 43.7 grams of water and 21.7 grams of hydrated aluminum oxide (I) were first combined, and to the resulting composition was then added a solution prepared by dissolving 13.5 grams of manganese (II) sulfate monohydrate (MnSO$_4$.H$_2$O) in 30.2 grams of water. The final reaction mixture was formed by adding 73.6 grams of aqueous 40 wt % tetraethylammonium hydroxide (TEAOH). The composition of the final reaction mixture in terms of molar oxide ratios was TEAOH:0.4MnO:0.8Al$_2$O$_3$:P$_2$O$_5$:0.4H$_2$SO$_4$:40H$_2$O.

The reaction mixture was heated at 200° C. for 24 hours in a sealed reactor. The solids were recovered by filtration, washed with water and dried in air at room temperature. A portion of the solids that passed through a 60 mesh screen was subjected to X-ray analysis. The solid was found to be impure but the major phase was MnAPO-5 and an X-ray powder diffraction pattern essentially identical to that in Example 66.

EXAMPLE 68

(Preparation of MnAPO-5)

(a) A MnAPO-5 product similar in purity to that of Example 67, the major phase of which had an X-ray powder diffraction pattern essentially the same as in Example 66 was prepared by the following procedure: 135.1 grams of water was added to 65.4 grams of aluminum isopropoxide [Al(i-C$_3$H$_7$O)$_3$] in a blender. The resulting mixture was blended at high speed until a thick gel formed. To this gel was added stepwise 46.2 grams of 85% orthophosphoric acid using a slow blender speed. A solution prepared by dissolving 19.6 grams of manganese (II) acetate tetrahydrate [Mn(CH$_3$CO$_2$)$_2$.4H$_2$O] in 35.2 grams of water was added to the gel and the resulting mixture was blended at high speed. The final reaction mixture was formed by adding 73.6 grams of aqueous 40 wt % tetraethylammonium hydroxide (TEAOH). The composition of the final reaction mixture in terms of molar oxide ratios was:

TEAOH:0.4MnO:0.8Al$_2$O$_3$:P$_2$O$_5$:0.8CH$_3$COOH:4-.8$_i$-C$_3$H$_7$OH:66H$_2$O.

The reaction mixture was heated at 200° C. for 24 hours in a sealed reactor. The solids were recovered by filtration, washed with water, and dried in air at room temperature. A portion of the solids that passed through a 60 mesh screen was subjected to X-ray analysis. The solid was found to be impure MnAPO-5 in which the major phase had an X-ray powder diffraction pattern essentially identical to that in Example 66.

(b) EDAX microprobe analysis performed in conjunction with a scanning electron microscope study on a sample of clean crystals of part (a) above having a crystal morphology characteristic of MnAPO-5 gives the following analysis based on relative peak heights.

| | Spot Probe |
|---|---|
| Mn | 0.02 |
| Al | 0.42 |
| P | 0.55 |

EXAMPLE 69

(Preparation of MnAPO-5)

(a) Using the same reagents and mixing procedures as in Example 67 above (except that manganese acetate tetrahydrate was substituted for manganese sulfate monohydrate), a reaction mixture was prepared having the following composition in terms of molar oxide ratios:

TEAOH:0.667MnO:0.667Al$_2$O$_3$:P$_2$O$_5$:1.33CH$_3$COOH:49H$_2$O.

The mixture was crystallized under autogeneous pressure at 150° C. for 72 hours. The major phase of the solid product was identified by X-ray analysis as MnAPO-5.

(b) EDAX microprobe analysis on clean crystals of part (a) having a crystal morphology characteristic of MnAPO-5 gave the following analysis based on relative peak heights:

| | Spot Probe |
|---|---|
| Mn | 0.02 |
| Al | 0.44 |
| P | 0.54 |

EXAMPLE 70

(Preparation of MnAPO-5)

(a) The species MnAPO-5 was found to be templated by tripropylamine in a preparation using the following procedure: A reaction mixture was formed by combining 46.2 grams of 85% orthophosphoric acid and 92.6 grams of water and adding 25.0 grams of a hydrated aluminum oxide (I). A solution prepared by dissolving 8.2 grams manganese (II) acetate tetrahydrate in 25.3 grams of H$_2$O was added to the first mixture and to the resulting mixture 43.0 grams of tripropylamine (C$_9$H$_{21}$N) was added. The composition of the final reaction mixture in terms of molar oxide ratios was:

1.5C$_9$H$_{21}$N:0.167MnO:0.917Al$_2$O$_3$:P$_2$O$_5$:0.33CH$_3$COOH:40H$_2$O.

The reaction mixture was heated at 150° C. for 72 hours in a sealed reactor. The solids were recovered by filtration, washed with water, and dried in air at room temperature. A portion of the solids that passed through a 60 mesh screen was subjected to X-ray analysis. The solid was pure MnAPO-5 and had an X-ray diffraction powder pattern essentially identical to that in Example 66. Chemical analysis showed that the solid contained 33.8 wt % Al$_2$O$_3$, 48.2 wt % P$_2$O$_5$, 13.6 wt % LOI, 7.0 wt % C, 0.9 wt % N, and 3.1 wt % Mn, giving an overall product composition in molar oxide ratios of:

0.19C$_9$H$_{21}$N:0.17MnO:0.98Al$_2$O$_3$:1.0P$_2$O$_5$:0.72H$_2$O and an essential empirical formula (anhydrous basis) of:

0.05C$_9$H$_{21}$N:(Mn$_{0.04}$Al$_{0.47}$P$_{0.49}$)O$_2$.

(b) The preparation of MnAPO-5 of part (a) was repeated, and the product analyzed using X-rays. The product was found to be impure, but the major phase had an X-ray powder diffraction pattern essentially identical to that of Example 66.

(c) A portion of the solid of part (b) was calcined in air by heating from 100° to 500° C. at 100°/hr, then holding it at 500° C. for 4 hours. This calcined solid exhibited an X-ray powder diffraction pattern essentially identical to that in Example 66.

(d) Adsorption capacities were measured on this calcined product using a standard McBain-Bakr gravimetric adsorption apparatus. The following data were obtained on a sample activated at 370° C.

| Adsorbate | Kinetic Diameter, A | Pressure Torr | Temp.,°C. | Wt. % Adsorbed |
|---|---|---|---|---|
| O$_2$ | 3.46 | 12 | −183 | 14.1 |
| O$_2$ | 3.46 | 710 | −183 | 19.6 |
| Neopentane | 6.2 | 12 | 24 | 6.5 |

| Adsorbate | Kinetic Diameter, A | Pressure Torr | Temp.,°C. | Wt. % Adsorbed |
|---|---|---|---|---|
| Neopentane | 6.2 | 710 | 24 | 7.9 |
| $H_2O$ | 2.65 | 4.6 | 23 | 13.3 |
| $H_2O$ | 2.65 | 20.6 | 23 | 26.5 |

The pore size of the calcined product is greater than 6.2 A as shown in the adsorption of neopentane.

EXAMPLE 71

(Preparation of MnAPO-5)

Diisopropylamine was also found to template the formation of MnAPO-5 in a preparation using the following procedure: To a solution of 8.2 grams of manganese (II) acetate tetrahydrate in 124.1 grams of water was added 74.9 grams of aluminum isopropxide and the mixture blended to form a thick gel. To this gel was added a solution composed of 46.2 grams of 85% orthophosphoric acid, 46.2 grams of water and 20.1 grams of diisopropylamine ($C_6H_{15}N$) to form the final reaction mixture, which had a chemical composition expressed in terms of molar oxide ratios of:

$C_6H_{15}N$:0.167MnO:0.917$Al_2O_3$:$P_2O_5$:0.33$CH_3COOH$:5.5i-$C_3H_7OH$:50$H_2O$.

Crystallization of the reaction mixture was carried out in a sealed reactor at 200° C. for 168 hours. The resulting product was found by X-ray analysis to be impure, but the minor phase of the solids exhibited an X-ray powder diffraction pattern essentially identical to that of Example 66, above.

The species MnAPO-5 as referred to herein is a manganese aluminophosphate material having a three-dimensional microporous crystal framework structure of $PO_2^+$, $AlO_2^-$ and $MnO_2^{-2}$ tetrahedral units, and whose essential empirical chemical composition on an anhydrous basis is:

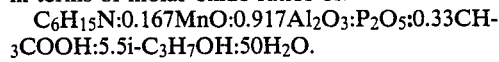

wherein "R" represents at least one organic templating agent present in the intracrystalline pore system: "m" represents the moles of "R" present per mole of $(Mn_xAl_yP_z)O_2$ and has a value of from zero to 0.3, "x", "y" and "z" represent respectively, the mole fractions of manganese, aluminum and phosphorus present in the oxide moiety, said mole fractions being within the compositional area bounded by points A, B, C and D on the ternary diagram which is FIG. 1, preferably within the area bounded by points a, b, c and d on the ternary diagram which is FIG. 2, said manganese aluminophosphate having a characteristic X-ray powder diffraction pattern which contains at least the d-spacings set forth below in TABLE XXV. In the form as synthesized in accordance with the process of this invention, "m" has a value of from 0.02 to 0.3.

TABLE XXV

| 2θ | d, (A) | Relative Intensity |
|---|---|---|
| 7.3–7.4 | 12.11–11.95 | vs |
| 14.8–15.0 | 5.99–5.91 | w–vs |
| 19.6–19.7 | 4.53–4.51 | w–vs |
| 20.9–21.2 | 4.25–4.19 | vw–s |
| 22.2–22.4 | 4.00–3.97 | w–s |
| 29.8–30.1 | 2.998–2.969 | w–vs |

All of the as-synthesized MnAPO-5 compositions for which X-ray powder diffraction data have presently been obtained have patterns which are within the generalized pattern of TABLE XXVI below:

TABLE XXVI

| 2θ | d, (A) | Relative Intensity |
|---|---|---|
| 7.3–7.4 | 12.11–11.95 | vs |
| 12.8–12.9 | 6.92–6.86 | vw–w |
| 14.8–15.0 | 5.99–5.91 | w–vs |
| 19.6–19.7 | 4.53–4.51 | w–vs |
| 20.9–21.2 | 4.25–4.19 | vw–s |
| 22.2–22.4 | 4.00–3.97 | w–s |
| 24.6–24.9 | 3.62–3.58 | vw |
| 25.7–26.0 | 3.47–3.43 | w–m |
| 28.9–29.1 | 3.09–3.07 | vw–m |
| 29.8–30.1 | 2.998–2.969 | w–vs |
| 33.4–33.7 | 2.683–2.660 | vw |
| 34.3–34.6 | 2.614–2.592 | w–m |
| 36.8–37.0 | 2.442–2.430 | vw |
| 37.5–37.9 | 2.398–2.374 | vw |
| 42.0–42.3 | 2.151–2.137 | vw |
| 47.4–47.5 | 1.918–1.914 | vw |

EXAMPLE 72

(Preparation of MnAPO-11)

In the preparation of the manganese aluminophosphate species denominated MnAPO-11, a solution of 14.7 grams of manganese (II) acetate tetrahydrate in 140.1 grams of water was added to 69.5 grams of aluminum isopropoxide in a high-shear blender and processed until a thick gel formed. To this gel was added a solution composed of 46.2 grams of 85% orthophosphoric acid, 46.2 grams of water, and 20.1 grams of diisopropylamine ($C_6H_{15}N$), and the resulting mixture then blended at high speed until homogeneous. The composition of the final reaction mixture in terms of molar oxide ratios was:

$C_6H_{15}N$:0.3MnO:0.85$Al_2O_3$:$P_2O_5$:0.6$CH_3COOH$:5.1$C_3H_7OH$:55$H_2O$.

The reaction mixture was heated at 200° C. for 168 hours in a sealed reactor. The solids were recovered by filtration, washed with water, and air dried at room temperature. A portion of the solids was subjected to X-ray analysis. The sample was found to be pure MnAPO-11 and had an X-ray diffraction powder pattered characterized by the following data:

TABLE LL

| 2θ | d, (A) | 100 × I/I$_o$ |
|---|---|---|
| 8.0 | 11.05 | 43 |
| 9.3 | 9.51 | 56 |
| 13.0 | 6.81 | 27 |
| 15.6 | 5.68 | 43 |
| 16.2 | 5.47 | 6 |
| 18.9 | 4.70 | 9 |
| 20.2 | 4.40 | 57 |
| 21.0 | 4.23 | 63 |
| 22.0 | 4.04 | 49 |
| 22.4 | 3.97 | 46 |
| 22.6 | 3.93 | 50 |
| 23.0 | 3.87 | 100 |
| 24.3 | 3.66 | 9 |
| 24.6 | 3.62 | 14 |
| 26.3 | 3.39 | 35 |
| 28.1 | 3.18 | 10 |
| 28.6 | 3.12 | 25 |
| 29.4 | 3.04 | 9 |
| 31.4 | 2.849 | 9 |
| 32.6 | 2.747 | 25 |
| 34.1 | 2.629 | 11 |
| 36.2 | 2.481 | 8 |
| 37.6 | 2.392 | 11 |
| 39.2 | 2.298 | 5 |
| 42.8 | 2.113 | 5 |
| 44.6 | 2.032 | 8 |

TABLE LL-continued

| 2θ | d, (A) | 100 × I/I₀ |
|---|---|---|
| 50.6 | 1.804 | 6 |
| 54.4 | 1.687 | 5 |

EXAMPLE 73

(Preparation of MnAPO-11)

The species MnAPO-11 was found to be templated by di-n-propylamine in a preparation carried out as follows: A first solution of 46.2 grams of 85% orthophosphoric acid in 92.5 grams of water was added to 21.7 grams of a hydrated aluminium oxide (I). A second solution prepared by dissolving 19.6 grams of manganese (II) acetate tetrahydrate in 60.1 grams of H₂O was added to this initial mixture, and to the resulting mixture 20.2 grams of di-n-propylamine ($C_6H_{15}N$) was added. The composition of the final reaction mixture in terms of molar oxide ratios was: $C_6H_{15}N:0.4MnO:0.8Al_2O_3:P_2O_5:0.8CH_3CO_2H:50H_2O$. The reaction mixture was crystallized for 24 hours at 150° C. in a sealed reactor, and the solid product recovered by filtration, washed with water and dried in air at room temperature. By X-ray analysis the solids were found to be impure MnAPO-11, but the mnor phase has an X-ray powder diffraction pattern essentially identical to that in Example 72.

EXAMPLE 74

(Preparation of MnAPO-11)

A reaction mixture was prepared by combining 46.3 grams of 85% orthophosphoric acid and 92.7 grams of water, to which was added 24.9 grams of a hydrated aluminum oxide (I). A solution prepared by dissolving 8.2 grams of manganese (II) acetate tetrahydrate in 25.3 grams of H₂O was added to the first mixture, and to the resulting mixture 20.3 grams of diisopropylamine ($C_6H_{15}N$) was added to form a final reaction mixture having a composition expressed in terms of molar oxide ratios of:

$C_6H_{15}N:0.167MnO:0.917Al_2O_3:P_2O_5:0.33CH_3COOH:40H_2O$.

The reaction mixture was heated in a sealed reactor for 72 hours at 200° C. The reaction product solids were recovered by filtration, washed with water, and air-dried at room temperature. A portion of the solids that did not pass through a 60 mesh screen was submitted for X-ray analysis. The solid was pure, and had an X-ray powder diffraction pattern essentially identical to that in Example 72. Chemical analysis showed that the solid contained 33.9 wt % $Al_2O_3$, 51.1 wt. % $P_2O_5$, 5.6 wt % C., 0.97 wt % N, 3.5 wt % Mn and 9.4 wt % LOI, giving an overall product composition in molar oxide ratios of:

$0.22C_6H_{15}N:0.18MnO:0.92Al_2O_3:P_2O_5 0.23H_2O$ and an essential empirical chemical composition on an anhydrous basis of:

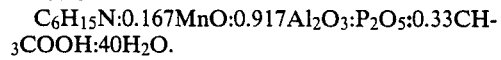
$0.05C_6H_{15}N:(Mn_{0.04}Al_{0.46}P_{0.50})O_2$.

EXAMPLE 75

(Preparation of MnAPO-11)

(a) MnAPO-11 was prepared with the same reactants as in Example 74, supra, but using a different order of combination to obtain the final reaction mixture. In this preparation 8.2 grams of manganese (ii) acetate tetrahydrate was dissolved in 117.6 grams of water, to which was first added 46.2 grams of an 85% orthophosphoric acid solution and then 24.9 grams of a hydrated aluminum oxide (I). To the resulting mixture was finally added 20.2 grams of diisopropylamine ($C_6H_{15}N$). The composition of the final reaction mixture in terms of molar oxide ratios was:

$C_6H_{15}N:0.167MnO:0.917Al_2O_3:P_2O_5:0.33CH_3COOH:40H_2O$.

Crystallization and recovery of the product were as described in Example 74. The product was found to be pure MnAPO-11 and to have an X-ray powder diffraction pattern and a chemical composition almost identical to that of Example 73, i.e., $0.21C_6H_{15}N:0.19MnO:0.93Al_2O_3:P_2O_5:0.3H_2O$ and an essential empirical chemical formula (anhydrous basis) of:

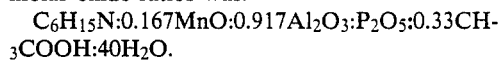
$0.05C_6H_{15}N:(Mn_{0.05}Al_{0.46}P_{0.49})O_2$.

EDAX mircoprobe analysis on isolated clean crystals of the product having a crystal morphology characteristic of MnAPO-11 gave the following analysis based on relative peak heights:

| | Average of area scans |
|---|---|
| Mn | 0.05 |
| Al | 0.48 |
| p | 0.47 |

The species MnAPO-11 as referred to herein is a manganese aluminophosphate material having a three-dimensional microporous crystal framework structure of $PO_2^+$, $AlO_2^-$ and $MnO_2^{-2}$ tetrahedral units, and whose essential empirical chemical composition on an anhydrous basis is:

$mR:(Mn_xAl_yP_z)O_2$ wherein "R" represents at least one organic templating agent present in the intracrystalline pore system; "m" represents the moles of "R" present per mole of $(Mn_xAl_yP_z)O_2$ and has a value of from zero to 0.3 and "x", "y" and "z" represent respectively, the mole fractions of manganese, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said manganese aluminophosphate having a characteristic X-ray powder diffraction pattern which contains at least the d-spacings set forth below in Table XXVII. In the form as synthesized in accordance with the process of this invention, "m" has a value of from 0.02 to 0.3.

TABLE XXVII

| 2θ | d, (A) | Relative Intensity |
|---|---|---|
| 9.3–9.6 | 9.51–9.21 | m–s |
| 20.2–20.3 | 4.40–4.37 | m–s |
| 21.0–21.1 | 4.23–4.21 | s–vs |
| 22.0–22.1 | 4.04–4.02 | m–s |
| 22.6–22.8 | 3.93–3.90 | s |
| 23.0–23.2 | 3.87–3.83 | s–vs |

All of the as-synthesized MnAPO-11 compositions for which X-ray powder diffraction data have presently been obtained have patterns which are within the generalized pattern of TABLE XXVIII below:

TABLE XXVIII

| 2θ | d, (A) | Relative Intensity |
|---|---|---|
| 8.0–8.1 | 11.05–10.92 | w-m |
| 9.3–9.6 | 9.51–9.21 | m-s |
| 13.0–13.2 | 6.81–6.71 | w |
| 15.6–15.7 | 5.68–5.64 | w-m |
| 16.2 | 5.47 | vw |
| 18.9–19.0 | 4.70–4.67 | vw |
| 20.2–20.3 | 4.40–4.37 | m-s |
| 21.0–21.1 | 4.23–4.21 | s-vs |
| 22.0–22.1 | 4.04–4.02 | m-s |
| 22.3–22.5 | 3.99–3.95 | m-s |
| 22.6–22.8 | 3.93–3.90 | s |
| 23.0–23.2 | 3.87–3.83 | s-vs |
| 24.3–24.4 | 3.66–3.65 | vw |
| 24.6–24.7 | 3.62–3.60 | w |
| 26.3–26.4 | 3.39–3.38 | m |
| 28.1 | 3.18 | vw |
| 28.6 | 3.12 | w |
| 29.3–29.4 | 3.048–3.038 | vw |
| 31.4–31.5 | 3.849–2.840 | vw-w |
| 32.6–32.7 | 2.747–2.739 | w |
| 34.1–34.2 | 2.629–2.622 | vw-w |
| 36.2 | 2.481 | vw |
| 37.4–37.7 | 2.404–2.386 | w |
| 39.1–39.2 | 2.304–2.298 | vw |
| 42.7–42.9 | 2.118–2.108 | vw |
| 44.5–44.6 | 2.036–2.032 | vw |
| 50.6 | 1.804 | vw |
| 54.4–54.5 | 1.687–1.684 | vw |

EXAMPLE 76

(Preparation of MnAPO-16)

The species of manganese aluminophosphate denominated MnAPO-16 was synthesized using quinuclidine as the templating agent in the following procedure: A first mixture was prepared by adding 21.7 grams of a hydrated aluminum oxide (I) to a solution of 46.2 grams of 85% orthophosphoric acid in 40.2 grams of water. To this mixture was added a solution of 19.6 grams of manganese (II) acetate tetrahydrate in 35.2 grams of water to form a second mixture. The final reaction mixture was formed by adding a solution of 22.3 grams of quinuclidine ($C_7H_{13}N$) in 41.0 grams of water to the second mixture. The composition of the final reaction mixture in terms of molar oxide ratios was:

$C_7H_{13}N:0.4MnO:0.8Al_2O_3:P_2O_5:0.8CH_3COOH:40H_2O$.

Crystallization was carried out by maintaining the reaction mixture in a sealed reactor for 24 hours at 150° C. The solids were recovered by filtration, washed with water, and dried in air at room temperature.

A portion of the solids that passed through a 325 mesh screen was subjected to X-ray analysis. The solid was pure MnAPO-16 and had an X-ray diffraction powder pattern characterized by the following data:

TABLE MM

| 2θ | d, (A) | 100 × I/I$_o$ |
|---|---|---|
| 11.3 | 7.83 | 100 |
| 18.7 | 4.75 | 28 |
| 21.9 | 4.06 | 88 |
| 23.0 | 3.87 | 23 |
| 26.6 | 3.35 | 26 |
| 29.0 | 3.08 | 7 |
| 29.8 | 2.998 | 15 |
| 32.6 | 2.747 | 3 |
| 34.7 | 2.585 | 5 |
| 37.9 | 2.374 | 7 |
| 39.7 | 2.270 | 2 |
| 44.3 | 2.045 | 2 |
| 48.5 | 1.877 | 6 |
| 52.4 | 1.746 | 2 |
| 54.7 | 1.678 | 2 |

TABLE MM-continued

EXAMPLE 77

(Preparation of MnAPO-16)

Using the same reagents and mixing procedure as in Example 76, above, MnAPO-16 was crystallized from a reaction mixture having the composition $C_7H_{13}N:0.167MnO:0.917Al_2O_3:P_2O_5:0.33CH_3COOH:40H_2O$ by heating at 150° C. for 168 hours in a sealed reactor. The product solids were recovered by centrifugation, washed with water and dried in air at room temperature. By X-ray analysis the product was found to be pure MnAPO-16 and had a powder diffraction pattern essentially identical to that of Example 76, above. By chemical analysis the product was found to contain 29.5 wt.% $Al_2O_3$, 44.5 wt.% $P_2O_5$, 11.0 wt.% C., 1.8 wt.% N, 4.5 wt.% MnO and 21.6 wt.% LOI, corresponding to a product composition in terms of molar oxide ratios of:

$0.42C_7H_{13}N:0.20MnO:0.92Al_2O_3:P_2O_5:1.25H_2O$.

The essential empirical formula of the composition was $0.10C_7H_{13}N:(Mn_{0.05}Al_{0.46}P_{0.49})O_2$.

EDAX microprobe analysis, performed in conjunction with a scanning electron microscope study, on clean crystals of the product having a crystal morphology characteristic of MnAPO-16 gave the following analysis based on relative peak heights:

| | Average of Spot Probes | Average of Area Scan |
|---|---|---|
| Mn | 0.03 | 0.05 |
| Al | 0.43 | 0.40 |
| P | 0.54 | 0.55 |

The species MnAPO-16 as referred to herein is a manganese aluminophosphate material having a three-dimensional microporous crystal framework structure of $PO_2^+$, $AlO_2^-$ and $MnO_2^{-2}$ tetrahedral units and whose essential empirical chemical composition on an anhydrous basis is: $mR:(Mn_xAl_yP_z)O_2$ wherein "R" represents at least one organic templating agent present in the intracrystalline pore system; "m" represents the moles of "R" present per mole of $(Mn_xAl_yP_z)O_2$ and has a value of from zero to 0.3, "x", "y" and "z" represent respectively, the mole fractions of manganese, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said manganese aluminophosphate having a characteristic X-ray powder diffraction pattern which contains at least the d-spacings set forth below in Table XXIV. In the form as synthesized in accordance with the process of this invention, "m" has a value of from 0.02 to 0.3.

TABLE XXIX

| 2θ | d, (A) | Relative Intensity |
|---|---|---|
| 11.3 | 7.83 | vs |
| 18.7–18.8 | 4.75–4.72 | w |

TABLE XXIX-continued

| 2θ | d, (A) | Relative Intensity |
|---|---|---|
| 21.9 | 4.06 | s |
| 23.0 | 3.87 | w |
| 26.6 | 3.35 | w |
| 29.8–29.9 | 3.00–2.99 | w |

All of the as-synthesized MnAPO-16 compositions for which X-ray powder diffraction data have presently been obtained have patterns which are within the generalized pattern of TABLE XXX below:

TABLE XXX

| 2θ | d, (A) | Relative Intensity |
|---|---|---|
| 11.3 | 7.83 | vs |
| 18.7–18.8 | 4.75–4.72 | w |
| 21.9 | 4.06 | s |
| 23.0 | 3.87 | w |
| 26.6 | 3.35 | w |
| 29.0–29.1 | 3.08–3.07 | vw |
| 29.8–29.9 | 2.998–2.988 | w |
| 32.6–32.8 | 2.747–2.730 | vw |
| 34.7–34.9 | 2.585–2.571 | vw |
| 37.9–38.0 | 2.374–2.368 | vw |
| 39.7–39.8 | 2.270–2.265 | vw |
| 44.3–44.4 | 2.045–2.040 | vw |
| 48.5–48.6 | 1.877–1.873 | vw |
| 52.4–52.5 | 1.746–1.743 | vw |
| 54.7–54.8 | 1.678–1.675 | vw |

EXAMPLE 78

(Preparation of MnAPO-34)

The manganese aluminophosphate denominated MnAPO-34 was synthesized using the following procedure: A reaction mixture was prepared by combining 24.9 grams of a hydrated aluminum oxide (I) with 46.2 grams of 85% orthophosphoric acid in 47.4 grams of water. A solution prepared by dissolving 8.2 grams of manganese (II) acetate tetrahydrate in 25.9 grams of water was then added and finally 73.6 grams of an aqueous 40% solution of tetraethylammonium hydroxide (TEAOH). The reaction mixture composition was:

TEAOH:0.167MnO:0.917Al$_2$O$_3$:P$_2$O$_5$:0.33CH$_3$COOH:40H$_2$O.

The reaction mixture was heated in a sealed reactor for 24 hours at 150° C. and the solids recovered by centrifugation, washed with water and dried in air at room temperature. A portion of the solids that passed through a 60 mesh screen was subjected to X-ray analysis. The solid was found to be pure MnAPO-34 and had an X-ray powder diffraction pattern characterized by the following data:

TABLE NN

| 2θ | d, (A) | 100 × I/I$_o$ |
|---|---|---|
| 9.5 | 9.31 | 100 |
| 12.9 | 6.86 | 18 |
| 14.1 | 6.28 | 18 |
| 16.1 | 5.51 | 49 |
| 18.1 | 4.90 | 26 |
| 20.6 | 4.31 | 89 |
| 22.3 | 3.99 | 5 |
| 23.1 | 3.85 | 5 |
| 25.3 | 3.52 | 26 |
| 25.8 | 3.45 | 22 |
| 27.6 | 3.23 | 5 |
| 28.4 | 3.14 | 5 |
| 29.5 | 3.028 | 8 |
| 30.5 | 2.931 | 32 |
| 31.3 | 2.858 | 27 |

TABLE NN-continued

| 2θ | d, (A) | 100 × I/I$_o$ |
|---|---|---|
| 34.4 | 2.607 | 8 |
| 36.4 | 2.468 | 5 |
| 47.4 | 1.918 | 5 |
| 47.6 | 1.910 | 3 |
| 49.1 | 1.855 | 6 |

Chemical analysis established that the product contained 28.7 wt.% Al$_2$O$_3$, 41.2 wt.% P$_2$O$_5$, 24.6 wt.% LOI, 8.7 wt.% C, 1.3 wt.% N, and 4.1 wt.% Mn, giving an overall product composition in molar oxide ratios of:

0.31TEAOH:0.26MnO:0.97Al$_2$O$_3$:P$_2$O$_5$:2.45H$_2$O and an essential empirical formula (anhydrous basis) of:

0.07TEAOH:(Mn$_{0.06}$Al$_{0.46}$P$_{0.48}$)O$_2$.

EXAMPLE 79

(Preparation of MnAPO-34)

A solution of 16.2 grams of manganese acetate tetrahydrate in 77.4 grams of water was combined with 68.1 grams of aluminum isopropoxide and subjected to high shear mixing until a thick gel formed. A solution prepared by combining 73.5 grams of 40 wt. % aqueous tetraethylammonium hydroxide (TEAOH), 46.2 grams of 85% orthophosphoric acid, and 46.3 grams of water was added to the gel and the resulting reaction mixture was subjected to high shear mixing until homogeneous. The composition of the final reaction mixture in terms of molar oxide ratios was:

1.0TEAOH:0.33MnO:0.83Al$_2$O$_3$:P$_2$O$_5$:0.67CH$_3$COOH:5.0i-C$_3$H$_7$OH:50H$_2$O.

The reaction mixture was heated in a sealed reactor at 100° C. for 168 hours. The solids were recovered by filtration, washed with water, and dried in air at room temperature. The solid was found to be crystallographically pure MnAPO-34 and had an X-ray powder diffraction pattern essentially identical to that in Table NN. Chemical analysis established that the product contained 27.1 wt.% Al$_2$O$_3$, 45.0 wt% P$_2$O$_5$, 7.9 wt.% MnO, 8.4 wt. % C, 1.2 wt.% N, and 19.9 wt. % LOI, giving an overall product composition in molar oxide ratios of:

0.27TEAOH:0.35MnO:0.84Al$_2$O$_3$:P$_2$O$_5$:1.5H$_2$O and an essential empirical formula (anhydrous basis) of:

0.07TEAOH:(Mn$_{0.09}$Al$_{0.42}$P$_{0.50}$)O$_2$.

EXAMPLE 80

(Preparation of MnAPO-34)

(a) A reaction mixture was prepared by combining 46.2 grams of 85% orthophosphoric acid and 43.8 grams of water, to which was added 21.7 grams of a hydrated aluminum oxide (I). A solution prepared by dissolving 13.5 grams of manganese (II) sulfate monohydrate in 30.2 grams of water was added to the first mixture, and to the resulting mixture, 73.6 grams of aqueous 40 wt.% tetraethylammonium hydroxide (TEAOH) was added. The composition of the final reaction mixture in molar oxide ratios was:

TEAOH:0.4MnO:0.8Al$_2$O$_3$:P$_2$O$_5$:0.4H$_2$SO$_4$:40H$_2$O.

The reaction mixture was heated in a sealed reactor for 120 hours at 150° C. The resulting solids were recovered by filtration, washed with water and dried in air at room temperature. A portion of the solids that passed through a 60 mesh screen was analyzed using X-rays. The solid was found to be impure and contained a minor amount of MnAPO-34.

(b) A reaction mixture having the same composition as in part (a) and prepared in the same manner as in part (a) except that manganese (II) acetate tetrahydrate was used as the source of manganese, was crystallized at 200° C. for 120 hours in a sealed reactor. Essentially the same results as in part (a) were obtained.

(c) Crystallizing the same reaction mixture as in part (b) at 100° C. for 120 hours did not materially alter the results obtained in part (b).

EXAMPLE 81

(Preparation of MnAPO-34)

Using the same reagents and procedure as in Example 80(b) a reaction mixture was prepared having the following composition in terms of molar oxide ratios:

TEAOH:0.667MnO:0.667Al$_2$O$_3$:P$_2$O$_5$:1.33CH$_3$COOH:50H$_2$O.

The reaction mixture was heated in a sealed reactor at 150° C. for 72 hours. The X-ray powder diffraction pattern of the recovered and washed solids indicated that the product was impure, but the major phase was MnAPO-34 having a powder pattern essentially the same as the product of Example 78.

EDAX microprobe analysis on clean crystals having a crystal morphology characteristic of MnAPO-34 gave the following results based on relative peak heights:

|    | Average of Spot Probes |
|----|------------------------|
| Mn | 0.08                   |
| Al | 0.36                   |
| P  | 0.56                   |

The species MnAPO-34 as referred to herein is a manganese aluminophosphate material having a three-dimensional microporous crystal framework structure of PO$_2^+$, AlO$_2^-$ and MnO$_2^{-2}$ tetrahedral units and whose essential empirical chemical composition on an anhydrous basis is: mR:(Mn$_x$Al$_y$P$_z$)O$_2$ wherein "R" represents at least one organic templating agent present in the intracrystalline pore system; "m" represents the moles of "R" present per mole of (Mn$_x$Al$_y$P$_z$)O$_2$ and has a value of from zero to 0.3, "x", "y" and "z" represent respectively, the mole fractions of manganese, aluminum and phosphorus present in the oxide moiety, said mole fractions being within the compositional area bounded by points A, B, C, and D on the ternary diagram which is FIG. 2, or preferably within the area bounded by points a, b, c and d on the ternary diagram which is FIG. 1, said manganese aluminophosphate having a characteristic X-ray powder diffraction pattern which contains at least the d-spacings set forth below in TABLE XXXI. In the form as synthesized in accordance with the process of this invention, "m" has a value of from 0.02 to 0.3.

TABLE XXXI

| 2θ | d, (A) | Relative Intensity |
|---|---|---|
| 9.4–9.6 | 9.41–9.21 | s–vs |
| 13.8–14.2 | 6.42–6.24 | vw–s |
| 15.9–16.0 | 5.57–5.54 | vw–m |
| 20.4–20.6 | 4.35–4.31 | m–vs |
| 25.1–25.3 | 3.55–3.52 | vw–m |
| 30.4–30.6 | 2.940–2.921 | w–m |

All of the as-synthesized MAPO-34 compositions for which X-ray powder diffraction patterns have been obtained at present, have X-ray patterns within the generalized pattern of Table XXXI (a), below:

TABLE XXXI (a)

| 2θ | d, (A) | Relative Intensity |
|---|---|---|
| 9.4–9.6 | 9.4–9.21 | s–vs |
| 12.8–12.9 | 6.92–6.86 | vw–w |
| 13.8–14.2 | 6.42–6.24 | vw–s |
| 15.9–16.0 | 5.57–5.54 | vw–m |
| 18.0–18.2 | 4.93–4.87 | vw–m |
| 20.4–20.6 | 4.35–4.31 | m–vs |
| 22.0–22.3 | 4.04–3.99 | vw |
| 23.0–23.2 | 3.87–3.83 | vw |
| 25.1–25.3 | 3.55–3.52 | vw–m |
| 25.3–25.8 | 3.52–3.45 | vw–m |
| 27.4–27.6 | 3.25–3.23 | vw–m |
| 28.3–28.5 | 3.15–3.13 | vw |
| 29.4–29.5 | 3.038–3.028 | vw |
| 30.4–30.6 | 2.940–2.921 | w–m |
| 31.1–31.4 | 2.876–2.849 | vw–w |
| 34.2–34.4 | 2.622–2.607 | vw |
| 36.2–36.4 | 2.481–2.468 | vw |
| 47.3–47.4 | 1.922–1.918 | vw |
| 47.6 | 1.910 | vw |
| 48.8–49.1 | 1.866–1.855 | vw |

EXAMPLE 82

(Preparation of MnAPO-35)

The manganese aluminophosphate denominated MnAPO-35 was synthesized using the following procedure: a solution of 24.5 grams of manganese (II) acetate tetrahydrate in 100.4 grams of water was added to 61.3 grams of aluminum isopropoxide in a high-shear blender and blended until a thick gel formed. To this gel was added a solution composed of 46.2 grams of 85% orthophosphoric acid, 65.1 grams of water, and 22.2 grams of quinuclidine (C$_7$H$_{13}$N). This mixture was then blended at high speed until homogenous. The composition of the final reaction mixture in molar oxide ratios was:

C$_7$H$_{13}$N:0.5MnO:0.75Al$_2$O$_3$:P$_2$O$_5$:CH$_3$COOH:45C$_3$H$_7$OH.

The reaction mixture was heated at 150° C. for 24 hours in a sealed reactor. The solids were recovered by filtration, washed with water, and dried in air at room temperature. A portion of the solids was subjected to X-ray analysis. The product was found to be pure MnAPO-35, and had an X-ray diffraction powder pattern characterized by the following data:

TABLE OO

| 2θ | d, (A) | 100 × I/I$_o$ |
|---|---|---|
| 8.6 | 10.28 | 15 |
| 11.0 | 8.04 | 47 |
| 13.3 | 6.66 | 29 |
| 15.8 | 5.61 | 7 |
| 17.3 | 5.13 | 73 |
| 17.8 | 4.98 | 13 |
| 21.0 | 4.23 | 53 |
| 21.8 | 4.08 | 100 |
| 23.1 | 3.85 | 20 |
| 23.6 | 3.77 | 6 |
| 25.0 | 3.56 | 6 |
| 26.7 | 3.34 | 23 |
| 28.5 | 3.13 | 26 |
| 28.7 | 3.11 | 24 |
| 29.0 | 3.08 | (shoulder) |
| 32.0 | 2.797 | 46 |
| 34.6 | 2.592 | 10 |
| 35.7 | 2.515 | 6 |
| 48.4 | 1.881 | 6 |
| 49.3 | 1.848 | 6 |
| 51.3 | 1.781 | 6 |

TABLE OO-continued

| 2θ | d, (A) | 100 × I/I$_o$ |
|---|---|---|
| 55.2 | 1.664 | 6 |

EXAMPLE 83

(Preparation of MnAPO-35)

A reaction mixture was prepared by combining 46.2 grams of 85% orthophosphoric acid and 40.2 grams of water, to which was added 21.7 grams of a hydrated aluminum oxide (I). A solution prepared by dissolving 19.6 grams of manganese (II) acetate tetrahydrate in 35.2 grams of water was added to the reaction mixture. To the resulting mixture a solution of 22.3 grams of quinuclidine ($C_7H_{13}N$) and 41.0 grams of water was added. The composition of the final reaction mixture in molar oxide ratios was $C_7H_{13}N$:0.4MnO:0.8Al$_2$O$_3$:P$_2$O$_5$:0.8CH$_3$CO$_2$H:40H$_2$O.

The reaction mixture was heated in a sealed reactor at 150° C. for 24 hours. The solids were recovered by filtration, washed with water, and dried in air at room temperature. A portion of the solids that passed through a 60 mesh screen but not through a 200 mesh screen was subjected to X-ray analysis. The product was impure, but the major phase had an X-ray diffraction powder pattern essentially identical to that in Example 82. Chemical analysis showed that the solid contained 25.3 wt. % Al$_2$O$_3$, 45.7 wt. % P$_2$O$_5$, 19.9 wt. % LOI, 12.0 wt. % C, 1.9 wt. % N and 9.4 wt. % MnO, giving an overall product composition in molar oxide ratios of:

0.44$C_7H_{13}N$:0.43MnO:0.77Al$_2$O$_3$:P$_2$O$_5$:0.69H$_2$O which corresponds to an essential empirical formula of 0.11$C_7H_{13}N$:(Mn$_{0.10}$Al$_{0.39}$P$_{0.51}$)O$_2$.

EDAX microprobe analysis on clean crystals having the characteristic morphology of MnAPO-35 gave the following results based on relative peak heights:

| | Average of Spot Probes |
|---|---|
| Mn | 0.12 |
| Al | 0.35 |
| P | 0.54 |

EXAMPLE 84

(Preparation of MnAPO-35)

Using the same reagents and procedure as in Example 83, a reaction mixture was prepared having the following composition in terms of molar oxide ratios:

$C_7H_{13}N$:0.5MnO:0.75Al$_2$O$_3$:P$_2$O$_5$:CH$_3$COOH:50H$_2$O.

The reaction mixture was heated at 150° C. for 24 hours in a sealed reactor. The solids were recovered by filtration, washed with water, and dried in air at room temperature. A portion of the solids that did not pass through a 200 mesh screen was submitted for X-ray analysis. The solid was impure, but the major phase had an X-ray powder diffraction pattern essentially identical to that in Example 82. Chemical analysis showed that the solid contained 23.8 wt. % Al$_2$O$_3$, 44.6 wt. % P$_2$O$_5$, 19.9 wt. % LOI, 11.6 wt. % C, 1.9 wt. % N and 11.6 wt. % MnO, giving an overall product composition in molar oxide ratios of:

0.44$C_7H_{13}N$:0.52MnO:0.74Al$_2$O$_3$:P$_2$O$_5$:0.81H$_2$O and an essential empirical formula (anhydrous basis) of:

0.11$C_7H_{13}N$:(Mn$_{0.13}$Al$_{0.37}$P$_{0.50}$)O$_2$.

The species MnAPO-35 as referred to herein is a manganese aluminophosphate material having a three-dimensional microporous crystal framework structure of PO$_2$+, AlO$_2$− and MnO$_2$−$^2$ tetrahedral units and whose essential empirical chemical composition on an anhydrous basis is: MR:(Mn$_x$Al$_y$P$_z$)O$_2$ wherein "R" represents at least one organic templating agent present in the intracrystalline pore system; "m" represents the moles of "R" present per mole of (Mn$_x$Al$_y$P$_z$)O$_2$ and has a value of from zero to 0.3, "x", "y" and "z" represent respectively, the mole fractions of manganese, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said manganese aluminophosphate having a characteristic X-ray powder diffraction pattern which contains at least the d-spacings set forth below in TABLE XXXII. In the form as synthesized in accordance with the process of this invention, "m" has a value of from 0.02 to 0.3.

TABLE XXXII

| 2θ | d, (A) | Relative Intensity |
|---|---|---|
| 10.9–11.0 | 8.12–8.04 | m |
| 17.2–17.3 | 5.16–5.13 | s |
| 21.0 | 4.23 | s |
| 21.8 | 4.08 | vs |
| 28.4–28.5 | 3.14–3.13 | w–m |
| 32.0–32.1 | 2.797–2.788 | m |

All of the as-synthesized MnAPO-35 compositions for which X-ray powder diffraction patterns have presently been obtained, have X-ray patterns within the generalized pattern of Table XXXII (a), below:

TABLE XXXII (a)

| 2θ | d, (A) | Relative Intensity |
|---|---|---|
| 8.6 | 10.28 | w |
| 10.9–11.0 | 8.12–8.04 | m |
| 13.3 | 6.66 | w–m |
| 15.8–15.9 | 5.61–5.57 | vw |
| 17.2–17.3 | 5.16–5.13 | s |
| 17.8 | 4.98 | w |
| 21.0 | 4.23 | s |
| 21.8 | 4.08 | vs |
| 23.1–23.2 | 2.85–3.83 | w |
| 23.5–23.6 | 3.79–3.77 | vw |
| 25.0 | 3.56 | vw |
| 26.7–26.8 | 3.34–3.33 | w |
| 28.4–28.5 | 3.14–3.13 | w–m |
| 28.6–28.7 | 3.12–3.11 | w |
| 2.90 | 3.08 | vw |
| 32.0 –32.1 | 2.797 –2.788 | m |
| 34.5–34.6 | 2.600 –2.592 | vw–w |
| 35.7 | 2.515 | vw |
| 48.4 | 1.881 | vw |
| 49.3–49.5 | 1.848 –1.841 | vw |
| 51.3 | 1.781 | vw |
| 55.1–55.2 | 1.670 –1.664 | vw |

EXAMPLE 85

(Preparation of MnAPO-36)

The manganese aluminophosphate denominated MnAPO-36 was synthesized by the following procedure: To a mixture formed by admixing 24.9 grams of a hydrated aluminum oxide (I) with a solution of 46.2 grams of a 85% orthophosphoric acid in 92.6 grams of water, was added a solution prepared by dissolving 8.2 grams of manganese (II) acetate tetrahydrate in 25.0 grams of water. The resulting mixture was then combined with 43.0 grams of tripropylamine ($C_9H_{21}N$) to form a reaction mixture having a composition in molar oxide ratios of:

1.5$C_9H_{21}N$:0.167MnO:0.917$Al_2O_3$:$P_2O_5$:0.33$CH_3COOH$:40$H_2O$.

This reaction mixture was admixed with 2.0 grams of seed crystals of MAPO-36, i.e. MAPO-36 particles that would pass through a 325 mesh screen, and heated in a sealed reactor at 150° C. for 72 hours. The resulting solids product was recovered by filtration, washed with water and dried in air at room temperature. The X-ray powder diffraction pattern of a sample of the solids established the presense of MnAPO-36 in admixture with MnAPO-5. The diffraction pattern of MnAPO-36 was characterized by the following data:

TABLE PP

| 2θ | d, (A) | 100 × I/I$_o$ |
|---|---|---|
| 7.9 | 11.19 | 100 |
| 8.2 | 10.78 | 30 |
| 13.5 | 6.56 | 6 |
| 15.9 | 5.57 | 14 |
| 16.5 | 5.37 | 33 |
| 19.0 | 4.67 | 45 |
| 20.8 | 4.27 | shared |
| 21.7 | 4.10 | 24 |
| 22.0 | 4.04 | 37 |
| 22.9 | 3.88 | 10 |
| 23.8 | 3.74 | 11 |
| 27.1 | 3.29 | 21 |
| 28.2 | 3.16 | 12 |
| 30.2 | 2.959 | 10 (shoulder) |
| 31.9 | 2.805 | 13 |
| 34.7 | 2.585 | shared |
| 35.9 | 2.501 | 4 |

A portion of the product solids was subjected to chemical analysis. The product was found to contain 4.5 wt. % MnO, 30.5 wt. % $Al_2O_3$, 48.9 wt. % $P_2O_5$, 15.6 wt. % LOI, 7.9 wt. % C, and 1.1 wt. % N, giving a product composition in terms of molar oxide ratios of:

0.21$C_9H_{21}N$:0.18MnO:0.87$Al_2O_3$:$P_2O_5$:0.4$H_2O$ or in terms of $TO_2$ units, an essential empirical formula (anhydrous basis) of:

0.05$C_9H_{21}N$:($Mn_{0.05}Al_{0.44}P_{0.51}$)$O_2$.

EDAX microprobe analysis on clean crystals of the product having a crystal morphology characteristic of MnAPO-36 gave the following analysis based on relative peak heights.

| Average of Spot Probes | |
|---|---|
| Mn | 0.07 |
| Al | 0.41 |
| P | 0.52 |

EXAMPLE 86
(Preparation of MnAPO-36)

In another preparation of MnAPO-36, a reaction mixture was prepared by combining 46.3 grams of 85% orthophosphoric acid and 99.0 grams of water, to which was added 24.9 grams of a hydrated aluminum oxide (I). A solution prepared by dissolving 5.6 grams of manganese (II) sulfate monohydrate in 25.5 grams of water was added to the mixture followed by 57.4 grams of tripropylamine ($C_9H_{21}N$). The composition of the final reaction mixture in molar oxide ratios was:

2.0$C_9H_{21}N$:0.167MnO:0.917$Al_2O_3$:$P_2O_5$:0.167$H_2SO_4$:40$H_2O$.

The solids product obtained after heating the reaction mixture in a sealed reactor at 150° C. for 168 hours was found to be impure by X-ray analysis, but the minor phase was MnAPO-36 having a powder diffraction pattern essentially identical to that set forth in TABLE PP, above.

The species MnAPO-36 as referred to herein is a manganese aluminimophosphate material having a three-dimensional microporous crystal framework structure of $PO_2^+AlO_2^-$ and $MnO_2^{-2}$ tetrahedral units and whose essential empirical chemical composition on an anhydrous basis is: mR:($Mn_xAl_yP_z$)$O_2$ wherein "R" represents at least one organic templating agent present in the intracrystalline pore system; "m" represents the moles of "R" present per mole of ($Mn_xAl_yP_z$)$O_2$ and has a value of from zero to 0.3, "x", "y" and "z" represent respectively, the mole fractions of manganese, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said manganese aluminophosphate having a characteristic X-ray powder diffraction pattern which contains at least the d-spacings set forth below in TABLE XXXIII. In the form as synthesized in accordance with the process of this invention, "m" has a value of from 0.02 to 0.3.

TABLE XXXIII

| 2θ | d, (A) | Relative Intensity |
|---|---|---|
| 7.8–7.9 | 11.33–11.19 | vs |
| 16.3–16.5 | 5.44–5.37 | m |
| 19.0 | 4.67 | m–s |
| 22.0 | 4.04 | m |
| 27.1–27.2 | 3.29–3.28 | w–m |

All of the as-synthesized MnAPO-36 compositions for which X-ray powder diffraction patterns have been obtained at present, have X-ray patterns within the generalized pattern of Table XXXIII (a), below:

TABLE XXXIII (a)

| 2θ | d, (A) | Relative Intensity |
|---|---|---|
| 7.8 –7.9 | 11.33–11.19 | vs |
| 8.2 | 10.78 | w |
| 13.5 | 6.56 | vw |
| 15.8–15.9 | 5.61–5.57 | w |
| 16.3–16.5 | 5.44–5.37 | m |
| 19.0 | 4.67 | m–s |
| 20.8 | 4.27 | w |
| 21.7 | 4.10 | w |
| 22.0 | 4.04 | m |
| 22.9 | 3.88 | vw |
| 23.8 | 3.74 | w |
| 27.1–27.2 | 3.29–3.28 | w–m |
| 28.2 | 3.16 | w |
| 30.2 | 2.959 | vw |
| 31.8–31.9 | 2.814–2.805 | w |
| 34.7 | 2.585 | w |
| 35.9 | 2.501 | vw |

EXAMPLE 87

(Preparation of MnAPO-44)

The manganese aluminophosphate species denominated MnAPO-44 was synthesized by the following procedure: a reaction mixture was prepared by combining 46.2 grams of 85% orthophosphoric acid and 92.5 grams of water, to which was added 21.7 grams of a hydrated aluminum oxide (I). A solution prepared by dissolving 19.6 grams of manganese (II) acetate tetrahydrate in 60.1 grams of water was added to this first mixture, and to the resulting mixture 19.8 grams of cyclohexylamine ($C_6H_{13}N$) was added. The composition of the final reaction mixture in molar oxide ratios was:

$C_6H_{13}N:0.4MnO:0.8Al_2O_3:P_2O_5:0.8CH_3COOH:50 H_2O$.

The reaction mixture was heated at 150° C. for 168 hours in a sealed reactor. The solids were recovered by filtration, washed with water, and dried in air at room temperature. A portion of the solids that did not pass through a 200 mesh screen when wet was subjected to X-ray analysis and chemical analysis. The product was found to be pure and had an X-ray powder diffraction pattern characterized by the following data:

TABLE QQ

| $2\theta$ | d, (A) | $100 \times I/I_o$ |
|---|---|---|
| 9.4 | 9.41 | 100 |
| 13.0 | 6.81 | 7 |
| 13.8 | 6.42 | 2 |
| 16.0 | 5.54 | 15 |
| 17.3 | 5.13 | 2 |
| 18.9 | 4.70 | 5 |
| 20.6 | 4.31 | 41 |
| 21.6 | 4.11 | 16 |
| 22.4 | 3.97 | 3 |
| 23.0 | 3.87 | 3 |
| 24.4 | 3.65 | 22 |
| 26.1 | 3.41 | 7 |
| 27.8 | 3.21 | 5 |
| 29.6 | 3.018 | 3 |
| 30.1 | 2.969 | 8 |
| 30.7 | 2.912 | 29 |
| 32.4 | 2.763 | 1 |
| 33.0 | 2.714 | 3 |
| 35.4 | 2.536 | 3 |
| 47.9 | 1.899 | 3 |
| 48.1 | 1.892 | 2 |
| 48.5 | 1.877 | 4 |
| 50.1 | 1.821 | 4 |
| 53.7 | 1.707 | 3 |

Chemical analysis established that the solid product contained 22.2 wt. % $Al_2O_3$, 43.5 wt. % $P_2O_5$, 11.7 wt. % MnO, 12.7 wt. % C, 2.5 wt. % N and 22.0 wt. % LOI, giving an overall product composition in molar oxide ratios of $0.57C_6H_{13}N:0.54MnO:0.71Al_2O_3:P_2O_5:0.82H_2O$ which corresponds to an essential empirical formula:

$0.15C_6H_{13}N:(Mn_{0.14}Al_{0.35}P_{0.51})O_2$.

EDAX microprobe analysis of clean crystals of the product having the crystal morphology of MnAPO-44 gave the following analysis based on relative peak heights:

| | Spot Probe |
|---|---|
| Mn | 0.11 |
| Al | 0.33 |
| P | 0.56 |

The species MnAPO-44 as referred to herein is a manganese aluminophosphate material having a three-dimensional microporous crystal framework structure of $PO_2^+$, $AlO_2^-$ and $MnO_2^{-2}$ tetrahedral units and whose essential empirical chemical composition on an anhydrous basis is: $mR:(Mn_xAl_yP_z)O_2$ wherein "R" represents at least one organic templating agent present in the intracrystalline pore system; "m" represents the moles of "R" present per mole of $(Mn_xAl_yP_z)O_2$ and has a value of from zero to 0.3, "x", "y" and "z" represent respectively, the mole fractions of manganese, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said manganese aluminophosphate having a characteristic X-ray powder diffraction pattern which contains at least the d-spacings set forth below in TABLE XXXIV. In the form as synthesized in accordance with the process of this invention, "m" has a value of from 0.02 to 0.3.

TABLE XXXIV

| $2\theta$ | d, (A) | Relative Intensity |
|---|---|---|
| 9.4 | 9.41 | vs |
| 16.0 | 5.54 | w |
| 20.6 | 4.31 | m |
| 21.6 | 4.11 | w |
| 24.4 | 3.65 | w |
| 30.7 | 2.912 | w |

EXAMPLE 88

(Preparation of MnAPO-47)

(a) The manganese aluminophosphate species denominated MnAPO-47 was synthesized by the following procedure: A solution prepared by combining 8.2 grams of manganese (II) acetate tetrahydrate with 106.1 grams of water was added to 74.9 grams of aluminum isopropoxide in a high-shear blender and processed until a thick gel had formed. The final reaction mixture was formed by adding to this gel a solution of 46.2 grams of 85% orthophosphoric acid, 46.2 grams of water and 23.4 grams of diethylethanolamine ($C_6H_{15}NO$). The final composition in terms of molar oxide ratios was: $C_6H_{15}NO:0.167MnO:0.917Al_2O_3:P_2O_5:0.33CH_3COOH:5.5i-C_3H_7OH:45H_2O$ The reaction mixture was heated in a sealed reactor at 150° C. for 96 hours and the solid product isolated by filtration, washed with water and dried in air at room temperature. The X-ray powder diffraction pattern of a portion of the solids indicated a minor phase characterized by the following data:

TABLE RR

| $2\theta$ | d, (A) | $100 \times I/I_o$ |
|---|---|---|
| 9.4 | 9.41 | 100 |
| 12.8 | 6.92 | shared |
| 15.9 | 5.57 | 14 |
| 17.5 | 5.07 | 4 |
| 20.5 | 4.33 | 49 |
| 24.6 | 3.62 | shared |
| 25.8 | 3.45 | shared |
| 30.4 | 2.940 | 19 |
| 30.8 | 2.903 | 13 |

(b) Energy dispersive analysis by X-ray in conjunction with scanning electron microscope studies on clean crystals having the crystal morphology of MnAPO-47 produced the following data based on relative peak heights:

|  | Spot Probe |
|---|---|
| Mn | 0.09 |
| Al | 0.34 |
| P | 0.57 |

The species MnAPO-47 as referred to herein is a manganese aluminophosphate material having a three-dimensional microporous crystal framework structure of $PO_2^+$, $AlO_2^-$ and $MnO_2^{-2}$ tetrahedral units and whose essential empirical chemical composition on an anhydrous basis is: $mR:(Mn_xAl_yP_z)O_2$ wherein "R" represents at least one organic templating agent present in the intracrystalline pore system; "m" represents the moles of "R" present per mole of $(Mn_xAl_yP_z)O_2$ and has a value of from zero to 0.3, "x", "y" and "z" represent respectively, the mole fractios of manganese, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said manganese aluminophosphate having a characteristic X-ray powder diffraction pattern which contains at least the d-spacings set forth below in TABLE XXXV. In the form as synthesized in accordance with the process of this invention, "m" has a value of from 0.02 to 0.3.

TABLE XXXV

| $2\theta$ | d, (Å) | Relative Intensity |
|---|---|---|
| 9.4 | 9.41 | vs |
| 15.9 | 5.57 | w |
| 20.5 | 4.33 | m |
| 25.8 | 3.45 | w |
| 30.4 | 2.940 | w |

EXAMPLE 89

(Preparation of CoAPO-5)

The cobalt aluminophosphate species denominated CoAPO-5 was synthesized by the following procedure: A solution of 8.3 grams of cobalt (II) acetate tetrahydrate [$Co(CH_3CO_2)_2\cdot 4H_2O$] in 106.1 grams of water was added to 74.9 grams of aluminum isopropoxide in a high-shear blender and processed until a thick gel formed. To this gel was added a solution composed of 46.2 grams of 85% orthophosphoric acid, 46.4 grams of water, and 23.4 grams of N,N-diethylethanolamine ($C_6H_{15}NO$). This mixture was then blended at high speed until homogeneous. The composition of the final reaction mixture in molar oxide ratios was:

$C_6H_{15}NO:0.167CoO:0.917Al_2O_3:P_2O_5:0.33CH_3COOH:5.5C_3H_7OH:45H_2O$.

The reaction mixture was heated at 200° C. for 48 hours in a sealed reactor. The solids were recovered by filtration, washed with water, and dried in air at room temperature. A portion of the solids was subjected to X-ray analysis. The solid was impure but the major phase exhibited an X-ray powder diffraction pattern characterized by the following data:

TABLE SS

| $2\theta$ | d, (Å) | $100 \times I/I_o$ |
|---|---|---|
| 7.6 | 11.6 | 100 |
| 12.9 | 6.86 | 13 |
| 14.9 | 5.95 | 21 |
| 19.7 | 4.51 | 51 |
| 21.0 | 4.23 | 36 |
| 22.4 | 3.97 | 82 |
| 24.6 | 3.93 | 4 |
| 25.9 | 3.44 | 30 |
| 28.9 | 3.09 | 15 |
| 30.0 | 2.98 | 21 |
| 33.5 | 2.675 | 4 |
| 34.4 | 2.607 | 15 |
| 36.9 | 2.436 | 3 |
| 37.6 | 2.392 | 10 |
| 42.1 | 2.146 | 1 |
| 47.6 | 1.910 | 4 |

A portion of the product solids was subjected to chemical analysis. The product was found to contain 4.3 wt. % CoO, 32.4 wt. % $Al_2O_3$, 49.8 wt. % $P_2O_5$, 14.0 wt. % LOI, 5.6 wt. % C, and 1.0 wt. % N, giving a product composition in terms of molar oxide ratios of:

$0.22C_6H_{15}NO:0.16CoO:0.91Al_2O_3:P_2O_5:1.0H_2O$ or in terms of $TO_2$ units, an essential empirical formula (anhydrous basis) of:

$0.06C_6H_{15}NO:(Co_{0.04}Al_{0.46}P_{0.50})O_2$.

EXAMPLE 90

(Preparation of CoAPO-5)

CoAPO-5 was found to be templated by tetraethylammonium hydroxide (TEAOH) using the following procedure: A mixture prepared by combining 46.2 grams of 85% orthophosphoric acid and 41.4 grams of water, to which was added 25.0 grams of a hydrated aluminum oxide (I). A solution prepared by dissolving 9.3 grams cobalt sulfate heptahydrate ($CoSO_4\cdot 7H_2O$) in 30.3 grams of $H_2O$ was added to this first mixture, and to the resulting mixture 73.6 grams of aqueous 40 wt. % tetraethylammonium hydroxide was added. The composition of the final reaction mixture in molar oxide ratios was:

$TEAOH:0.167CoO:0.917Al_2O_3:P_2O_5:0.167H_2SO_4:40H_2O$.

The reaction mixture was heated in a sealed reactor at 200° C. for 168 hours. The solid product was recovered by filtration, washed with water and dried in air at room temperature. A portion of the solid was subjected to X-ray analysis. The solid was impure but the major phase had an X-ray powder diffraction pattern essentially identical to that in Example 89, above.

EXAMPLE 91

(Preparation of CoAPO-5)

(a) A solution of 14.9 grams of cobalt (II) acetate tetrahydrate in 138.6 grams of water was added to 61.3 grams of aluminum isopropoxide in a high-shear blender and blended at high speed until a thick gel formed. To this gel was added a solution composed of 46.2 grams of 85% orthophosphoric acid, 46.2 grams of water, and 28.7 grams of tripropylamino ($C_9H_{21}N$). The composition of the final reaction mixture in molar oxide ratios was:

$C_9H_{21}N:0.3CoO:0.75Al_2O_3:P_2O_5:0.6CH_3COOH:4.5C_3H_7OH:55H_2O$.

The reaction mixture was heated at 150° C. for 48 hours in a sealed reactor. The solids were recovered by filtration, washed with water, and dried in air at room temperature. A portion of the solids was subjected to X-ray analysis. The solid was impure but the major phase exhibited an X-ray powder diffraction pattern essentially identical to that of Example 89, above. EDAX microprobe analysis on clean crystals of the products having the characteristic morphology of CoAPO-5 gave the following analysis based on relative peak heights:

| Average of Spot Probes | |
|---|---|
| Co | 0.02 |
| Al | 0.45 |
| P | 0.52 |

(b) A portion of this solid was calcined in air by heating it from 100° to 600° C. at 125°/hr., then holding it at 600° C. for 2 hours. This calcined solid exhibited an X-ray powder diffraction pattern essentially identical to that in part (a), above.

(c) Adsorption capacities were measured on this calcined product using a standard McBain-Bakr gravimetric adsorption apparatus. The following data were obtained on a sample activated at 400° C:

| Adsorbate | Kinetic Diameter, A | Pressure, Torr | Temp; °C. | Wt. % Adsorbed |
|---|---|---|---|---|
| $O_2$ | 3.46 | 12 | −183 | 10.3 |
| " | " | 710 | −183 | 13.1 |
| Neopentane | 6.2 | 12 | 24 | 4.9 |
| " | " | 710 | 24 | 5.2 |
| $H_2O$ | 2.65 | 4.6 | 23 | 5.2 |
| " | " | 20.6 | 23 | 20.2 |

The pore size of the calcined product is greater than 6.2A as shown by the adsorption of neopentane.

EXAMPLE 92

(Preparation of CoAPO-5)

Using the same reagents and mixing procedures as in Example 90 above, except that diisopropylamine ($C_6H_{15}N$) was employed as the templating agent instead of TEAOH, a reaction mixture was formed having the following composition in terms of molar oxide ratios:

$C_6H_{15}N:0.167CoO:0.917Al_2O_3:P_2O_5:0.167H_2SO_4:40H_2O$.

The reaction mixture was heated at 200° C. for 24 hours in a sealed reactor. The solids were recovered by filtration, washed with water, and dried in air at room temperature. A portion of the solids were subjected to X-ray analysis. The solid was impure but a minor phase exhibited an X-ray powder diffraction pattern essentially identical to that in Example 89.

The species CoAPO-5 as referred to herein is a cobalt aluminophosphate material having a three-dimensional microporous crystal framework structure of $PO_2^+$, $AlO_2^-$ and $CoO_2^{-2}$ tetrahedral units and whose essential empirical chemical composition on an anhydrous basis is: $mR:(Co_xAl_yP_z)O_2$ wherein "R" represents at least one organic templating agent present in the intracrystalline pore system; "m" represents the moles of "R" present per mole of $(Co_xAl_yP_z)O_2$ and has a value of from zero to 0.3, "x", "y" and "z" represent respectively, the mole fractions of cobalt, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said cobalt aluminophosphate having a characteristic X-ray powder diffraction pattern which contains at least the d-spacings set forth below in TABLE XXXVI. In the form as synthesized in accordance with the process of this invention, "m" has a value of from 0.02 to 0.3.

TABLE XXXVI

| 2θ | d, (A) | Relative Intensity |
|---|---|---|
| 7.4–7.6 | 11.9–11.6 | vs |
| 12.8–12.9 | 6.92–6.86 | vw–m |
| 14.8–14.9 | 5.99–5.95 | w |
| 19.6–19.8 | 4.53–4.48 | m–s |
| 21.0–21.2 | 4.23–4.19 | w–vs |
| 22.3–22.5 | 3.99–3.95 | m–s |

All of the as-synthesized CoAPO-5 compositions for which X-ray powder diffraction data have presently been obtained have patterns which are within the generalized pattern of TABLE XXXVII below:

TABLE XXXVII

| 2θ | d, (A) | Relative Intensity |
|---|---|---|
| 7.4–7.6 | 11.9–11.6 | vs |
| 12.8–12.9 | 6.92–6.86 | vw–m |
| 14.8–14.9 | 5.99–5.95 | w |
| 19.6–19.8 | 4.53–4.48 | m–s |
| 21.0–21.2 | 4.23–4.19 | w–vs |
| 22.3–22.5 | 3.99–3.95 | m–s |
| 24.6–24.8 | 3.62–3.59 | vw |
| 25.8–26.0 | 3.45–3.43 | w–m |
| 28.9–29.1 | 3.09–3.07 | vw–w |
| 29.9–30.1 | 2.99–2.97 | w |
| 33.5–33.8 | 2.675–2.652 | vw |
| 34.4–34.6 | 2.607–2.592 | w |
| 36.8–37.0 | 2.442–2.430 | vw |
| 37.6–37.9 | 2.392–2.374 | vw |
| 47.5–47.8 | 1.914–1.903 | vw |

EXAMPLE 93

(Preparation of CoAPO-11)

The cobalt aluminophosphate species denominated CoAPO-11 was prepared by the following procedure: A mixture was formed by combining 25.0 grams of a hydrated aluminum oxide (I), 86.7 grams of water and 46.2 grams of 85% orthophosphoric acid. A solution prepared by dissolving 9.4 grams cobalt (II) sulfate heptahydrate in 30.0 grams of $H_2O$ was added to this first mixture, and to the resulting mixture 20.8 grams of diisopropylamine ($C_6H_{15}N$) was added. The composition of the final reaction mixture in molar oxide ratios was $C_6H_{15}N:0.167CoO:0.917Al_2O_3:P_2O_5:0.167H_2SO_4:40H_2O$.

The reaction mixture was heated at 200° C. for 24 hours in a sealed reactor. The solids were recovered by filtration, washed with water, and dried in air at room temperature. A portion of the solids were subjected to X-ray analysis. The solid was impure but the major phase exhibited an X-ray powder diffraction pattern characterized by the following data:

TABLE TT

| 2θ | d, (A) | 100 × I/I$_o$ |
|---|---|---|
| 8.2 | 10.8 | 20 |
| 9.5 | 9.31 | 37 |
| 13.3 | 6.66 | 10 |
| 15.8 | 5.61 | 23 |
| 16.3 | 5.44 | 3 |
| 19.1 | 4.65 | 3 |

TABLE TT-continued

| 2θ | d, (A) | 100 × I/I₀ |
|---|---|---|
| 20.4 | 4.35 | 37 |
| 21.2 | 4.19 | 100 |
| 22.3 | 3.99 | 57 |
| 22.5 | 3.95 | 50 |
| 22.8 | 3.90 | 50 |
| 23.2 | 3.83 | 67 |
| 24.8 | 3.59 | 10 |
| 26.5 | 3.36 | 27 |
| 28.7 | 3.11 | 13 |
| 31.6 | 2.83 | 7 |
| 32.8 | 2.73 | 13 |

EXAMPLE 94

(Preparation of CoAPO-11)

A solution of 8.3 grams of cobalt (II) acetate tetrahydrate in 124.2 grams of water was added to 74.9 grams of aluminum isopropoxide in a high-shear blender and processed until a thick gel was formed. To this gel was added a solution composed of 46.2 grams of 85% orthophosphoric acid, 46.2 grams of water, and 20.2 grams of diisopropylamine ($C_6H_{15}N$) and the resulting mixture then blended at high speed until homogenous. The composition of the final reaction mixture in molar oxide ratios was:

$C_6H_{15}N:0.167CoO:0.917Al_2O_3:P_2O_5:0.33CH_3CO_2H:5.5C_3H_7OH:50H_2O$.

The reaction mixture was heated at 200° C. for 168 hours, and the solids recovered by filtration, washed with water, and dried in air at room temperature. The solid was impure but the major phase exhibited an X-ray powder diffraction patten essentially identical to that in Example 93. EDAX microprobe analysis on clean crystals of the product having a crystal morphology characteristic of CoAPO-11 gave the following analysis based on relative peak heights:

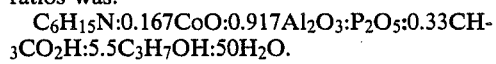

|  | Area Scan | Average of Spot Probes |
|---|---|---|
| Co | 0.05 | 0.03 |
| Al | 0.42 | 0.38 |
| P | 0.53 | 0.59 |

EXAMPLE 95

(Preparation of CoAPO-11)

Di-n-propylamine was found to template the formation of CoAPO-11 in a procedure whereby a solution of 46.2 grams of 85% orthophosphoric acid in 92.5 grams of water was combined with 21.7 grams of a hydrated aluminum oxide (I). A solution prepared by dissolving 19.9 grams of cobalt (II) acetate tetrahydrate in 60.5 grams of water was added to the reaction mixture, and to the resulting mixture 20.2 grams of di-n-propylamine ($C_6H_{15}N$) was added. The composition of the final reaction mixture in molar oxide ratios was $C_6H_{15}N:0.40CoO:0.80Al_2O_3:P_2O_5:0.8CH_3COOH:50H_2O$.

When crystallized in a sealed reactor at 150° C. for 24 hours, the reaction mixture yielded an impure solid product having a major phase which exhibited an X-ray powder diffraction pattern essentially identical to that of Example 93, above.

The species CoAPO-11 as referred to herein is a cobalt aluminophosphate material having a three-dimensional microporous crystal framework structure of $PO_2^+$, $AlO_2^-$ and $CoO_2^{-2}$ tetrahedral units and whose essential empirical chemical composition on an anhydrous basis is: $mR:(Co_xAl_yP_z)O_2$ wherein "R" represents at least one organic templating agent present in the intracrystalline pore system; "m" represents the moles of "R" present per mole of $(Co_xAl_yP_z)O_2$ and has a value of from zero to 0.3, "x", "y" and "z" represent respectively, the mole fractions of cobalt, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said cobalt aluminophosphate having a characteristic X-ray powder diffraction pattern which contains at least the d-spacings set forth below in TABLE XXXVIII. In the form as synthesized in accordance with the process of this invention, "m" has a value of from 0.02 to 0.3.

TABLE XXXVIII

| 2θ | d, (A) | Relative Intensity |
|---|---|---|
| 9.5 | 9.31 | m-s |
| 21.0-21.2 | 4.23-4.19 | vs |
| 22.1-22.3 | 4.02-3.99 | s |
| 22.5 | 3.95 | m-s |
| 22.8 | 3.90 | m-s |
| 23.2 | 3.83 | s-vs |

All of the as-synthesized CoAPO-11 compositions for which X-ray powder diffraction data have presently been obtained have patterns which are within the generalized pattern of TABLE XXXIX below:

TABLE XXXIX

| 2θ | d, (A) | Relative Intensity |
|---|---|---|
| 8.2-8.1 | 10.9-10.8 | w-m |
| 9.5 | 9.31 | m-s |
| 13.2-13.3 | 6.71-6.66 | vw-w |
| 15.7-15.8 | 5.64-5.61 | w-m |
| 16.3 | 5.44 | vw |
| 19.0-19.1 | 4.67-4.65 | vw |
| 20.3-20.4 | 4.37-4.35 | m-s |
| 21.0-21.2 | 4.23-4.19 | vs |
| 22.1-22.3 | 4.02-3.99 | s |
| 22.5 | 3.95 | m-s |
| 22.8 | 3.90 | m-s |
| 23.2 | 3.83 | s-vs |
| 24.8 | 3.59 | w |
| 26.4-26.5 | 3.38-3.36 | w |
| 28.7 | 3.11 | w-m |
| 31.5-31.6 | 2.84-2.83 | vw |
| 32.8-32.9 | 2.73-2.72 | w |
| 34.3 | 2.614 | w |
| 37.8 | 2.380 | w |

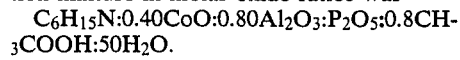

EXAMPLE 96

(Preparation of CoAPO-16)

The cobalt aluminophosphate species denominated CoAPO-16 was synthesized by the following procedure: A first mixture was prepared by combining 46.3 grams of 85% othophosphoric acid and 47.0 grams of water, to which was added 24.9 grams of a hydrated aluminum oxide (I). A solution prepared by dissolving 9.4 grams of cobalt (II) sulfate heptahydrate in 30.0 grams of water was added to the first mixture, and to the resulting mixture a solution composed of 22.3 grams of quinuclidine ($C_7H_{13}N$) and 40.4 grams of water was added. The composition of the final reaction mixture in molar oxide ratios was $C_7H_{13}N:0.167CoO:0.917Al_2O_3:P_2O_5:0.167H_2SO_4:40H_2O$.

The reaction mixture was heated at 150° C. for 24 hours in a sealed reactor. The solids were recovered by filtration, washed with water, and dried in air at room temperature. A portion of the solids that passed through a 200 mesh screen exhibited an X-ray powder diffraction pattern characterized by the following data:

TABLE UU

| $2\theta$ | d, (A) | $100 \times I/I_o$ |
|---|---|---|
| 11.4 | 7.76 | 64 |
| 18.6 | 4.77 | 49 |
| 22.0 | 4.04 | 100 |
| 22.9 | 3.88 | 11 |
| 26.6 | 3.35 | 25 |
| 29.0 | 3.08 | 11 |
| 29.8 | 3.00 | 26 |
| 32.8 | 2.73 | 4 |
| 34.9 | 2.571 | 4 |
| 38.0 | 2.368 | 9 |
| 40.0 | 2.254 | 4 |
| 48.6 | 1.873 | 8 |

A portion of this solid was found by chemical analysis to contain 4.6 wt. % CoO, 28.8 wt. % $Al_2O_3$, 43.5 wt. % $P_2O_5$, 21.9 wt. % LOI, 9.8 wt. % C, and 1.5 wt. % N, giving an overall product composition in molar oxide ratios of:

$0.38C_7H_{13}N:0.20CoO:0.92Al_2O_3:P_2O_5:1.6H_2O$ and an essential empirical formula (anhydrous basis) of:

$0.09C_7H_{13}N:(Co_{0.05}Al_{0.46}P_{0.50})O_2$.

EDAX microprobe analysis of clean crystals of the product exhibiting the characteristic morphology of CoAPO-16 gave the following analysis based on relative peak heights:

| | Average of Spot Probe |
|---|---|
| Co | 0.03 |
| Al | 0.40 |
| P | 0.57 |

EXAMPLE 97

(Preparation of CoAPO-16)

In another preparation of CoAPO-16, a solution of 46.2 grams of 85% othophosphoric acid in 36.2 grams of water was admixed with 21.7 grams of a hydrated aluminum oxide (I) and then combined with a solution of 22.5 grams of cobalt (II) sulfate heptahydrate in 70.0 grams of water. To the resulting mixture a solution consisting of 22.2 grams of quinuclidine ($C_7H_{13}N$) and 42.5 grams of water was added. The composition of the final reaction mixture in molar oxide ratios was $C_7H_{13}N:0.40CoO:0.80Al_2O_3:P_2O_5:0.40H_2SO_4:50H_2O$.

When crystallized at 150° C. for 24 hours in a sealed reactor, the resulting crystalline solids exhibited an X-ray powder diffraction pattern essentially identical to that in Example 96.

The species CoAPO-16 as referred to herein is a cobalt aluminophosphate material having a three-dimensional microporous crystal framework structure of $PO_2^+$, $AlO_2^-$ and $CoO_2^{-2}$ tetrahedral units and whose essential empirical chemical composition on an anhydrous basis is: $mR:(Co_xAl_yP_z)O_2$ wherein "R" represents at least one organic templating agent present in the intracrystalline pore system; "m" represents the moles of "R" present per mole of $(Co_xAl_yP_z)O_2$ and has a value of from zero to 0.3, "x", "y" and "z" represent respectively, the mole fractions of cobalt, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said cobalt aluminophosphate having a characteristic X-ray powder diffraction pattern which contains at least the d-spacings set forth below in TABLE XL. In the form as synthesized in accordance with the process of this invention, "m" has a value of from 0.02 to 0.3.

TABLE XL

| $2\theta$ | d, (A) | Relative Intensity |
|---|---|---|
| 11.4–11.6 | 7.76–7.63 | s |
| 18.6–18.9 | 4.77–4.70 | m |
| 22.0–22.2 | 4.04–4.00 | vs |
| 26.6–26.8 | 3.35–3.33 | w |
| 29.8–30.0 | 3.00–2.98 | w |

All of the as-synthesized CoAPO-16 compositions for which X-ray powder diffraction data has presently been obtained have X-ray patterns which are within the generalized pattern of Table XL(a), below:

TABLE XL (a)

| $2\theta$ | d, (A) | Relative Intensity |
|---|---|---|
| 11.4–11.6 | 7.76–7.63 | s |
| 18.6–18.9 | 4.77–4.70 | m |
| 22.0–22.2 | 4.04–4.00 | vs |
| 22.9–23.2 | 3.88–3.83 | vw–w |
| 26.6–26.8 | 3.35–3.33 | w |
| 29.0–29.2 | 3.08–3.06 | w |
| 29.8–30.0 | 3.00–2.98 | w |
| 32.8–33.0 | 2.73–2.714 | vw |
| 34.9–35.0 | 2.571–2.564 | vw |
| 38.0–38.1 | 2.368–2.362 | vw |
| 40.0 | 2.254 | vw |
| 48.6 | 1.873 | vw |

EXAMPLE 98

(Preparation of CoAPO-34)

(a) The cobalt aluminophosphate species denominated CoAPO-34 was synthesized using the following procedure: A solution of 22.5 grams of cobalt (II) sulfate heptahydrate and 134.6 grams of water was stirred for 2 hours, then filtered to remove traces of undissolved solids. This solution was added to 65.4 grams of aluminum isopropoxide in a high-shear blender and blended at high speed until a thick gel formed. To this gel was added 46.2 grams of 85% orthophosphoric acid, in small increments, with the blender at slow speed. Finally, 73.6 grams of aqueous 40 wt. % tetraethylammonium hydroxide (TEAOH) was added and mixed in at high speed. The composition of the final reaction mixture in molar oxide ratios was:

$TEAOH:0.40CoO:0.80Al_2O_3:P_2O_5:0.4H_2SO_4:4.8C_3H_7OH:55H_2O$.

The reaction mixture was heated at 100° C. for 66 hours. The solids were recovered by filtration, washed with water, and dried in air at room temperature. The solids exhibited an X-ray diffraction pattern characterized by the following data.

TABLE WW

| 2θ | d, (A) | 100 × I/I₀ |
|---|---|---|
| 9.5 | 9.31 | 79 |
| 12.8 | 6.92 | 19 |
| 14.1 | 6.28 | 16 |
| 16.0 | 5.54 | 43 |
| 18.0 | 4.93 | 29 |
| 20.6 | 4.31 | 100 |
| 22.2 | 4.00 | 5 |
| 23.0 | 3.87 | 3 |
| 25.2 | 3.53 | 30 |
| 25.8 | 3.45 | 21 |
| 27.5 | 3.24 | 5 |
| 28.3 | 3.15 | 5 |
| 29.5 | 3.03 | 5 |
| 30.5 | 2.93 | 38 |
| 31.2 | 2.87 | 25 |
| 33.8 | 2.65 | 3 |
| 34.3 | 2.614 | 10 |
| 36.2 | 2.481 | 5 |
| 39.6 | 2.276 | 3 |
| 43.0 | 2.103 | 3 |
| 43.3 | 2.090 | 3 |
| 47.4 | 1.918 | 4 |
| 49.0 | 1.859 | 6 |
| 50.9 | 1.794 | 5 |
| 53.0 | 1.728 | 3 |

By chemical analysis the solids were formed to contain 8.2 wt. % CoO, 26.6 wt. % $Al_2O_3$, 46.2 wt. % $P_2O_5$, 18.9 wt. % LOI, 10.0 wt. % C, and 1.4 wt. % N, giving a composition in molar oxide ratios of 0.32TEAOH:0.34CoO:0.80$Al_2O_3$:$P_2O_5$:0.9$H_2O$ and a formula (anhydrous basis) of 0.08TEAOH:($Co_{0.09}Al_{0.41}P_{0.51}$)$O_2$.

EDAX microprobe analysis on clean crystals of the solids having the crystal morphology characteristic of CoAPO-34 gave the following results based on relative peak heights:

| | Average of Spot Probe |
|---|---|
| Co | 0.06 |
| Al | 0.36 |
| P | 0.58 |

(b) a portion of the solid of part (a) was calcined in air by heating it from 100° to 500° C. at 125°/hr., then holding it at 500° C. for 2 hours. This calcined solid exhibited an X-ray powder diffraction pattern characterized by the following data:

TABLE YY

| 2θ | d, (A) | 100 × I/I₀ |
|---|---|---|
| 9.7 | 9.12 | 100 |
| 13.1 | 6.76 | 35 |
| 14.3 | 6.19 | 3 |
| 16.3 | 5.44 | 19 |
| 18.2 | 4.87 | 19 |
| 19.4 | 4.58 | 3 |
| 21.0 | 4.23 | 43 |
| 22.5 | 3.95 | 3 |
| 23.5 | 3.79 | 3 |
| 25.5 | 3.49 | 14 |
| 26.4 | 3.38 | 16 |
| 28.8 | 3.10 | 5 |
| 31.2 | 2.87 | 24 |
| 31.7 | 2.82 | 11 |

(c) Adsorption capacities were measured on the calcined product of part (b) using a standard McBain-Baker gravimetric apparatus. The following data were obtained on a sample activated at 350° C.:

| Adsorbate | Kinetic Diameter, A | Pressure Torr | Temp., °C. | Wt. % Adsorbed |
|---|---|---|---|---|
| $O_2$ | 3.46 | 11 | −183 | 21.9 |
| $O_2$ | 3.46 | 684 | −183 | 25.4 |
| Butane | 4.3 | 746 | 23 | 9.2* |
| Xenon | 4.0 | 759 | 23 | 21.7 |
| $H_2O$ | 2.65 | 4.6 | 25 | 28.6 |
| | | 21 | 23 | 32.9 |

*Slow adsorption, not at equilibrium

The pore size of the calcined product is approximately 4.3 A as shown by the slow adsorption of butane.

EXAMPLE 99

(Preparation of CoAPO-34)

In another preparation of CoAPO-34, a first mixture was prepared by combining 46.2 grams of 85% orthophosphoric acid in 41.4 grams of water with 25.0 grams of a hydrated aluminum oxide (I). A solution prepared by dissolving 9.3 grams of cobalt (II) sulfate heptahydrate in 30.3 grams of water was added to this first mixture and to the resulting mixture 73.6 grams of aqueous 40 wt % tetraethylammonium hydroxide (TEAOH) was added. The composition of the final reaction mixture in molar oxide ratios was TEAOH:0.167CoO:0.9-17$Al_2O_3$:$P_2O_5$:0.167$H_2SO_4$:40$H_2O$. When crystallized at 150° C. for 24 hours in a sealed reactor the product solids exhibited an X-ray powder diffraction pattern essentially identical to that of Example 98(a).

EXAMPLE 100

(Preparation of CoAPO-34)

A solution was prepared by combining 14.9 grams of cobalt (II) acetate tetrahydrate with 140.0 grams of water. This solution was added to 69.5 grams of aluminum isopropoxide in a high-shear blender and blended at high speed until a thick gel formed. To this gel was added a solution composed of 46.2 grams of 85% orthophosphoric acid, 46.2 grams of water, and 20.2 grams of diisopropylamine ($C_6H_{15}N$). This mixture was then blended at high speed until homogeneous. The composition of the final reaction mixture in molar oxide ratios was:

$C_6H_{15}N$:0.30CoO:0.85$Al_2O_3$:$P_2O_5$:0.60$CH_3COOH$:5.1$C_3H_7OH$:55$H_2O$.

The reaction mixture was heated at 150° C. for 96 hours in a sealed reactor. The solids were recovered by filtration, washed with water, and dried in air at room temperature. The solid was impure but the major phase exhibited an X-ray powder diffraction pattern essentially identical to that of the as synthesized product in Example 98(a).

The species CoAPO-34 as referred to herein is a cobalt aluminophosphate material having a three-dimensional microporous crystal framework structure of $PO_2^+$, $AlO_2^-$ and $CoO_2^{-2}$ tetrahedral units and whose essential empirical chemical composition on an anhydrous basis is: mR:($Co_xAl_yP_z$)$O_2$ wherein "R" represents at least one organic templating agent present in the intracrystalline pore system; "m" represents the moles of "R" present per mole of ($Co_xAl_yP_z$)$O_2$ and has a value of from zero to 0.3, "x", "y" and "z" represent respectively, the mole fractions of cobalt, aluminum and phosphorus present in the oxide moiety, said mole fractions being within the compositional area bounded by points, A, B, C and D on the ternary diagram which is FIG. 1, or preferably within the area bounded by points a, b, c and d on the ternary diagram which is FIG. 2, said cobalt aluminophosphate having a characteristic X-ray powder diffraction pattern which contains at least the d-spacings set forth below in TABLE XLI. In the form as synthesized in accordance with the process of this invention, "m" has a value of from 0.02 to 0.3.

TABLE XLI

| $2\theta$ | d, (A) | Relative Intensity |
|---|---|---|
| 9.5–9.7 | 9.31–9.12 | s–vs |
| 12.8–13.1 | 6.92–6.76 | w–m |
| 15.9–16.3 | 5.57–5.44 | w–m |
| 20.4–20.8 | 4.35–4.27 | m–vs |
| 25.2–25.5 | 3.53–3.49 | w–m |
| 30.3–31.2 | 2.95–2.87 | w–m |

All of the as-synthesized CoAPO-34 compositions for which X-ray powder diffraction data has presently been obtained have X-ray patterns within the generalized pattern of Table XLI (a), below:

TABLE XLI (a)

| $2\theta$ | d, (A) | Relative Intensity |
|---|---|---|
| 9.5–9.7 | 9.31–9.12 | s–vs |
| 12.8–13.1 | 6.92–6.76 | w–m |
| 14.0–14.3 | 6.33–6.19 | vw–w |
| 15.9–16.3 | 5.57–5.44 | w–m |
| 17.9–18.2 | 4.96–4.87 | vw–m |
| 20.4–20.8 | 4.35–4.27 | m–vs |
| 22.1–22.5 | 4.02–3.95 | vw–w |
| 23.0–23.5 | 3.87–3.79 | vw |
| 25.2–25.5 | 3.53–3.49 | w–m |
| 25.7–26.4 | 3.47–3.38 | w |
| 27.4–28.0 | 3.25–3.19 | vw |
| 28.3–28.8 | 3.15–3.10 | vw |
| 29.4–29.5 | 3.04–3.03 | vw |
| 30.3–31.2 | 2.95–2.87 | w–m |
| 31.2–31.7 | 2.87–2.28 | w |
| 33.8 | 2.652 | vw |
| 34.2–34.3 | 2.622–2.614 | vw |
| 36.2 | 2.481 | vw |
| 39.5–39.6 | 2.281–2.276 | vw |
| 43.0 | 2.103 | vw |
| 43.3 | 2.090 | vw |
| 47.4 | 1.918 | vw |
| 49.0 | 1.859 | vw |
| 50.7–50.8 | 1.801–1.797 | vw |

EXAMPLE 101

(Preparation of CoAPO-35)

(a) the cobalt aluminophosphate species denominated CoAPO-35 was synthesized using the following procedure:

A solution was prepared by combining 19.9 grams of cobalt (II) acetate tetrahydrate, 125 grams of water, and 46.2 grams of 85% orthophosphoric acid. A second solution containing 22.2 grams of quinuclidine ($C_7H_{13}N$) and 41.7 grams of water was added to the first. The combined solution was added to 65.4 grams of aluminum isopropoxide in a high-shear blender and blended at high speed until homogeneous. The composition of the final reaction mixture in molar oxide ratios was:

$C_7H_{13}N:0.40CoO:0.80Al_2O_3:P_2O_5:0.8CH_3COOH:4.8C_3H_7OH:50H_2O$.

The reaction mixture was heated at 100° C. for 72 hours in a sealed reactor. The solids were recovered by filtration, washed with water, and dried in air at room temperature. The solids exhibited an X-ray powder diffraction pattern characterized by the following data:

TABLE ZZ

| $2\theta$ | d, (A) | 100 × I/I$_o$ |
|---|---|---|
| 8.6 | 10.3 | 21 |
| 11.0 | 8.04 | 48 |
| 11.8 | 7.50 | 3 |
| 13.3 | 6.66 | 27 |
| 15.9 | 5.57 | 9 |
| 17.3 | 5.13 | 79 |
| 17.8 | 4.98 | 12 |
| 21.2 | 4.19 | 58 |
| 21.9 | 4.06 | 100 |
| 23.2 | 3.83 | 21 |
| 23.7 | 3.75 | 9 |
| 25.1 | 3.55 | 6 |
| 26.9 | 3.31 | 24 |
| 28.6 | 3.12 | 27 |
| 28.8 | 3.10 | Shoulder |
| 32.2 | 2.78 | 48 |
| 34.7 | 2.585 | 9 |
| 35.8 | 2.508 | 6 |
| 48.6 | 1.873 | 9 |
| 49.5 | 1.841 | 6 |
| 51.5 | 1.774 | 6 |
| 55.5 | 1.656 | 6 |

By chemical analysis the solids were found to contain 9.1 wt. % CoO, 22.5 wt. % $Al_2O_3$, 43.1 wt. % $P_2O_5$, 23.1 wt. % LOI, 9.7 wt. % C, and 1.6 wt. % N, giving a composition in molar oxide ratios of $0.38C_7H_{13}N:0.40CoO:0.73Al_2O_3:P_2O_5:1.9H_2O$ and an essential empirical formula (anhydrous basis) of:

$0.10C_7H_{13}N:(Co_{1.10}Al_{0.38}P_{0.52})O_2$.

(b) A portion of the solid of part (a) was calcined in a $CO_2$ atmosphere at 600° C. for 3.5 hours. The calcined solid exhibited an X-ray powder diffraction pattern essentially identical to that above.

(c) Adsorption capacities were measured on this calcined product using a standard McBain-Baker gravimetric apparatus. The following data were obtained on a sample activated at 380° C.:

| Adsorbate | Kinetic Diameter, A | Pressure, Torr | Temp., °C. | Wt. % Adsorbed |
|---|---|---|---|---|
| $O_2$ | 3.46 | 13 | −183 | 8.2 |
| $O_2$ | 3.46 | 710 | −183 | 11.4 |
| $H_2O$ | 2.65 | 4.6 | 24 | 14.3 |
| $H_2O$ | 2.65 | 20.3 | 23 | 21.4 |
| Butane | 4.3 | 751 | 24 | 0.1 |

The pore size of the calcined product is approximately 3.5 A based on adsorption of oxygen and exclusion of butane.

EXAMPLE 102

(Preparation of CoAPO-35)

In another preparation of CoAPO-35, a solution of 22.5 grams of cobalt (II) sulfate heptahydrate in 135.9 grams of water was added to 65.5 grams of aluminum isopropoxide in a high-shear blender and the resulting mixture blended at high speed until a thick gel formed. To this gel was added 46.2 grams of 85% orthophosphoric acid, in small increments, with the blender at slow speed. Finally, a solution consisting of 22.2 grams of quinuclidine ($C_7H_{13}N$) in 44.4 grams of water was added. This mixture was then blended at high speed until homogeneous. The composition of the final reaction mixture in molar oxide ratios was:

$C_7H_{13}N:0.40CoO:0.80Al_2O_3:P_2O_5:0.40H_2SO_4:4.8C_3H_7OH:55H_2O$.

The reaction mixture was heated to 100° C. for 189 hours. The solids were recovered by filtration, washed with water, and dried in air at room temperature. The solid was found to be impure but the major phase exhibited an X-ray powder diffraction pattern essentially identical to that in Example 101.

The species CoAPO-35 as referred to herein is a cobalt aluminophosphate material having a three-dimensional microporous crystal framework structure of $PO_2^+$, $AlO_2^-$ and $CoO_2^{-2}$ tetrahedral units and whose essential empirical chemical composition on an anhydrous basis is: $mR:(Co_xAl_yP_z)O_2$ wherein "R" represents at least one organic templating agent present in the intracrystalline pore system; "m" represents the moles of "R" present per mole of $(Co_xAl_yP_z)O_2$ and has a value of from zero to 0.3, "x", and "y" and "z" represent respectively, the mole fractions of cobalt, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said cobalt aluminophosphate having a characteristic X-ray powder diffraction pattern which contains at least the d-spacings set forth below in TABLE XLII. In the form as synthesized in accordance with the process of this invention, "m" has a value of from 0.02 to 0.3.

TABLE XLII

| $2\theta$ | d, (A) | Relative Intensity |
|---|---|---|
| 11.0–11.1 | 8.04–7.97 | m–vs |
| 13.3–13.6 | 6.66–6.51 | w–s |
| 17.2–17.5 | 5.16–5.07 | m–vs |
| 21.1–21.2 | 4.21–4.19 | m–s |
| 21.9–22.2 | 4.06–4.00 | s–vs |
| 32.0–32.4 | 2.80–2.76 | m–s |

All of the as-synthesized CoAPO-35 compositions for which X-ray powder diffraction data have presently been obtained, have X-ray patterns within the generalized pattern of Table XLII (a), below:

TABLE XLII (a)

| $2\theta$ | d, (A) | Relative Intensity |
|---|---|---|
| 8.6–8.8 | 10.3–10.0 | w–m |
| 11.0–11.1 | 8.04–7.97 | m–vs |
| 11.7–11.8 | 7.56–7.50 | vw |
| 13.3–13.6 | 6.66–6.51 | w–s |
| 15.8–16.1 | 5.61–5.50 | vw |
| 17.2–17.5 | 5.16–5.07 | m–vs |
| 17.8 | 4.98 | w |
| 21.1–21.2 | 4.21–4.19 | m–s |
| 21.9–22.2 | 4.06–4.00 | s–vs |
| 23.1–23.5 | 3.85–3.79 | w |
| 23.7 | 3.75 | vw |
| 25.0–25.1 | 3.56–3.55 | vw |
| 267.8–27.2 | 3.33–3.28 | w |
| 28.4–28.6 | 3.14–3.12 | w–m |
| 28.7–28.8 | 3.11–3.10 | w |
| 32.0–32.4 | 2.80–2.76 | m–s |
| 34.6–34.7 | 2.592–2.585 | vw–w |
| 35.8 | 2.508 | vw |
| 48.5–48.6 | 1.877–1.873 | vw |
| 51.5–51.6 | 1.774–1.771 | vw |
| 55.2–55.5 | 1.664–1.656 | vw |

EXAMPLE 103

(Preparation of CoAPO-36)

(a) The cobalt aluminophosphate species denominated CoAPO-36 was synthesized using the following procedure: To a solution of 46.2 grams of 85% orthophosphoric acid in 88.3 grams of water was added 24.9 grams of a hydrated aluminum oxide (I). A solution prepared by dissolving 8.3 grams of cobalt (II) acetate tetrahydrate in 30.0 grams of water was added to the first mixture, and to the resulting mixture 43.0 grams of tripropylamine ($C_9H_{21}N$) was added. The composition of the final reaction mixture in molar oxide ratios was $1.5C_9H_{21}N:0.167CoO:0.917Al_2O_3:P_2O_5:0.33CH_3CO_2H:40H_2O$.

The reaction mixture was seeded with 2.0 grams of MAPO-36 particles that had passed through a 325 mesh screen, and crystallized at 150° C. for 72 hours in a sealed reactor. The product solids were recovered by filtration washed with water and dried in air at room temperature. The solids exhibited an X-ray powder diffraction pattern characterized by the following data:

TABLE AB

| $2\theta$ | d,(A) | $100 \times I/I_o$ |
|---|---|---|
| 7.9 | 11.2 | 100 |
| 8.1 | 10.9 | shoulder |
| 13.5 | 6.56 | 5 |
| 15.9 | 5.57 | 12 |
| 16.5 | 5.37 | 33 |
| 19.1 | 4.65 | 57 |
| 20.8 | 4.27 | 40 |
| 21.7 | 4.10 | shoulder |
| 22.0 | 4.04 | 45 |
| 22.5 | 3.95 | 45 |
| 22.9 | 3.88 | shoulder |
| 23.9 | 3.72 | 12 |
| 27.2 | 3.28 | 19 |
| 27.6 | 3.23 | 10 |
| 28.2 | 3.16 | 10 |
| 29.0 | 3.08 | 10 |
| 30.2 | 2.96 | 7 |
| 31.9 | 2.805 | 10 |
| 34.8 | 2.578 | 21 |
| 35.8 | 2.508 | 2 |

Chemical analysis of the solids showed 4.5 wt.% CoO, 31.9 wt.% $Al_2O_3$, 46.8 wt.% $P_2O_5$, 15.9 wt.% LOI, 8.1 wt.% C, and 1.1 wt.% N, giving a composition in molar oxide ratios of:

$0.23C_9H_{21}N:0.18CoO:0.95Al_2O_3:P_2O_5:0.9H_2O$ and an essential empirical formula (anhydrous basis) of $0.06C_9H_{21}N:(Co_{0.05}Al_{0.47}P_{0.49})O_O$.

This solid also contains 0.06 wt.% MgO due to the MAPO-36 added.

EDAX microprobe analysis on clean crystals of the solids having a crystal morphology characteristic of CoAPO-36, gave the following analysis based on relative peak heights:

| | Area Scan | Average of Spot Probes |
|---|---|---|
| Co | .03 | .03 |
| Al | .44 | .41 |
| P | .54 | .56 |

(b) A portion of this solid was calcined in air by heating from 100° to 500° C. at 100°/hr then heating at 500° for 4 hours. The calcined solid exhibited an X-ray powder diffraction pattern essentially identical to that of the as-synthesized product in part (a) above.

(c) Adsorption capacities were measured on this calcined product using a standard McBain-Bakr gravimetric apparatus. The following data were obtained on a sample activated at 370° C.:

| Adsorbate | Kinetic Diameter, A | Pressure, Torr | Temp., °C. | Wt. % Adsorbed |
|---|---|---|---|---|
| O$_2$ | 3.46 | 12 | −183 | 15.0 |
| O$_2$ | 3.46 | 710 | −183 | 23.7 |
| Neopentane | 6.2 | 12 | 24 | 5.4 |
| Neopentane | 6.2 | 710 | 24 | 7.6 |
| H$_2$O | 2.65 | 4.6 | 23 | 18.6 |
| H$_2$O | 2.65 | 20.6 | 23 | 29.5 |

The pore size of the calcined product is greater than 6.2 A based on the absorption of neopentane.

EXAMPLE 104

(Preparation of CoAPO-36)

In another preparation of CoAPO-36, 25.0 grams of a hydrated aluminum oxide (I) was added to a solution of 46.3 grams of 85% orthophosphoric acid in 86.0 grams of water, and thereafter was added a solution prepared by dissolving 9.4 grams of cobalt (II) sulfate heptahydrate in 30.0 grams of water. To the resulting mixture of 28.8 grams of tripropylamine (C$_9$H$_{21}$N) was added. The composition of the final reaction mixture in molar oxide ratios was

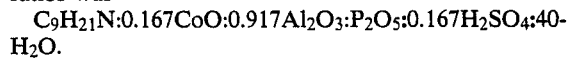

C$_9$H$_{21}$N:0.167CoO:0.917Al$_2$O$_3$:P$_2$O$_5$:0.167H$_2$SO$_4$:40H$_2$O.

After crystallization at 150° C. for 24 hours in a sealed reactor the product solids, isolated by centrifugation and water-washed, contained a minor phase exhibiting an X-ray powder diffraction pattern essentially identical to that of the product of Example 103, above.

The species CoAPO-36 as referred to herein is a cobalt aluminophosphate material having a three-dimensional microporous crystal framework structure of PO$_2$$^+$, AlO$_2$$^−$ and CoO$_2$$^{-2}$ tetrahedral units and whose essential empirical chemical composition on an anhydrous basis is: mR:(Co$_x$Al$_y$P$_z$)O$_2$ where "R" represents at least one organic templating agent present in the intracrystalline pore system; "m" represents the moles of "R" present per mole of (Co$_x$Al$_y$P$_z$)O$_2$ and has a value of from zero to 0.3, "x", "y" and "z" represent respectively, the mole fractions of cobalt, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said cobalt aluminophosphate having a characteristic X-ray powder diffraction pattern which contains at least the d-spacing set forth below in TABLE XLIII. In the form as synthesized in accordance with the process of this invention, "m" has a value of from 0.02 to 0.03.

TABLE XLIII

| 2θ | d, (A) | Relative Intensity |
|---|---|---|
| 7.9–8.0 | 11.2–11.1 | vs |
| 8.1–8.2 | 10.9–10.8 | shoulder |
| 16.5–16.6 | 5.37–5.34 | w-m |
| 19.1–19.3 | 4.65–4.60 | m-s |
| 20.8–20.9 | 4.27–4.25 | w-m |

TABLE XLIII-continued

| 2θ | d, (A) | Relative Intensity |
|---|---|---|
| 22.3–22.5 | 3.99–3.95 | w-m |

All of the as-synthesized CoAPO-36 compositions for which X-ray powder diffraction data have presently been obtained, have X-ray patterns within the generalized pattern of Table XLIII (a), below:

TABLE XLIII (a)

| 2θ | d, (A) | Relative Intensity |
|---|---|---|
| 7.9–8.0 | 11.2–11.1 | vs |
| 8.1–8.2 | 10.9–10.8 | shoulder |
| 13.5–13.6 | 6.56–6.51 | vw |
| 15.9–16.0 | 5.57–5.54 | vw-w |
| 16.5–16.6 | 5.37–5.34 | w-m |
| 19.1–19.3 | 4.65–4.60 | m-s |
| 20.8–20.9 | 4.27–4.25 | w-m |
| 21.5–21.7 | 4.13–4.10 | shoulder |
| 21.8–22.0 | 4.08–4.04 | shoulder |
| 22.3–22.5 | 3.99–3.95 | w-m |
| 22.9 | 3.88 | shoulder |
| 23.9–24.0 | 3.72–3.71 | vw-w |
| 27.2 | 3.28 | w |
| 27.6 | 3.23 | vw |
| 28.2–28.4 | 3.16–3.14 | vw |
| 29.0–29.2 | 3.08–3.06 | vw |
| 30.2–30.5 | 2.96–2.93 | vw |
| 31.9–32.0 | 2.81–2.80 | vw |
| 34.8–35.1 | 2.58–2.557 | w |
| 35.8–36.2 | 2.508–2.481 | vw |

EXAMPLE 105

(Preparation of CoAPO-44)

(a) The cobalt aluminophosphate species denominated CoAPO-44 was synthesized using cyclohexylamine as the templating agent using the following procedure: 21.7 grams of a hydrated aluminum oxide (I) was combined with a solution of 46.2 grams of 85% orthophosphoric acid in 92.4 grams of water, and thereafter admixed with a solution of 19.9 grams of cobalt (II) acetate tetrahydrate in 60.2 grams of water. To the resulting mixture was added 19.8 grams of cyclohexylamine (C$_6$H$_{13}$N) to form the final reaction mixture which had a composition, in terms of molar oxide ratios of: C$_6$H$_{13}$N:0.40CoO:0.80Al$_2$O$_3$:P$_2$O$_5$:0.80CH$_3$COOH:50H$_2$O The reaction mixture was crystallized by heating for 24 hours at 150° C. in a sealed reactor, and the product solids recovered by filtration, washed with water and dried in air at room temperature. By X-ray analysis the solids were found to be impure but the major phase exhibited a powder diffraction pattern characterized by the following data:

TABLE AC

| 2θ | d, (A) | 100 × I/I$_o$ |
|---|---|---|
| 9.4 | 9.41 | 100 |
| 13.0 | 6.81 | 13 |
| 13.8 | 6.42 | 1 |
| 16.1 | 5.50 | 41 |
| 17.3 | 5.13 | 2 |
| 19.0 | 4.67 | 5 |
| 20.7 | 4.29 | 77 |
| 21.7 | 4.10 | 77 |
| 22.4 | 3.97 | 6 |
| 23.0 | 3.87 | 8 |
| 24.4 | 3.65 | 59 |
| 26.1 | 3.41 | 18 |
| 27.8 | 3.21 | 10 |
| 29.6 | 3.02 | 5 |

TABLE AC-continued

| 2θ | d, (A) | 100 × I/I₀ |
|---|---|---|
| 30.0 | 2.98 | 18 |
| 30.7 | 2.91 | 59 |
| 32.4 | 2.76 | 5 |
| 32.9 | 2.72 | 8 |
| 35.5 | 2.53 | 10 |
| 48.0 | 1.895 | 8 |
| 48.6 | 1.873 | 5 |
| 50.1 | 1.821 | 10 |
| 53.7 | 1.707 | 5 |

(b) An identical reaction mixture as in part (a) above was heated at 150° C. for 168 hours and yielded a crystalline product having an X-ray powder diffraction pattern essentially identical to that set forth in TABLE AC. Chemical analysis of this product revealed its chemical composition to be 10.3 wt. % CoO, 26.5 wt. % Al$_2$O$_3$, 46.8 wt. % P$_2$O$_5$, 16.4 wt. % LOI, 9.6 wt. % C, and 1.9 wt. % N, giving a product composition in terms of molar oxide ratios of:

0.40C$_6$H$_{13}$N:0.42CoO:0.79Al$_2$O$_3$:P$_2$O$_5$:0.6H$_2$O or in terms of TO$_2$ units, an essential empirical formula (anhydrous basis) of:

0.10C$_6$H$_{13}$N:(Co$_{0.10}$Al$_{0.39}$P$_{0.50}$)O$_2$.

EDAX microprobe analysis on clean crystals of the solid product having a crystal morphology characteristic of CoAPO-44 gave the following analysis based on relative peak heights:

| | Average of Spot Probes |
|---|---|
| Co | 0.09 |
| Al | 0.32 |
| P | 0.59 |

Figure 2:
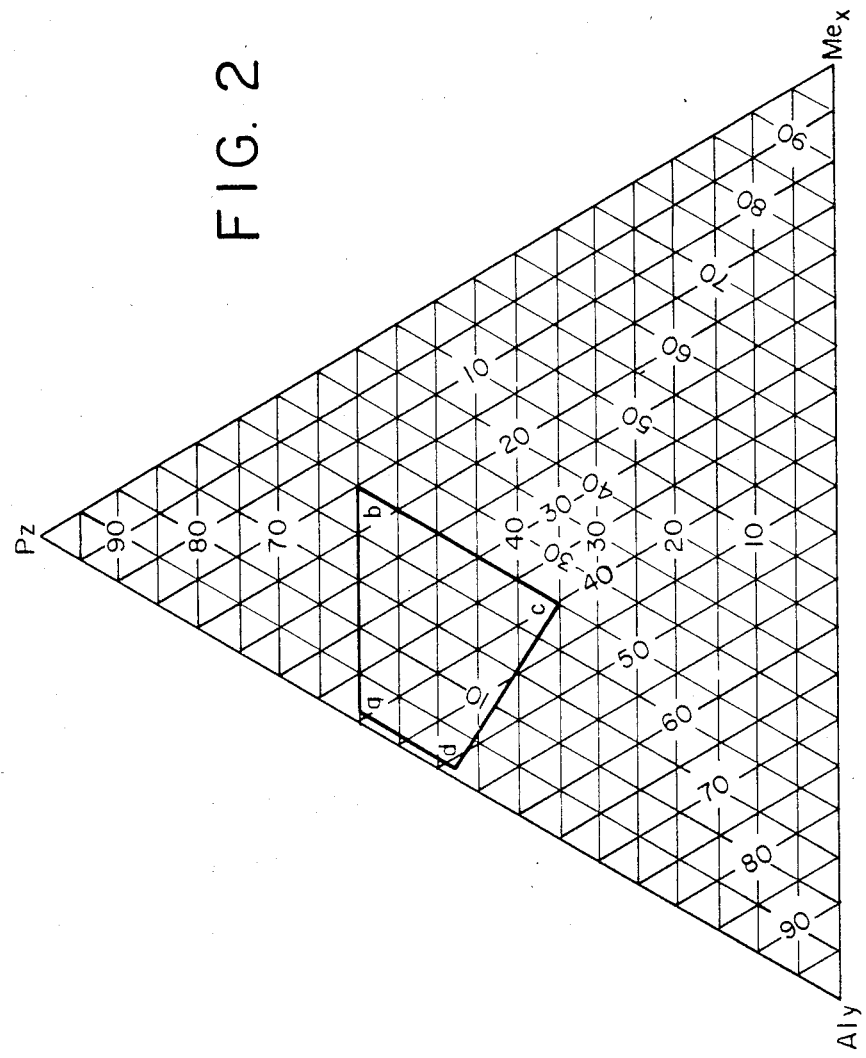
FIG. 2 is a ternary diagram wherein parameters relating to preferred compositions are set forth as mole fractions

The species CoAPO-44 as referred to herein is a cobalt aluminophospyhate material having a three-dimensional microporous crystal framework structure of PO$_2^+$, AlO$_2^-$ and CoO$_2^{-2}$ tetrahedral units and whose essential empirical chemical composition on an anhydrous basis is: mR:(Co$_x$Al$_y$P$_z$)O$_2$ and has a value of from zero to 0.3, "x", "y" and "z" represent respectively, the mole fractions of cobalt, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said cobalt aluminophosphate having a characteristic X-ray powder diffraction pattern which contains at least the d-spacing set forth below in TABLE XLIV. In the form as synthesized in accordance with the process of this invention, "m" has a value of from 0.02 to 0.3.

TABLE XLIV

| 2θ | d, (A) | Relative Intensity |
|---|---|---|
| 9.4 | 9.41 | vs |
| 16.1 | 5.50 | w-m |
| 20.7 | 4.29 | s |
| 21.7–21.8 | 4.10–4.08 | s |
| 24.4 | 3.65 | s |
| 30.7–30.8 | 2.91–2.90 | m-s |

All of the as-synthesized CoAPO-44 compositions for which X-ray powder diffraction data have presently been obtained, have X-ray patterns within the generalized pattern of Table XLIV (a), below:

TABLE XLIV (a)

| 2θ | d, (A) | Relative Intensity |
|---|---|---|
| 9.4 | 9.41 | vs |
| 12.9–13.0 | 6.86–6.81 | w |
| 13.7–13.8 | 6.46–6.42 | vw |
| 16.1 | 5.50 | w-m |
| 17.3–17.4 | 5.13–5.10 | vw |
| 19.0 | 4.67 | vw |
| 20.7 | 4.29 | s |
| 21.7–21.8 | 4.10–4.08 | s |
| 22.4 | 3.97 | vw |
| 23.0 | 3.87 | vw |
| 24.4 | 3.65 | s |
| 26.1 | 3.41 | w |
| 27.8 | 3.21 | vw |
| 29.6 | 3.02 | vw |
| 30.0–30.1 | 2.98–2.97 | w |
| 30.7–30.8 | 2.91–2.90 | m-s |
| 32.4 | 2.76 | vw |
| 32.8–32.9 | 2.73–2.72 | vw |
| 35.5 | 2.53 | vw |
| 47.9–48.0 | 1.899–1.895 | vw |
| 48.5–48.6 | 1.877–1.873 | vw |
| 50.1 | 1.821 | vw |
| 53.6–53.7 | 1.710–1.707 | vw |

EXAMPLE 106

(Preparation of CoAPO-47)

The cobalt aluminophosphate species denominated CoAPO-47 was synthesized by the following procedures: A solution of 8.3 grams of cobalt (II) acetate tetrahydrate in 106.2 grams of water was added to 74.9 grams of aluminum isopropoxide in a high-shear blender, and processed until a thick gel formed. To this gel was added a solution composed of 46.2 grams of 85% orthophosphoric acid, 46.2 grams of water, and 46.8 grams of N,N-diethylethanolamine (C$_6$H$_{15}$NO) and the resulting mixture was then blended at high speed until homogeneous. The composition of the final reaction mixture in molar oxide ratios was:

2.0C$_6$H$_{15}$NO:0.167CoO:0.917Al$_2$O$_3$:P$_2$O$_5$:0.33CH$_3$COOH:5.5C$_3$H$_7$OH:45H$_2$O.

The reaction mixture was heated at 150° C. for 120 hours in a sealed reactor. A solid product was separated from unreacted gel by repeatedly slurrying the solids in fresh water and allowing the denser crystalline fraction to settle out. This fraction was then dried in air at room temperature. By X-ray analysis the solid product was found to be substantially pure CoAPO-47 and to have an X-ray powder diffraction pattern characterized by the following data:

TABLE AD

| 2θ | d, (A) | 100 × I/I₀ |
|---|---|---|
| 9.4 | 9.41 | 100 |
| 12.9 | 6.86 | 7 |
| 14.0 | 6.33 | 4 |
| 16.1 | 5.50 | 11 |
| 17.6 | 5.04 | 3 |
| 19.0 | 4.67 | 12 |
| 20.6 | 4.31 | 45 |
| 21.9 | 4.06 | 4 |
| 22.4 | 3.97 | 1 |
| 23.0 | 3.87 | 3 |
| 24.7 | 3.60 | 14 |
| 25.9 | 3.44 | 10 |
| 27.6 | 3.23 | 3 |
| 28.0 | 3.19 | 2 |
| 29.5 | 3.03 | 3 |
| 30.6 | 2.92 | 21 |
| 30.9 | 2.89 | shoulder |
| 33.3 | 2.69 | 2 |

TABLE AD-continued

| 2θ | d, (A) | 100 × I/I₀ |
|---|---|---|
| 34.5 | 2.600 | 2 |
| 35.8 | 2.508 | 3 |
| 38.5 | 2.338 | 8 |
| 39.7 | 2.270 | 2 |
| 42.6 | 2.122 | 1 |
| 47.6 | 1.910 | 1 |
| 48.6 | 1.873 | 24 |
| 50.3 | 1.814 | 5 |
| 53.2 | 1.722 | 2 |

EXAMPLE 107

(Preparation of CoAPO-47)

Using the same reagents and mixing procedures as in Example 105, above, a reaction mixture containing a larger proportion of cobalt was prepared having the following compositon in terms of molar oxide ratios:

$2.0C_6H_{15}NO:0.40CoO:0.80Al_2O_3:P_2O_5:0.80CH_3COOH:4.8i-C_3H_7OH:50H_2O$.

The reaction mixture was heated in a sealed reactor for 48 hours at 150° C. and the solids recovered by the same procedure as in Example 106. By X-ray analysis the product was found to be pure CoAPO-47 and exhibited a powder diffraction pattern essentially identical to that of TABLE AD. EDAX microprobe analysis on clean crystals of the product gave the following results on the basis of relative peak heights:

| | Average of Spot Probes |
|---|---|
| Co | 0.12 |
| Al | 0.32 |
| P | 0.57 |

EXAMPLE 108

(Preparation of CoAPO-47)

(a) The procedure of Example 106 was repeated except that the reaction mixture was crystallized by heating in a sealed reactor at 150° C. for 408 hours. The isolated and washed product solids exhibited the same X-ray powder diffraction pattern as in Example 106. A portion of the solids that passed through a 200 mesh screen was analyzed chemically and found to contain 10.3 wt % CoO, 23.8 wt. % Al₂O₃, 43.0 wt. % P₂O₅, 10.4 wt. % C, 2.0 wt. % N and 22.8 wt. % LOI. This analysis corresponds to a composition in terms of molar oxide ratios of:

$0.48C_6H_{15}NO:0.45CoO:0.77Al_2O_3:P_2O_5:1.5H_2O$ and the essential empirical formula (anhydrous basis) of:

$0.12C_6H_{15}NO:(Co_{0.11}Al_{0.39}P_{0.50})O_2$.

EDAX microprobe analysis on clean crystals of the product gave the following analysis based on relative peak heights:

| | Average of Spot Probes |
|---|---|
| Co | 0.12 |
| Al | 0.29 |
| P | 0.58 |

(b) A portion of the product of part (a) supra was heated under vacuum at 600° C. for 5 hours. The X-ray powder diffraction pattern of this calcined CoAPO-47 was characterized by the following data:

TABLE AE

| 2θ | d, (A) | 100 × I/I₀ |
|---|---|---|
| 9.4 | 9.41 | 100 |
| 12.8 | 6.92 | 9 |
| 14.0 | 6.33 | 2 |
| 16.0 | 5.54 | 5 |
| 17.9 | 4.96 | 5 |
| 19.1 | 4.65 | 4 |
| 20.7 | 4.29 | 20 |
| 22.2 | 4.00 | 2 |
| 23.1 | 3.85 | 2 |
| 25.2 | 3.53 | 5 |
| 26.0 | 3.43 | 5 |
| 30.7 | 2.91 | 10 |
| 31.4 | 2.85 | 6 |

(c) Adsorption capacities of the sample of part (b) above were measured using a standard McBain-Bakr gravimetric adsorption apparatus. The following data were obtained on a sample activated at 370° C.:

| Adsorbate | Kinetic Diameter, A | Pressure Torr | Temp., °C. | Wt. % Adsorbed |
|---|---|---|---|---|
| O₂ | 3.46 | 12 | −183 | 17.1 |
| O₂ | 3.46 | 704 | −183 | 19.7 |
| Butane | 4.3 | 692 | 21 | 1.5 |
| Xenon | 4.0 | 754 | 23 | 17.4 |
| H₂O | 2.65 | 20 | 23 | 26.4 |

The pore size of the calcined CoAPO-47 is approximately 4.0A as indicated by the adsorption of xenon and nil adsorption of butane.

The species CoAPO-47 as referred to herein is a cobalt aluminophosphate material having a three-dimensional microporous crystal framework structure of $PO_2^+$, $AlO_2^-$ and $CoO_2^{-2}$ tetrahedral units and whose essential empirical chemical composition on an anhydrous basis is: $mR:(Co_xAl_yP_z)O_3$ wherein "R" represents at least one organic templating agent present in the intracrystalline pore system; "m" represents the moles of "R" present per mole of $(Co_xAl_yP_z)O_2$ and has a value of from zero to 0.3, "x", "y" and "z" represent respectively, the mole fractions of cobalt, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said cobalt aluminophosphate having a characteristic X-ray powder diffraction pattern which contains at least the d-spacings set forth below in TABLE XLV. In the form as synthesized in accordance with the process of this invention, "m" has a value of from 0.02 to 0.3.

TABLE XLV

| 2θ | d, (A) | Relative Intensity |
|---|---|---|
| 9.4 | 9.41 | vs |
| 16.0–16.1 | 5.54–5.50 | vw-w |
| 18.9–19.0 | 4.70–4.67 | vw-w |
| 20.6 | 4.31 | m |
| 24.6–24.7 | 3.62–3.60 | vw-w |
| 30.5–30.6 | 2.93–2.92 | w |

All of the as-synthesized CoAPO-47 compositions for which X-ray powder diffraction data have presently been obtained, have X-ray patterns within the generalized pattern of Table XLV (a), below:

TABLE XLV (a)

| 2θ | d, (A) | Relative Intensity |
|---|---|---|
| 9.4 | 9.41 | vs |
| 12.9–13.0 | 6.86–6.81 | vw |
| 13.9–14.0 | 6.37–6.33 | vw |
| 16.0–16.1 | 5.54–5.50 | vw-w |
| 17.5–17.7 | 5.07–5.01 | vw |
| 18.9–19.0 | 4.70–4.67 | vw-w |
| 20.6 | 4.31 | m |
| 21.7–21.9 | 4.10–4.06 | vw |
| 23.0 | 3.87 | vw |
| 24.6–24.7 | 3.62–3.60 | vw-w |
| 25.8–25.9 | 3.45–3.44 | vw |
| 27.6 | 3.23 | vw |
| 27.9–28.0 | 3.20–3.19 | vw |
| 29.4–29.5 | 3.04–3.03 | vw |
| 30.5–30.6 | 2.93–2.92 | w |
| 30.8–30.9 | 2.90–2.89 | shoulder |
| 33.2–33.3 | 2.70–2.69 | vw |
| 34.4–34.5 | 2.607–2.600 | vw |
| 35.6–35.8 | 2.522–2.508 | vw |
| 38.4–38.5 | 2.344–2.338 | vw |
| 39.6–39.7 | 2.276–2.270 | vw |
| 42.4–42.6 | 2.132–2.122 | vw |
| 47.6 | 1.910 | vw |
| 48.6 | 1.873 | vw-w |
| 50.3–50.4 | 1.814–1.811 | vw |
| 53.2 | 1.722 | vw |

EXAMPLE 109

(Preparation of CoAPO-39)

(a) Using the procedure described in Example 106 and using di-n-propylamine ($C_6H_{15}N$) as the templating agent, a reaction mixture was prepared having a composition in terms of molar oxide ratios of:

1.0$C_6H_{15}$N:0.20CoO:0.90$Al_2O_3$:$P_2O_5$:0.40$CH_3$COOH:5.4$C_3H_7$OH:40$H_2O$.

The reaction mixture was heated at 150° C. for 72 hours in a sealed reactor. The product mixture was filtered and the collected solids were washed with water and dried in air at ambient temperature. The solid was a mixture but the major phase exhibited an X-ray powder diffraction pattern characterized by the following data:

TABLE AF

| 2θ | d, (A) | 100 × I/I$_o$ |
|---|---|---|
| 9.3 | 9.51 | 64 |
| 13.2 | 6.71 | 32 |
| 18.3 | 4.85 | 36 |
| 21.0 | 4.23 | 92 |
| 22.7 | 3.92 | 100 |
| 26.8 | 3.33 | 6 |
| 28.6 | 3.12 | 8 |
| 29.7 | 3.01 | 20 |
| 30.0 | 2.98 | 24 |
| 32.6 | 2.75 | 8 |
| 34.4 | 2.61 | 8 |
| 37.8 | 2.38 | 8 |

A portion of the product solids was subjected to chemical analysis. The product was formed to contain 5.5 wt. % CoO, 33.0 wt. % $Al_2O_3$, 46.4 wt. % $P_2O_5$, 16.0 wt % LOI, 4.8 wt. % C, and 0.9 wt. % N, giving a product composition in terms of molar oxide ratios of:

0.20$C_6H_{15}$N:0.22CoO:0.99$Al_2O_3$:$P_2O_5$:1.6$H_2O$ or in terms of TO$_2$ units, an essential empirical formula (anhydrous basis) of:

0.05$C_6H_{15}$N:(Co$_{0.05}$Al$_{0.47}$P$_{0.48}$)O$_2$.

The species CoAPO-39 as referred to herein is a cobalt aluminophosphate material having a three-dimensional microporous crystal framework structure of $PO_2^+$, $AlO_2^-$ and $CoO_2^{-2}$ tetrahedral units, and whose essential empirical chemical composition on any anhydrous basis is:

mR:(Co$_x$Al$_y$P$_z$)O$_2$ wherein "R:" represents at least one organic templating agent present in the intracrystalline pore system; "m" represents the moles of "R" present per mole of (Co$_x$Al$_y$P$_z$)O$_2$ and has a value of from zero to 0.3, "x", "y" and "z" represent respectively, the mole fractions of cobalt, aluminum and phosphorus present in the oxide moiety, said mole fractions being within the compositional area bounded by points A, B, C and D on the ternary diagram which is FIG. 1, or preferably within the area bounded by points a, b, c and d on the ternary diagram which is FIG. 2, said cobalt aluminophosphate having a characteristic X-ray powder diffraction pattern which contains at least the d-spacings set forth below in Table XLVI. In the form as synthesized in accordance with the process of this invention, "m" has a value of from 0.02 to 0.3.

TABLE XLVI

| 2θ | d, (A) | Relative Intensity |
|---|---|---|
| 9.3 | 9.51 | m-s |
| 13.2 | 6.71 | m |
| 18.3 | 4.85 | m |
| 21.0 | 4.23 | m-s |
| 22.7 | 3.92 | vs |
| 30.0 | 2.98 | m |

EXAMPLE 110

(Preparation of metal aluminophosphate containing cobalt and magnesium)

(a) A metal aluminophosphate of the present invention containing both cobalt and magnesium and having a crystal structure topologically related to CoAPO-34 and MAPO-34 was prepared as follows: A solution prepared by dissolving 10.0 grams cobalt (II) acetate tetrahydrate and 8.6 grams magnesium acetate tetrahydrate in 76.3 grams water, was added to 65.4 grams aluminum isopropoxide. This mixture was homogenized at high speed in a blender until it was too viscous to be further blended. To this mixture was added a solution prepared by combining 46.2 grams 85 wt. % orthophosphoric acid, 46.2 grams $H_2O$ and 73.7 grams 40 wt. % aqueous tetraethylammonium hydroxide (TEAOH). The resulting mixture was blended at high speed until homogenous. The composition of the mixture in molar oxide ratios was:

1.0TEAOH:0.20CoO:0.20MgO:0.8$Al_2O_3$:1.0-$P_2O_5$:0.80$CH_3$COOH:4.8$C_3H_7$OH:50$H_2O$.

The reaction mixture was sealed in an inert plastic bottle and heated in an oven at 100° C. for 144 hours. The product mixture was filtered and the collected solids were washed with water and dried in air at ambient temperature. The solid had an X-ray powder diffraction pattern essentially identical to that of MAPO-34 or CoAPO-34 (Tables K and WW, respectively). A portion of the product solids was subjected to chemical analysis. The product was found to contain 2.5 wt. % MgO, 4.8 wt. % CoO, 26.6 wt. % $Al_2O_3$, 45.9 wt. % $P_2O_5$, 19.8 wt. % LOI, 9.1 wt. % C, and 1.3 wt. % N, giving a product composition in terms of molar oxide ratios of:

0.29TEAOH:0.19MgO:0.20CoO:0.81Al$_2$O$_3$:-P$_2$O$_5$:1.3H$_2$O or in terms of TO$_2$ units, an essential empirical formula (anhydrous basis) of 0.07TEAOH:(Mg$_{0.05}$Co$_{0.05}$Al$_{0.40}$P$_{0.50}$)O$_2$.

(b) Energy dispersive analysis by X-ray microprobe analysis in conjunction with scanning electron microscope studies on clean crystals having a crystal morphology characteristic of CoAPO-34 and MAPO-34 produced the following data based on relative peak heights:

|  | Average of Spot Probes |
|---|---|
| Mg | 0.04 |
| Co | 0.04 |
| Al | 0.36 |
| P | 0.56 |

EXAMPLE 111

(Preparation of metal aluminophosphate containing cobalt and manganese)

(a) Using the procedure described in Example 110 with manganese (II) acetate tetrahydrate instead of magnesium acetate tetrahydrate, a reaction mixture of the following composition in molar oxide ratios was prepared:

1.0TEAOH:0.20CoO:0.20MnO:0.80Al$_2$O$_3$:-P$_2$O$_5$:0.8CH$_3$COOH:4.8C$_3$H$_7$OH:50H$_2$O.

The reaction mixture was sealed in an inert plastic bottle and heated in an oven at 100° C. for 120 hours. The product mixture was filtered and the collected solids were washed with water and dried in air at ambient temperature. The solid had an X-ray powder diffraction pattern essentially identical to that of CoAPO-34 (Table WW). A portion of the product solids was subjected to chemical analysis. The product was found to contain 4.3 wt. % MnO, 4.5 wt. % CoO, 25.5 wt. % Al$_2$O$_3$, 43.5 wt. % P$_2$O$_5$, 20.9 wt. % LOI, 7.6 wt. % C, and 1.1 wt. % N, giving a product composition in terms of molar oxide ratios of:

0.26TEAOH:0.20 MnO:0.20CoO:0.82 Al$_2$O$_3$:-P$_2$O$_5$:1.9 H$_2$O or in terms of TO$_2$ units, an essential empirical formula (anhydrous basis) of:

0.06 TEAOH:(Co$_{0.05}$Mn$_{0.05}$Al$_{0.41}$P$_{0.50}$)O$_2$.

(b) Energy dispersive analysis by X-ray mocroprobe in conjunction with scanning electron microscope studies on clean crystals of part (a) having the crystal morphology characteristic of CoAPO-34 yielded the following data based on relative peak heights:

|  | Average of Spot Probes |
|---|---|
| Co | 0.04 |
| Mn | 0.06 |
| Al | 0.34 |
| P | 0.56 |

EXAMPLE 112

(Preparation of metal aluminophosphate containing magnesium and cobalt)

(a) Using the procedure described in example 110 and N,N-diethylethanolamine (C$_6$H$_{15}$NO) instead of TEAOH, a reaction mixture of the following composition in molar oxide ratios was prepared:

2.0C$_6$H$_{15}$NO:0.25CoO:0.25MgO:0.75Al$_2$O$_3$:-P$_2$O$_5$:1.0CH$_3$COOH:4.5C$_3$H$_7$OH:50H$_2$O.

The reaction mixture was sealed in a stainless steel reactor and heated in an oven at 150° C. for 48 hours. The product mixture was filtered and the collected solids were washed with water and dried in air at ambient temperature. The solid had an X-ray powder diffraction pattern essentially identical to that of MAPO-47 (Table U). A portion of the solid was subjected to chemical analysis. The product was found to contain 3.1 wt % MgO, 6.6 wt. % CoO, 24.2 wt. % Al$_2$O$_3$, 42.0 wt. % P$_2$O$_5$, 23.8 wt. % LOI, 9.1 wt. % C, and 1.7 wt. % N, giving a product composition in terms of molar oxide ratios of:

0.32C$_6$H$_{15}$NO:0.30CoO:0.26MgO:0.80Al$_2$O$_3$:-P$_2$O$_5$:2.1H$_2$O or in terms of TO$_2$ units, an essential empirical formula (anhydrous basis) of: 0.10C$_6$H$_{15}$NO:(Co$_{0.07}$Mg$_{0.06}$Al$_{0.39}$P$_{0.48}$)O$_2$.

(b) Energy dispersive analysis by X-ray (EDAX) in conjunction with scanning electron microscope studies on clean crystals of part (a) having the characteristic morphology of MAPO-47 yielded the following data based on relative peak heights:

|  | Average of Spot Probes |
|---|---|
| Co | 0.05 |
| Mg | 0.04 |
| Al | 0.33 |
| P | 0.58 |

Additional electron microprobe analysis was carried out on selected samples of metal aluminophosphate samples of the present invention. The samples were mounted in epoxy resin, polished and carbon coated. Elemental analyses were determined by both energy dispersive (EDS) and wavelength dispersive (WDS) techniques using standards and reported correction procedures. The electron microprobe analyses were carried out on individual crystallites of typical morphology. In all cases, P constituted approximately 50% of the T atoms and Al 33–47%. The divalent element was present in amounts varying from 3–16% of the T atoms depending on structure-type. For example, MnAPO-44 exhibits ca. 4 times the level of Mn substitution for Al as MnAPO-11. Multiple spot analyses of some of the larger crystals indicated compositional uniformity from edge to center with no pronounced zoning. Where available, bulk chemical analyses compared very favorably with those from the electron microprobe. The data are set forth in tabular form below:

| | N MICROPROBE ANALYSIS OF SELECTED SAMPLES | | | | | | | | | | |
|---|---|---|---|---|---|---|---|---|---|---|---|
| Structure | Weight % | | | | | Normalized Elemental Ratio | | | | | |
| Type | Al$_2$O$_3$ | P$_2$O$_5$ | MnO | MgO | CoO | Al | P | Mn | Mg | Co | Technique* |
| MnAPO-11 | 34.8 | 54.0 | 3.7 | — | — | 0.46 | 0.51 | 0.03 | — | — | 1 |
|  | 33.5 | 55.1 | 3.2 | — | — | 0.44 | 0.53 | 0.03 | — | — | 2 |

N MICROPROBE ANALYSIS OF SELECTED SAMPLES -continued

| Structure Type | Weight % | | | | | Normalized Elemental Ratio | | | | | Technique* |
|---|---|---|---|---|---|---|---|---|---|---|---|
| | Al₂O₃ | P₂O₅ | MnO | MgO | CoO | Al | P | Mn | Mg | Co | |
| | 31.8 | 53.7 | 4.0 | — | — | 0.43 | 0.53 | 0.04 | — | — | 2 |
| MnAPO-44 | 22.5 | 45.8 | 13.9 | — | — | 0.34 | 0.50 | 0.15 | — | — | 1 |
| | 20.5 | 45.5 | 13.7 | — | — | 0.33 | 0.52 | 0.16 | — | — | 2 |
| | 21.7 | 47.6 | 13.0 | — | — | 0.33 | 0.52 | 0.14 | — | — | 2 |
| | 22.2 | 43.5 | 11.7 | — | — | 0.36 | 0.51 | 0.14 | — | — | 3 |
| MAPO-47 | 26.9 | 48.6 | — | 5.0 | — | 0.39 | 0.51 | — | 0.09 | — | 1 |
| | 22.6 | 46.4 | — | 6.8 | — | 0.35 | 0.52 | — | 0.13 | — | 2 |
| | 23.9 | 46.0 | — | 6.7 | — | 0.37 | 0.51 | — | 0.13 | — | 2 |
| | 24.5 | 43.9 | — | 5.3 | — | 0.39 | 0.50 | — | 0.11 | — | 3 |
| CoAPO-47 | 24.9 | 46.9 | — | — | 10.9 | 0.38 | 0.51 | — | — | 0.11 | 1 |
| | 23.0 | 47.5 | — | — | 9.6 | 0.36 | 0.54 | — | — | 0.10 | 2 |
| | 24.8 | 49.0 | — | — | 10.0 | 0.37 | 0.53 | — | — | 0.10 | 2 |
| | 23.8 | 43.0 | — | — | 10.3 | 0.39 | 0.50 | — | — | 0.11 | 3 |
| CoAPO-5 | 34.9 | 52.5 | — | — | 2.9 | 0.47 | 0.51 | — | — | 0.03 | 1 |
| | 34.7 | 55.1 | — | — | 2.8 | 0.46 | 0.52 | — | — | 0.03 | 2 |
| | 33.5 | 51.7 | — | — | 2.9 | 0.46 | 0.51 | — | — | 0.03 | 2 |

*1 = Energy dispersive, 2 = Wavelength dispersive, 3 = bulk chemical

As an indication of the catalytic activity, particularly the cracking activity, of the present class of novel metal organosilicates, certain of the MeAPO species were tested for n-butane cracking using a bench-scale apparatus. The reactor was a cylindrical quartz tube 254 mm. in length and 10.3 mm. I.D. In each test the reactor was loaded with particles of the test MeAPO which were 20-40 mesh (U.S. std.) in size and in an amount of from 0.5 to 5 grams, the quantity being selected so that the conversion of n-butane was at least 5% and not more than 90% under the test conditions. Most of the MeAPO samples had been previously calcined in air to remove organic materials from the pore system, and were activated in situ in the reactor in a flowing stream of helium at 500° C. for one hour. The feedstock was a helium-n-butane mixture containing 2 mole percent n-butane and was passed through the reactor at a rate of 50 cc./minute. Analysis of the feedstock and the reactor effluent were carried out using conventional gas chromatography techniques. The reactor effluent was analyzed after 10 minutes of on-stream operation. From the analytical data the pseudo-first-order rate constant ($k_A$) was calculated. Pertinent data is set forth in tabular form below.

| Sample of Example No. | Species | Air Calcination Before Test | $K_A$ |
|---|---|---|---|
| 1* | MAPO-5 | 600° C., 3 hrs. | 0.5 |
| 17 | MAPO-11 | 600° C., 58 hrs. | 0.2 |
| 36 | MAPO-34 | 600° C., 1 hr. | 9.1 |
| 42 | MAPO-36 | 600° C., 2 hrs. | 19.7 |
| 47* | MAPO-39 | 600° C., 20 hrs. | 0.05 |
| 75 | MnAPO-11 | 500° C., 22 hrs. | 0.5 |
| 70 | MnAPO-5 | 500° C., 4 hrs. | 1.2 |
| 79 | MnAPO-34 | None | 5.2 |
| 91 | CoAPO-5 | 600° C., 2 hrs. | 0.4 |
| 98 | CoAPO-34 | None | 14.5 |
| 103 | CoAPO-36 | 500° C., 4 hrs. | 8.1 |

The MeAPO compositions of the present invention are, in general, hydrophilic and adsorb water preferentially over common hydrocarbon molecules such as paraffins, olefins and benzenoid aromatic species, e.g., benzene, xylenes and cumene. Thus the present metal aluminophosphates as a class are useful as desiccants in such adsorption separation/purification processes as natural gas drying, cracked gas drying. Water is also preferentially adsorbed over the so-called permanent gases such as carbon dioxide, nitrogen, oxygen and hydrogen. These metal aluminophosphates are therefore suitably employed in the drying of reformer hydrogen streams and in the drying of oxygen, nitrogen or air prior to liquifaction. In this respect the adsorptive properties of the present metal aluminophosphates appears to be quite similar to those of the low silica aluminosilicate zeolites, despite the fact that they exhibit, at best, a modest ion-exchange capacity.

The present MeAPO compositions also exhibit novel surface selectivity characteristics which render them useful as catalyst or catalyst bases in a number of hydrocarbon conversion and oxidative combustion reactions. They can be impregnated or otherwise loaded with catalytically active metals by methods well known in the art and used, for example, in fabricating catalysts compositions having silica or alumina bases. Of the general class, those species having pores larger than about 5 A are preferred for catalytic applications.

Among the hydrocarbon conversion reactions catalyzed by MeAPO compositions are cracking, hydrocracking, alkylation for both the aromatic and isoparaffin types, isomerization including xylene isomerization, polymerization, reforming, hydrogenation, dehydrogenation, transalkylation, dealkylation, hydrodecyclization and dehydrocyclization.

Using MeAPO catalyst compositions which contain a hydrogenation promoter such as platinum or palladium, heavy petroleum residual stocks, cyclic stocks and other hydrocrackable charge stocks can be hydrocracked at temperatures in the range of 400° F. to 825° F. using molar ratios of hydrogen to hydrocarbon in the range of between 2 and 80, pressures between 10 and 3500 p.s.i.g., and a liquid hourly space velocity (LHSV) of from 0.1 to 20, preferably 1.0 to 10.

The MeAPO catalyst compositions employed in hydrocracking are also suitable for use in reforming processes in which the hydrocarbon feedstocks contact the catalyst at temperatures of from about 700° F. to 1000° F., hydrogen pressures of from 100 to 500 p.s.i.g., LHSV values in the range of 0.1 to 10 and hydrogen to hydrocarbon molar ratios in the range of 1 to 20, preferably between 4 and 12.

These same catalysts, i.e. those containing hydrogenation promoters, are also useful in hydroisomerizations processes in which feedstocks such a normal paraffins are converted to saturated branched chain isomers. Hydroisomerization is carried out at a temperature of from about 200° F. to 600° F., preferably 300° F. to 550°

F. with an LHSV value of from about 0.2 to 1.0. Hydrogen is supplied to the reactor in admixture with the hydrocarbon feedstock in molar proportions (H/Hc) of between 1 and 5.

At somewhat higher temperatures, i.e. from about 650° F. to 1000° F., preferably 850° F. to 950° F. and usually at somewhat lower pressures within the range of about 15 to 50 p.s.i.g., the same catalyst compositions are used to hydroisomerize normal paraffins. Preferably the paraffin feedstock comprises normal paraffins having a carbon number range of $C_7$–$C_{20}$. Contact time between the feedstock and the catalyst is generally relatively short to avoid undersireable side reactions such as olefin polymerization and paraffin cracking. LHSV values in the range of 0.1 to 10, preferably 1.0 to 6.0 are suitable.

The unique crystal structure of the present MeAPO catalysts and their availability in a form totally void of alkali metal content favor their use in the conversion of alkylaromatic compounds, particularly the catalytic disproportionation of toluene, ethylene, trimethyl benzenes, tetramethyl benzenes and the like. In the disproportionation process isomerization and transalkylation can also occur. Group VIII noble metal adjuvents alone or in conjunction with Group VI-B metals such as tungsten, molybdenum and chromium are preferably included in the catalyst composition in amounts of from about 3 to 15 weight-% of the overall composition. Extraneous hydrogen can, but need not, be present in the reaction zone which is maintained at a temperature of from about 400° to 750° F., pressures in the range of 100 to 2000 p.s.i.g. the LHSV values in the range of 0.1 to 15.

Catalytic cracking processes are preferably carried out with MeAPO compositions using feedstocks such as gas oils, heavy naphthas, deasphalted crude oil residua, etc., with gasoline being the principal desired product. Temperature conditions of 850° to 1100° F., LHSV values of 0.5 to 10 and pressure conditions of from about 0 to 50 p.s.i.g. are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the MeAPO catalyst in conjunction with a Group VIII non-noble metal cation such as cobalt and nickel.

In catalytic dealkylation wherein it is desired to cleave paraffinic side chains from aromatic nuclei without substantially hydrogenating the ring structure, relatively high temperatures in the range of about 800°–1000° F. are employed at moderate hydrogen pressures of about 300–1000 p.s.i.g., other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like any of which may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of catalysts of hydrocracking. Consequently, it is necessary to operate at more extreme conditions when it is desired to obtain the same degree of hydrocracking conversion per mass on a relatively nitrogenous feed than are required with a feed containing less organonitrogen compounds. Consequently, the conditions under which denitrogenation, desulfurization and/or hydrocracking can be most expeditiously accomplished in any given situation are necessarily determined in view of the characteristics of the feedstocks in particular the concentration of organonitrogen compounds in the feedstock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking inhibiting constituents e.g., organonitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500°–900° F., while paraffins, naphthenes and alkyl aromatics are isomerized at temperatures of 700°–1000° F. Particularly desirable isomerization reactions contemplated herein include the conversion of n-heptene and/or n-octane to isoheptanes, iso-octanes, butane to iso-butane, methylcyclopentane to cyclohexane, meta-xylene and/or ortho-xylene to paraxylene, 1-butene to 2-butene and/or isobutene, n-hexene to isohexene, cyclohexene to methylcyclopentene etc. The preferred cation form is a combination of the MeAPO with polyvalent metal compounds (such as sulfides) of metals of Group II-A, Group II-B and rare earth metals. For alkylation and dealkylation processes the MeAPO compositions having pores of at least 5 A are preferred. When employed for dealkylation of alkyl aromatics, the temperature is usually at least 350° F. and ranges up to a temperature at which substantial cracking of the feedstock or conversion products occurs, generally up to about 700° F. The temperature is preferably at lest 450° F. and not greater than the critical temperature of the compound undergoing delakylation. Pressure conditions are applied to retain at least the aromatic feed in the liquid state. For alkylation the temperature can be as low as 250° F. but is preferably at least 360° F. In alkylation benzene, toluene and xylene, the preferred alkylating agent are olefins such as ethylene and propylene.

We claim:

1. Process for catalytically converting a hydrocarbon which comprises contacting said hydrocarbon under hydrocarbon converting conditions with a crystalline metal aluminophosphate having a three-dimensional microporous framework structure of $MO_2^{-2}$, $AlO_2^{-}$, and $PO_2^{+}$ tetrahedral units and having an empirical chemical composition on an anhydrous basis expressed by the formula $$mR: (M_xAL_yP_z)O_2$$

wherein "R" represents at least one organic templating agent present in the intracrystalline pore system, "m" represents the moles of "R" present per mole of $(M_xAL_yP_z)O_2$ and has a value of from zero to 0.3, "M" represents at least one metal of the group magnesium, manganese, zinc and cobalt, "x", "y" and "z" represent the mole fraction of the metal "M", aluminum and phosphorus respectively present as tetrahedral oxides, said mole fractions being such that they are within the tetragonal compositional area defined by points A, B, C and D of the ternary diagram which is FIG. 1 of the drawings, or by the tetragonal compositional area defined by points a, b, c and d of the ternary diagram which is FIG. 2 of the drawings.

2. Process according to claim 1 wherein the hydrocarbon conversion process is cracking.

3. Process according to claim 1 wherein the hydrocarbon conversion process is hydrocracking.

4. Process according to claim 1 wherein the hydrocarbon conversion process is hydrogenation.

5. Process according to claim 1 wherein the hydrocarbon conversion process is polymerization.

6. Process according to claim 1 wherein the hydrocarbon conversion process is alkylization.

7. Process according to claim 1 wherein the hydrocarbon conversion process is reforming.

8. Process according to claim 1 wherein the hydrocarbon conversion process is hydrotreating.

9. Process according to claim 1 wherein the hydrocarbon conversion process is isomerization.

10. Process according to claim 1 wherein the isomerization conversion process is xylene isomerization.

11. Process according to claim 1 wherein the hydrocarbon conversion is dehydrocyclization.

* * * * *